(12) United States Patent
Maliga

(10) Patent No.: US 11,208,665 B2
(45) Date of Patent: Dec. 28, 2021

(54) COMPOSITIONS AND METHODS FOR IMPROVING PLASTID TRANSFORMATION EFFICIENCY IN HIGHER PLANTS

(71) Applicant: RUTGERS, THE STATE UNIVERSITY OF NEW JERSEY, New Brunswick, NJ (US)

(72) Inventor: Pal Maliga, East Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 16/506,756

(22) Filed: Jul. 9, 2019

(65) Prior Publication Data

US 2020/0017868 A1 Jan. 16, 2020

Related U.S. Application Data

(63) Continuation-in-part of application No. PCT/US2018/013034, filed on Jan. 9, 2018.

(60) Provisional application No. 62/444,307, filed on Jan. 9, 2017.

(51) Int. Cl.
*C12N 15/82* (2006.01)

(52) U.S. Cl.
CPC .................. *C12N 15/8214* (2013.01)

(58) Field of Classification Search
None
See application file for complete search history.

(56) References Cited

U.S. PATENT DOCUMENTS

| 6,376,744 | B1 * | 4/2002 | Maliga | C12N 15/8214 |
| | | | | 435/320.1 |
| 6,515,206 | B1 * | 2/2003 | Chaudhuri | C12N 15/8214 |
| | | | | 435/419 |
| 7,129,391 | B1 * | 10/2006 | Daniell | C12N 15/8286 |
| | | | | 800/278 |
| 8,841,511 | B2 * | 9/2014 | Maliga | C12N 15/8209 |
| | | | | 800/278 |
| 2015/0067922 | A1 * | 3/2015 | Yang | C12N 15/8273 |
| | | | | 800/298 |

OTHER PUBLICATIONS

Parker et al (2016, Plant Physiol. 172:1862-1875, including Supplementary materials).*
Czako et al (1993, Plant Cell Rep. 12:603-606).*
Li et al (2009, GenBAnk Accession No. FJ719766, https://www.ncbi.nlm.nih.gov/nuccore/FJ719766).*
Barkan et al, "A Combination Amino Acid Code for RNA Recognition by Pentatricopeptide Repeat Proteins", Institute of Molecular Biology, Aug. 2012, vol. 8—Issue 8, PLOS Genetics.
Barkan et al, "Pentatricopeptide Repeat Proteins in Plants", Institute of Molecular Biology, Jan. 16, 2014, Annual Review Plant Biology.
Belhaj et al, "Plant Genome Editing Made Easy: Targeting Mutagensis in Model and Crop Plants Using the CRISPR/CAS System" Plant Methods 2013, vol. 9.
Cheng et al, "Chorloplast Transformation of Rapeseed (*Brassica napus*) by Particle Bombardment of Cotyledons", Plant Cell Rep, 2010, vol. 29, pp. 371-381, Springer-Verlag.
De Jaeger et al, "Boosting Heterologous Protein Production in Transgenic Dicotyledonous Seeds Using Phaseolus Vulgaris Regulatory Sequences", Nature Biotechnology, Dec. 2002, vol. 20, Nature Publishing Group.
Ellerstorm, M. et al, "Functional Dissection of a Napin Gene Promoter; Identification of Promoter Elements Required for Embryo and Endosperm-Specific Transcription", Plant Molecular, 1996, pp. 1019-1027, vol. 32, Issue 6.
Skarjinskaia Marina et al, "Plastid Transformation in Lesquerella Fendleri, an Oilseed Brassicacea", 2003, Transgenic Research, vol. 12, pp. 115-122, Kluwer Academic Publishers.
Sikdar, S.R. et al, "Plastid Transformation in *Arabidopsis thaliana*", Plant Cell Reports, 1998, vol. 18 pp. 20-24, Springer-Verlag 1998.
Parker, Nicole et al., "Natural Variation in Sensitivity to a Loss of Chloroplast Translation in *Arabidopsis*", Plant Physiology, Dec. 2014, vol. 166, pp. 2013-2027, American Society of Plant Biologists.
Mao Y. et al., "Application of the CRISPR-CAS System for Efficient Genome Engineering in Plants", Nov. 2013, Molecular Plant, vol. 6, Issue 6, pp. 2008-2011.
Feng, Z. et al., "Multigeneration Analysis Reveals the Inheritance, Specificity, and Patterns of CRISPR/CAS-Induced Gene Modifications in *Arabidopsis*", Mar. 25, 2014, PNAS, vol. 111, Issue 12, pp. 4632-4637.

\* cited by examiner

*Primary Examiner* — Anne Kubelik
(74) *Attorney, Agent, or Firm* — Kathleen D. Rigaut; Howson & Howson LLP

(57) ABSTRACT

Compositions and methods for improving plastid transformation in difficult to transform plants are disclosed.

10 Claims, 15 Drawing Sheets

Specification includes a Sequence Listing.

```
Alignment of Sequence_1: [Y10302.xdna] with Sequence_2: [X77576.xdna]
Similarity : 291/298 (97.65 %)

Seq_1    1   ATGGAGATGAGAGCTTTAGTTTCGTGTTCKGCTGCGCCAAATGGAGCTTCTGATCCGTTT  60
Seq_2    1   ATGGAGATGAGAGCTTTGGTTTCGTGTTCKGCTGCCCAAATGGAGCTTCTGATCCGTTT  60

Seq_1   61   AGACTCTCCAATGTTTCACCATGGATCACATCAGCTCCGGTGCAAGTGGCAGTGACTCC  120
Seq_2   61   AGACTCTCCAATGTTTCACCATGAATCACATCAGCTCCGTGTGCAAGTGGCAGTGACTCC  120

Seq_1  121   CCAGCCACAGTGAAGCTGGGAACCAGCTCTATGATTAGAGCTTTCAAAGGGTTTCGATT  180
Seq_2  121   CCAGCCACAGTGAAGCTGGGAACCAGCTCTATGATCAGAGCCTTCAAAGGAGTTTCGATT  180

Seq_1  181   TACAAAAACAAGACCAGAGGGAATGTTCTGTCTCAAAGGAACAAACAGTTCCGTCCTATG  240
Seq_2  181   TACAAAAACAAGACCAGAGAAATGTTTGTCTCAAAGGAACAAACAGTTCGTCCTATG  240

Seq_1  241   GCCTACTTAGGAAGGAAGGACTTGAGCAGCCCTGATCCGACCTCCTTCTGCGATAATG  298
Seq_2  241   GCCTACTTAGGAAGGAAGGACTTGAGCAGCCCCTGATCCCGACCTCCTTCTGCGATAATG  298
```

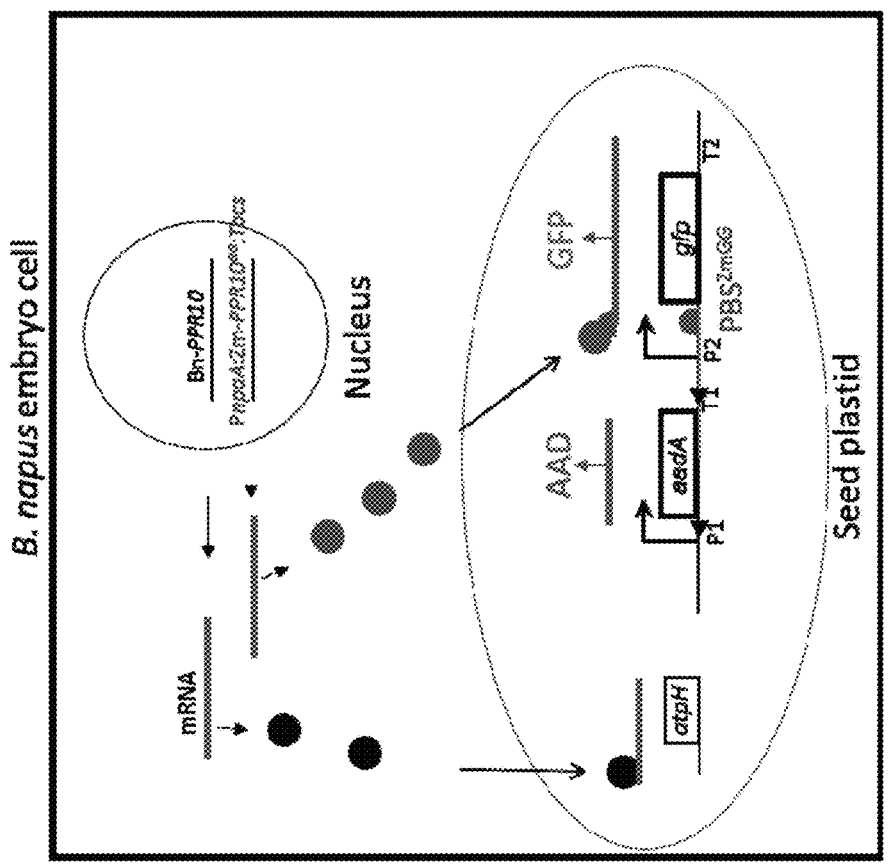
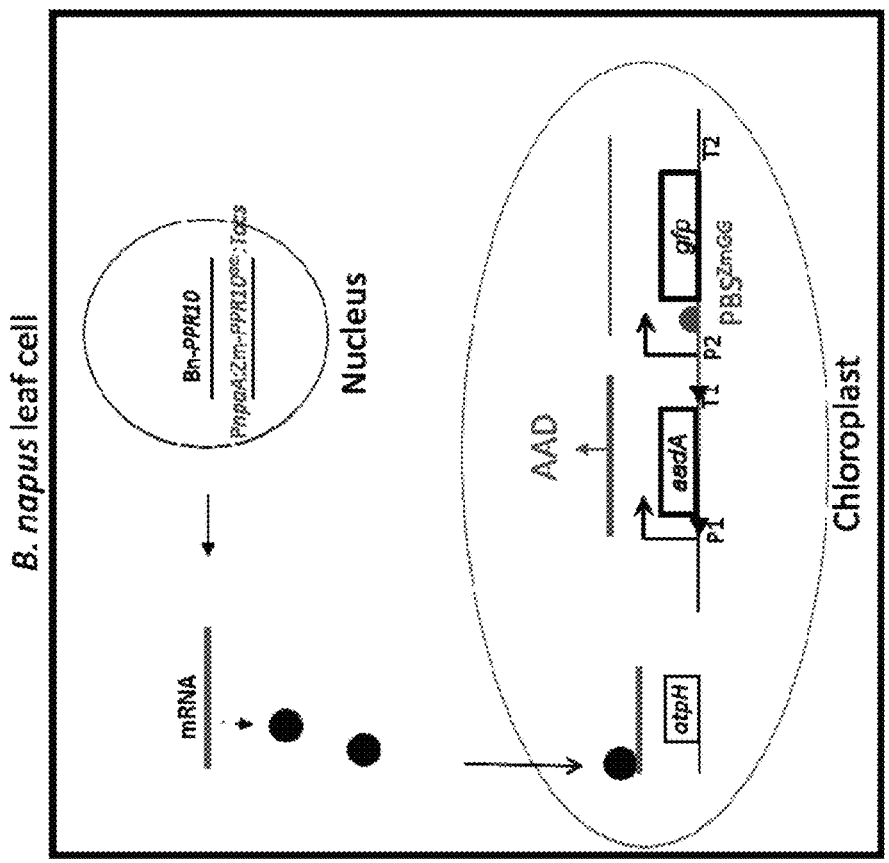
Fig. 11

Fig. 14A
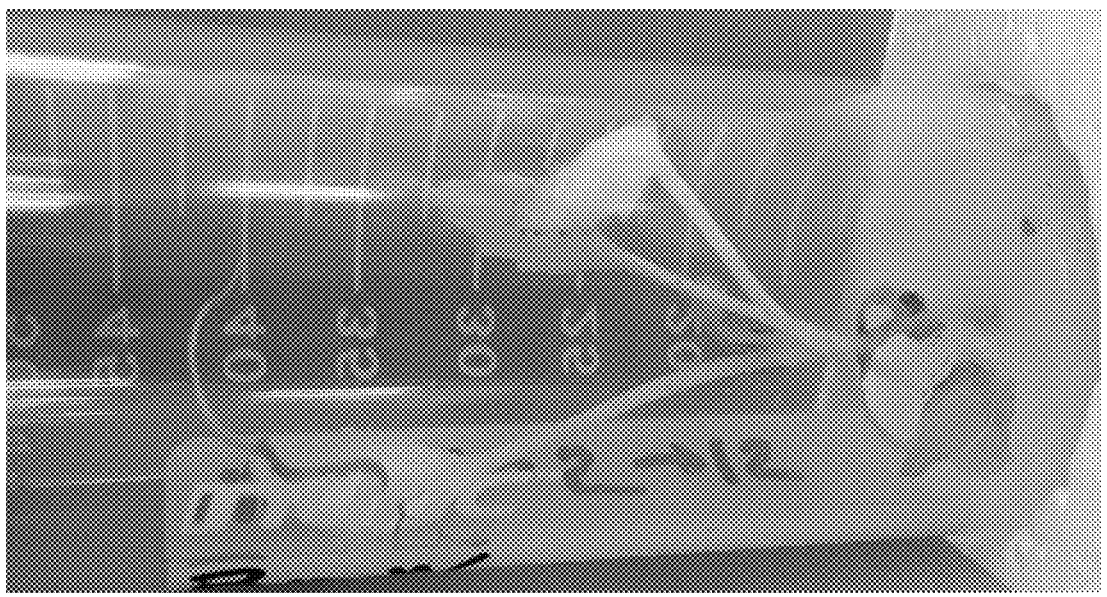
15 mg/L
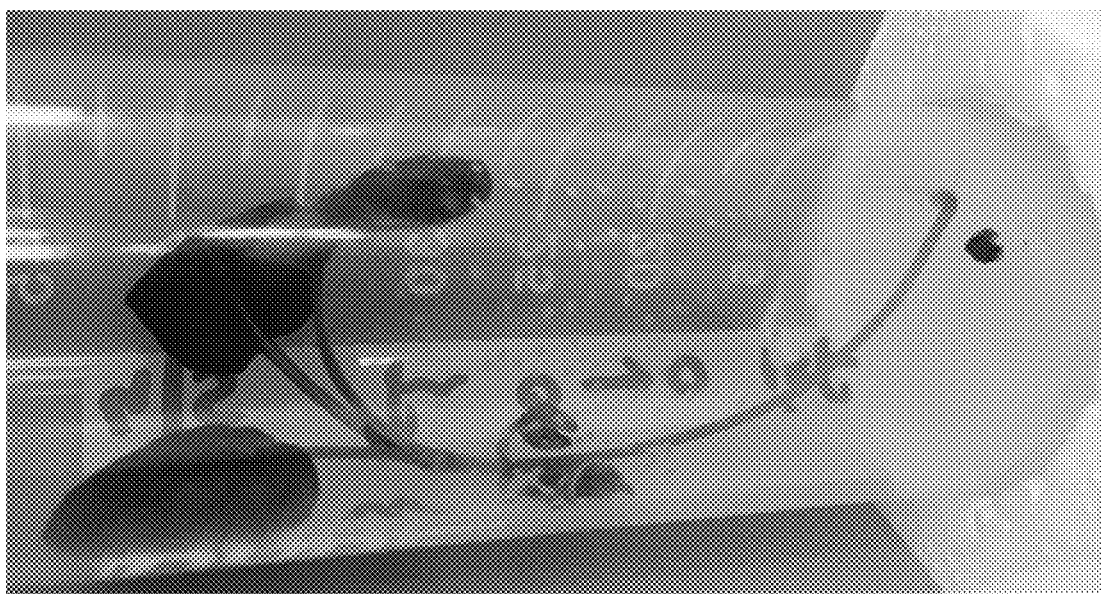
0 mg/L

SEQUENCE LISTING

```
<160> NUMBER OF SEQ ID NOS: 353

<210> SEQ ID NO 1
<211> LENGTH: 2043
<212> TYPE: DNA
<213> ORGANISM: Artificial Sequence
<220> FEATURE:
<223> OTHER INFORMATION: EcoRI-HindIII fragment

<400> SEQUENCE: 1
gagctcgctc ccccgccgtc gttcaatgag aatggataag aggctcgtgg gattgacgtg      60 aggggggcagg gatggctata tttctgggag aattaaccga tcgacgtgca agcggacatt    120
tattttaaat tcgataattt ttgcaaaaac atttcgacat atttatttat tttattatta    180
tgagaatcaa tcctactact tctggttctg gggtttccac ggctactagc gaagcggtga    240
tcgccgaagt atcgactcaa ctatcagagg tagttggcgt catcgagcgc catctcgaac    300
cgacgttgct ggccgtacat ttgtacggct ccgcagtgga tggcggcctg aagccacaca    360
gtgatattga tttgctggtt acggtgaccg taaggcttga tgaaacaacg cggcgagctt    420
tgatcaacga ccttttggaa acttcggctt ccctggaga gagcgagatt ctccgcgctg    480
tagaagtcac cattgttgtg cacgacgaca tcattccgtg gcgttatcca gctaagcgcg    540
aactgcaatt tggagaatgg cagcgcaatg acattcttgc aggtatcttc gagccagcca    600
cgatcgacat tgatctggct atcttgctga caaaagcaag agaacatagc gttgccttgg    660
taggtccagc ggcggaggaa ctctttgatc cggttcctga acaggatcta tttgaggcgc    720
taaatgaaac cttaacgcta tggaactcgc cgcccgactg ggctggcgat gagcgaaatg    780
tagtgcttac gttgtcccgc atttggtaca gcgcagtaac cggcaaaatc gcgccgaagg    840
atgtcgctgc cgactgggca atggagcgcc tgccggccca gtatcagccc gtcatacttg    900
aagctagaca ggcttatctt ggacaagaag aagatcgctt ggcctcgcgc gcagatcagt    960
tggaagaatt tgtccactac gtgaaggcg agatcaccaa ggtagtgggc aaagaacaaa   1020
aactcatttc tgaagaagac ttgtaactgc agataaccca aataatgttt taaatttta    1080 aaaataatgt aggaggaaaa attatggcta gcagtaaagg agaagaactt ttcactggag   1140
ttgtcccaat tcttgttgaa ttagatggtg atgttaatgg gcacaaattt tctgtcagtg   1200
gagagggtga aggtgatgca acatacggaa aacttaccct taaatttatt tgcactactg   1260
```

-continued

```
gaaaactacc tgttccttgg ccaacacttg tcactacttt ctcttatggt gttcaatgct    1320
tttcaagata cccagatcat atgaagcggc acgacttctt caagagcgcc atgcctgagg    1380
gatacgtgca ggagaggacc atctctttca aggacgacgg aactacaag  acacgtgctg    1440 aagtcaagtt tgagggagac accctcgtca caggatcga  gcttaaggga atcgatttca    1500
aggaggacgg aaacatcctc ggccacaagt tggaatacaa ctacaactcc cacaacgtat    1560
acatcacggc agacaaacaa aagaatggaa tcaaagctaa cttcaaaatt agacacaaca    1620
ttgaagatgg aagcgttcaa ctagcagacc attatcaaca aaatactcca attggcgatg    1680
gccctgtcct tttaccagac aaccattacc tgtccacaca atctgccctt tcgaaagatc    1740
ccaacgaaaa gagagaccac atggtccttc ttgagtttgt aacagctgct gggattacac    1800
atggcatgga tgaactatac aaataagctc tagctagagc gatcctggcc tagtctatag    1860
gaggttttga aagaaagga  gcaataatca ttttcttgtt ctatcaagag ggtgctattg    1920
ctcctttctt ttttctttt  tatttattta ctagtatttt acttacatag acttttttgt    1980
ttacattata gaaaagaag  gagaggttat ttcttgcat  ttattcatgg gggatcaaag    2040
ctt                                                                  2043
```

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
ttttctgtca gtggagaggg tg                                             22

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
cccagcagct gttacaaact                                                20

<210> SEQ ID NO 4
<211> LENGTH: 23
<212> TYPE: DNA
<213> ORGANISM: Artificial Sequence
<220> FEATURE:
<223> OTHER INFORMATION: gRNA design
<220> FEATURE:
<221> NAME/KEY: misc_feature
<222> LOCATION: (1)..(21)
<223> OTHER INFORMATION: n is a, c, g, or t

<400> SEQUENCE: 4
nnnnnnnnnn nnnnnnnnnn ngg                                            23

<210> SEQ ID NO 5
<211> LENGTH: 100
<212> TYPE: PRT
<213> ORGANISM: Arabidopsis thaliana

<400> SEQUENCE: 5

Met Glu Met Arg Ala Leu Gly Ser Ser Cys Ser Thr Gly Asn Gly Gly
 1               5                  10                  15

```
Ser Ala Pro Ile Thr Leu Thr Asn Ile Ser Pro Trp Ile Thr Thr Val
            20                  25                  30

Phe Pro Ser Thr Val Lys Leu Arg Ser Ser Leu Arg Thr Phe Lys Gly
        35                  40                  45

Val Ser Ser Arg Val Arg Thr Phe Lys Gly Val Ser Ser Thr Arg Val
 50                  55                  60

Leu Ser Arg Thr Lys Gln Gln Phe Pro Leu Phe Cys Phe Leu Asn Pro
 65                  70                  75                  80

Asp Pro Ile Ser Phe Leu Glu Asn Asp Val Ser Glu Ala Glu Arg Thr
                85                  90                  95

Val Val Leu Pro
            100

<210> SEQ ID NO 6
<211> LENGTH: 300
<212> TYPE: DNA
<213> ORGANISM: Arabidopsis thaliana

<400> SEQUENCE: 6
atggagatga gagctttggg ttcttcgtgt tctactggta atggaggttc tgctccgatt      60
accctcacga atatatctcc atggatcaca acagttttc cgtcgacagt gaagctgaga     120
agtagtttga gaaccttcaa aggagtttcg tcaagagtga aacctttaa aggagtttct     180 tcgacaagag ttttgtctcg gaccaaacaa cagtttcctc tgtttttgttt cctaaaccct     240 gatccgatct ccttcttgga aaatgatgta tctgaagctg aaaggacagt agttttaccg     300

<210> SEQ ID NO 7
<211> LENGTH: 100
<212> TYPE: PRT
<213> ORGANISM: Arabidopsis lyrata

<400> SEQUENCE: 7

Met Glu Met Arg Ala Leu Val Ser Ser Cys Ala Thr Gly Asn Gly Gly
 1               5                  10                  15

Ser Asp Pro Phe Ser Phe Thr Lys Val Ser Pro Trp Ile Thr Thr Val
            20                  25                  30

Gly Gly Lys Asp Arg Asp Phe Pro Thr Thr Val Lys Leu Arg Thr Ser
        35                  40                  45

Met Arg Thr Phe Lys Gly Val Ser Ile Arg Gly Arg Thr Phe Lys Gly
     50                  55                  60

Val Ser Thr Arg Val Leu Ser Arg Asn Lys Gln Gln Phe Pro Leu Phe
 65                  70                  75                  80

Cys Phe Leu Asn Pro Asp Pro Thr Ser Phe Arg Asp Asn Asp Ile Ser
                85                  90                  95

Glu Ala Gln Arg
            100

<210> SEQ ID NO 8
<211> LENGTH: 300
<212> TYPE: DNA
<213> ORGANISM: Arabidopsis lyrata

<400> SEQUENCE: 8
atggagatga gagctttggt ttcttcgtgt gctaccggta atggaggttc tgatccgttt      60
agcttcacga aagtttctcc atggatcaca acagttggtg gtaaggacag agattttcca     120
acgacagtga agctaagaac tagtatgaga acctttaaag gagtttctat aagagggaga     180
```

```
accctttaaag gagtttcgac aagagttttg tctcggaaca acaacagttt tcctctgttt      240
tgtttcctaa accctgatcc gacctccttc cgggataatg atatatctga agctcaaagg      300
```

<210> SEQ ID NO 9
<211> LENGTH: 23
<212> TYPE: DNA
<213> ORGANISM: Artificial Sequence
<220> FEATURE:
<223> OTHER INFORMATION: gRNA

<400> SEQUENCE: 9
ttggtttctt cgtgtgctac cgg      23

<210> SEQ ID NO 10
<211> LENGTH: 23
<212> TYPE: DNA
<213> ORGANISM: Artificial Sequence
<220> FEATURE:
<223> OTHER INFORMATION: gRNA

<400> SEQUENCE: 10
tcttcgtgtg ctaccggtaa tgg      23

<210> SEQ ID NO 11
<211> LENGTH: 23
<212> TYPE: DNA
<213> ORGANISM: Artificial Sequence
<220> FEATURE:
<223> OTHER INFORMATION: gRNA

<400> SEQUENCE: 11
tcgtgtgcta ccggtaatgg agg      23

<210> SEQ ID NO 12
<211> LENGTH: 23
<212> TYPE: DNA
<213> ORGANISM: Artificial Sequence
<220> FEATURE:
<223> OTHER INFORMATION: gRNA

<400> SEQUENCE: 12
gcttcacgaa agtttctcca tgg      23

<210> SEQ ID NO 13
<211> LENGTH: 23
<212> TYPE: DNA
<213> ORGANISM: Artificial Sequence
<220> FEATURE:
<223> OTHER INFORMATION: gRNA

<400> SEQUENCE: 13
tctccatgga tcacaacagt tgg      23

<210> SEQ ID NO 14
<211> LENGTH: 23
<212> TYPE: DNA
<213> ORGANISM: Artificial Sequence
<220> FEATURE:
<223> OTHER INFORMATION: gRNA

<400> SEQUENCE: 14
ccatggatca caacagttgg tgg      23

<210> SEQ ID NO 15
<211> LENGTH: 23

<212> TYPE: DNA
<213> ORGANISM: Artificial Sequence
<220> FEATURE:
<223> OTHER INFORMATION: gRNA

<400> SEQUENCE: 15
gatcacaaca gttggtggta agg                                             23

<210> SEQ ID NO 16
<211> LENGTH: 23
<212> TYPE: DNA
<213> ORGANISM: Artificial Sequence
<220> FEATURE:
<223> OTHER INFORMATION: gRNA

<400> SEQUENCE: 16
actagtatga gaacctttaa agg                                             23

<210> SEQ ID NO 17
<211> LENGTH: 23
<212> TYPE: DNA
<213> ORGANISM: Artificial Sequence
<220> FEATURE:
<223> OTHER INFORMATION: gRNA

<400> SEQUENCE: 17
tttaaaggag tttctataag agg                                             23

<210> SEQ ID NO 18
<211> LENGTH: 23
<212> TYPE: DNA
<213> ORGANISM: Artificial Sequence
<220> FEATURE:
<223> OTHER INFORMATION: gRNA

<400> SEQUENCE: 18
ataagaggga gaacctttaa agg                                             23

<210> SEQ ID NO 19
<211> LENGTH: 23
<212> TYPE: DNA
<213> ORGANISM: Artificial Sequence
<220> FEATURE:
<223> OTHER INFORMATION: gRNA

<400> SEQUENCE: 19
tttcgacaag agttttgtct cgg                                             23

<210> SEQ ID NO 20
<211> LENGTH: 23
<212> TYPE: DNA
<213> ORGANISM: Artificial Sequence
<220> FEATURE:
<223> OTHER INFORMATION: gRNA

<400> SEQUENCE: 20
accctgatcc gacctccttc cgg                                             23

<210> SEQ ID NO 21
<211> LENGTH: 23
<212> TYPE: DNA
<213> ORGANISM: Artificial Sequence
<220> FEATURE:
<223> OTHER INFORMATION: gRNA

<400> SEQUENCE: 21
atgatatatc tgaagctcaa agg                                              23

<210> SEQ ID NO 22
<211> LENGTH: 300
<212> TYPE: DNA
<213> ORGANISM: Arabidopsis lyrata

<400> SEQUENCE: 22
cctttgagct tcagatatat cattatcccg gaaggaggtc ggatcagggt ttaggaaaca      60
aaacagagga aactgttgtt tgttccgaga caaaactctt gtcgaaactc ctttaaaggt     120
tctccctctt atagaaactc ctttaaaggt tctcatacta gttcttagct tcactgtcgt     180
tggaaaatct ctgtccttac caccaactgt tgtgatccat ggagaaactt tcgtgaagct     240
aaacggatca gaacctccat taccggtagc acacgaagaa accaaagctc tcatctccat     300

<210> SEQ ID NO 23
<211> LENGTH: 23
<212> TYPE: DNA
<213> ORGANISM: Artificial Sequence
<220> FEATURE:
<223> OTHER INFORMATION: gRNA

<400> SEQUENCE: 23
cttcagatat atcattatcc cgg                                              23

<210> SEQ ID NO 24
<211> LENGTH: 23
<212> TYPE: DNA
<213> ORGANISM: Artificial Sequence
<220> FEATURE:
<223> OTHER INFORMATION: gRNA

<400> SEQUENCE: 24
agatatatca ttatcccgga agg                                              23

<210> SEQ ID NO 25
<211> LENGTH: 23
<212> TYPE: DNA
<213> ORGANISM: Artificial Sequence
<220> FEATURE:
<223> OTHER INFORMATION: gRNA

<400> SEQUENCE: 25
tatatcatta tcccggaagg agg                                              23

<210> SEQ ID NO 26
<211> LENGTH: 23
<212> TYPE: DNA
<213> ORGANISM: Artificial Sequence
<220> FEATURE:
<223> OTHER INFORMATION: gRNA

<400> SEQUENCE: 26
tcattatccc ggaaggaggt cgg                                              23

<210> SEQ ID NO 27
<211> LENGTH: 23
<212> TYPE: DNA
<213> ORGANISM: Artificial Sequence
<220> FEATURE:
<223> OTHER INFORMATION: gRNA

<400> SEQUENCE: 27
tcccggaagg aggtcggatc agg                                              23

<210> SEQ ID NO 28
<211> LENGTH: 23
<212> TYPE: DNA
<213> ORGANISM: Artificial Sequence
<220> FEATURE:
<223> OTHER INFORMATION: gRNA

<400> SEQUENCE: 28
cccggaagga ggtcggatca ggg                                            23

<210> SEQ ID NO 29
<211> LENGTH: 23
<212> TYPE: DNA
<213> ORGANISM: Artificial Sequence
<220> FEATURE:
<223> OTHER INFORMATION: gRNA

<400> SEQUENCE: 29
aggaggtcgg atcagggttt agg                                            23

<210> SEQ ID NO 30
<211> LENGTH: 23
<212> TYPE: DNA
<213> ORGANISM: Artificial Sequence
<220> FEATURE:
<223> OTHER INFORMATION: gRNA

<400> SEQUENCE: 30
gggtttagga aacaaaacag agg                                            23

<210> SEQ ID NO 31
<211> LENGTH: 23
<212> TYPE: DNA
<213> ORGANISM: Artificial Sequence
<220> FEATURE:
<223> OTHER INFORMATION: gRNA

<400> SEQUENCE: 31
tcttgtcgaa actcctttaa agg                                            23

<210> SEQ ID NO 32
<211> LENGTH: 23
<212> TYPE: DNA
<213> ORGANISM: Artificial Sequence
<220> FEATURE:
<223> OTHER INFORMATION: gRNA

<400> SEQUENCE: 32
tcttatagaa actcctttaa agg                                            23

<210> SEQ ID NO 33
<211> LENGTH: 23
<212> TYPE: DNA
<213> ORGANISM: Artificial Sequence
<220> FEATURE:
<223> OTHER INFORMATION: gRNA

<400> SEQUENCE: 33
gttcttagct tcactgtcgt tgg                                            23

<210> SEQ ID NO 34
<211> LENGTH: 23
<212> TYPE: DNA
<213> ORGANISM: Artificial Sequence
<220> FEATURE:

```
<223> OTHER INFORMATION: gRNA

<400> SEQUENCE: 34
ccaccaactg ttgtgatcca tgg                                                23

<210> SEQ ID NO 35
<211> LENGTH: 23
<212> TYPE: DNA
<213> ORGANISM: Artificial Sequence
<220> FEATURE:
<223> OTHER INFORMATION: gRNA

<400> SEQUENCE: 35
gaaactttcg tgaagctaaa cgg                                                23

<210> SEQ ID NO 36
<211> LENGTH: 23
<212> TYPE: DNA
<213> ORGANISM: Artificial Sequence
<220> FEATURE:
<223> OTHER INFORMATION: gRNA

<400> SEQUENCE: 36
cggatcagaa cctccattac cgg                                                23

<210> SEQ ID NO 37
<211> LENGTH: 100
<212> TYPE: PRT
<213> ORGANISM: Cannabis sativa

<400> SEQUENCE: 37
```

Met Glu Met Arg Ala Leu Val Ser Ser Tyr Ser Thr Gly Asn Gly Gly
1               5                   10                  15

Ser Asp Pro Ile Ser Leu Thr Asn Gly Ser Pro Trp Ile Thr Thr Val
            20                  25                  30

Gly Gly Gly Ala Ser Thr Met Asp Arg Glu Phe Pro Leu Thr Val Lys
        35                  40                  45

Leu Gly Ser Ser Met Arg Ala Phe Lys Gly Val Ser Thr Thr Thr Val
    50                  55                  60

Leu Ser Arg Thr Lys Gln Gln Phe Pro Leu Val Cys Leu Ala Arg Asn
65                  70                  75                  80

Asn Ala Asn Ser Thr Asp Pro Thr Ser Phe Trp Glu Asn Asp Ile Ser
                85                  90                  95

Glu Val Gln Arg
            100

```
<210> SEQ ID NO 38
<211> LENGTH: 300
<212> TYPE: DNA
<213> ORGANISM: Cannabis sativa

<400> SEQUENCE: 38
atggagatga gagctttggt tcttcgtat tctaccggta tggaggttc tgatccgatc         60 agcctcacga atggttctcc atggatcaca acagttggtg gtggtgcaag taccatggac       120
agagagtttc cattgactgt gaagctggga agtagtatga gagccttcaa aggagtaagc       180
acaacaacag ttttgtctcg gaccaaacaa cagtttcctc tggtatgctt agcaagaaac       240
aatgcgaaca gcactgatcc gacctcgttc tgggagaatg atatatctga agttcaaagg       300

<210> SEQ ID NO 39
```

<211> LENGTH: 23
<212> TYPE: DNA
<213> ORGANISM: Artificial Sequence
<220> FEATURE:
<223> OTHER INFORMATION: gRNA

<400> SEQUENCE: 39
ttggtttctt cgtattctac cgg                                            23

<210> SEQ ID NO 40
<211> LENGTH: 23
<212> TYPE: DNA
<213> ORGANISM: Artificial Sequence
<220> FEATURE:
<223> OTHER INFORMATION: gRNA

<400> SEQUENCE: 40
tcttcgtatt ctaccggtaa tgg                                            23

<210> SEQ ID NO 41
<211> LENGTH: 23
<212> TYPE: DNA
<213> ORGANISM: Artificial Sequence
<220> FEATURE:
<223> OTHER INFORMATION: gRNA

<400> SEQUENCE: 41
tcgtattcta ccggtaatgg agg                                            23

<210> SEQ ID NO 42
<211> LENGTH: 23
<212> TYPE: DNA
<213> ORGANISM: Artificial Sequence
<220> FEATURE:
<223> OTHER INFORMATION: gRNA

<400> SEQUENCE: 42
gatccgatca gcctcacgaa tgg                                            23

<210> SEQ ID NO 43
<211> LENGTH: 23
<212> TYPE: DNA
<213> ORGANISM: Artificial Sequence
<220> FEATURE:
<223> OTHER INFORMATION: gRNA

<400> SEQUENCE: 43
gcctcacgaa tggttctcca tgg                                            23

<210> SEQ ID NO 44
<211> LENGTH: 23
<212> TYPE: DNA
<213> ORGANISM: Artificial Sequence
<220> FEATURE:
<223> OTHER INFORMATION: gRNA

<400> SEQUENCE: 44
tctccatgga tcacaacagt tgg                                            23

<210> SEQ ID NO 45
<211> LENGTH: 23
<212> TYPE: DNA
<213> ORGANISM: Artificial Sequence
<220> FEATURE:
<223> OTHER INFORMATION: gRNA

<400> SEQUENCE: 45

```
ccatggatca caacagttgg tgg                                          23
```

<210> SEQ ID NO 46
<211> LENGTH: 23
<212> TYPE: DNA
<213> ORGANISM: Artificial Sequence
<220> FEATURE:
<223> OTHER INFORMATION: gRNA

<400> SEQUENCE: 46

```
tggatcacaa cagttggtgg tgg                                          23
```

<210> SEQ ID NO 47
<211> LENGTH: 23
<212> TYPE: DNA
<213> ORGANISM: Artificial Sequence
<220> FEATURE:
<223> OTHER INFORMATION: gRNA

<400> SEQUENCE: 47

```
tggtggtggt gcaagtacca tgg                                          23
```

<210> SEQ ID NO 48
<211> LENGTH: 23
<212> TYPE: DNA
<213> ORGANISM: Artificial Sequence
<220> FEATURE:
<223> OTHER INFORMATION: gRNA

<400> SEQUENCE: 48

```
gtttccattg actgtgaagc tgg                                          23
```

<210> SEQ ID NO 49
<211> LENGTH: 23
<212> TYPE: DNA
<213> ORGANISM: Artificial Sequence
<220> FEATURE:
<223> OTHER INFORMATION: gRNA

<400> SEQUENCE: 49

```
agtagtatga gagccttcaa agg                                          23
```

<210> SEQ ID NO 50
<211> LENGTH: 23
<212> TYPE: DNA
<213> ORGANISM: Artificial Sequence
<220> FEATURE:
<223> OTHER INFORMATION: gRNA

<400> SEQUENCE: 50

```
gcacaacaac agttttgtct cgg                                          23
```

<210> SEQ ID NO 51
<211> LENGTH: 23
<212> TYPE: DNA
<213> ORGANISM: Artificial Sequence
<220> FEATURE:
<223> OTHER INFORMATION: gRNA

<400> SEQUENCE: 51

```
gaccaaacaa cagtttcctc tgg                                          23
```

<210> SEQ ID NO 52
<211> LENGTH: 23
<212> TYPE: DNA

```
<213> ORGANISM: Artificial Sequence
<220> FEATURE:
<223> OTHER INFORMATION: gRNA

<400> SEQUENCE: 52
gcactgatcc gacctcgttc tgg                                              23

<210> SEQ ID NO 53
<211> LENGTH: 23
<212> TYPE: DNA
<213> ORGANISM: Artificial Sequence
<220> FEATURE:
<223> OTHER INFORMATION: gRNA

<400> SEQUENCE: 53
atgatatatc tgaagttcaa agg                                              23

<210> SEQ ID NO 54
<211> LENGTH: 300
<212> TYPE: DNA
<213> ORGANISM: Cannabis sativa

<400> SEQUENCE: 54
cctttgaact tcagatatat cattctccca gaacgaggtc ggatcagtgc tgttcgcatt      60
gtttcttgct aagcatacca gaggaaactg ttgtttggtc cgagacaaaa ctgttgttgt     120
gcttactcct ttgaaggctc tcatactact tcccagcttc acagtcaatg gaaactctct    180
gtccatggta cttgcaccac caccaactgt tgtgatccat ggagaaccat tcgtgaggct    240
gatcggatca gaacctccat taccggtaga atacgaagaa accaaagctc tcatctccat    300

<210> SEQ ID NO 55
<211> LENGTH: 23
<212> TYPE: DNA
<213> ORGANISM: Artificial Sequence
<220> FEATURE:
<223> OTHER INFORMATION: gRNA

<400> SEQUENCE: 55
tatatcattc tcccagaacg agg                                              23

<210> SEQ ID NO 56
<211> LENGTH: 23
<212> TYPE: DNA
<213> ORGANISM: Artificial Sequence
<220> FEATURE:
<223> OTHER INFORMATION: gRNA

<400> SEQUENCE: 56
tcattctccc agaacgaggt cgg                                              23

<210> SEQ ID NO 57
<211> LENGTH: 23
<212> TYPE: DNA
<213> ORGANISM: Artificial Sequence
<220> FEATURE:
<223> OTHER INFORMATION: gRNA

<400> SEQUENCE: 57
tttcttgcta agcataccag agg                                              23

<210> SEQ ID NO 58
<211> LENGTH: 23
<212> TYPE: DNA
<213> ORGANISM: Artificial Sequence
```

```
<220> FEATURE:
<223> OTHER INFORMATION: gRNA

<400> SEQUENCE: 58
taccagagga aactgttgtt tgg                                              23

<210> SEQ ID NO 59
<211> LENGTH: 23
<212> TYPE: DNA
<213> ORGANISM: Artificial Sequence
<220> FEATURE:
<223> OTHER INFORMATION: gRNA

<400> SEQUENCE: 59
tgttgtgctt actcctttga agg                                              23

<210> SEQ ID NO 60
<211> LENGTH: 23
<212> TYPE: DNA
<213> ORGANISM: Artificial Sequence
<220> FEATURE:
<223> OTHER INFORMATION: gRNA

<400> SEQUENCE: 60
cttcccagct tcacagtcaa tgg                                              23

<210> SEQ ID NO 61
<211> LENGTH: 23
<212> TYPE: DNA
<213> ORGANISM: Artificial Sequence
<220> FEATURE:
<223> OTHER INFORMATION: gRNA

<400> SEQUENCE: 61
caatggaaac tctctgtcca tgg                                              23

<210> SEQ ID NO 62
<211> LENGTH: 23
<212> TYPE: DNA
<213> ORGANISM: Artificial Sequence
<220> FEATURE:
<223> OTHER INFORMATION: gRNA

<400> SEQUENCE: 62
ccaccaactg ttgtgatcca tgg                                              23

<210> SEQ ID NO 63
<211> LENGTH: 23
<212> TYPE: DNA
<213> ORGANISM: Artificial Sequence
<220> FEATURE:
<223> OTHER INFORMATION: gRNA

<400> SEQUENCE: 63
tccatggaga accattcgtg agg                                              23

<210> SEQ ID NO 64
<211> LENGTH: 23
<212> TYPE: DNA
<213> ORGANISM: Artificial Sequence
<220> FEATURE:
<223> OTHER INFORMATION: gRNA

<400> SEQUENCE: 64
gaaccattcg tgaggctgat cgg                                              23
```

<210> SEQ ID NO 65
<211> LENGTH: 23
<212> TYPE: DNA
<213> ORGANISM: Artificial Sequence
<220> FEATURE:
<223> OTHER INFORMATION: gRNA

<400> SEQUENCE: 65
cggatcagaa cctccattac cgg                                           23

<210> SEQ ID NO 66
<211> LENGTH: 100
<212> TYPE: PRT
<213> ORGANISM: Cannabis sativa

<400> SEQUENCE: 66

Met Glu Met Arg Ala Leu Val Ser Ser Cys Ser Thr Gly Asn Gly Gly
1               5                   10                  15

Ser Asp Pro Ile Ser Leu Thr Asn Gly Ser Pro Trp Ile Thr Thr Val
            20                  25                  30

Gly Gly Gly Ala Ser Thr Met Asp Arg Glu Phe Pro Ala Thr Val Lys
        35                  40                  45

Leu Gly Ser Ser Met Arg Ala Phe Lys Gly Val Ser Thr Ile Thr Val
    50                  55                  60

Leu Ser Arg Thr Lys Gln Gln Phe Pro Leu Val Cys Leu Ala Arg Asn
65                  70                  75                  80

Asn Gly Asn Ser Thr Asp Pro Thr Ser Phe Trp Glu Asn Asp Ile Ser
                85                  90                  95

Glu Thr Gln Arg
            100

<210> SEQ ID NO 67
<211> LENGTH: 300
<212> TYPE: DNA
<213> ORGANISM: Cannabis sativa

<400> SEQUENCE: 67
atggagatga gagctttggt tcttcgtgt tctacgggga atggagggtc tgatccgatc       60
agcctcacga atggttctcc atggatcaca acagttggtg gtggtgcaag taccatggac     120
agagagtttc cagcgactgt gaagctggga agtagtatga gagccttcaa ggagtaagc      180 acaataacag ttctgtctcg gaccaaacaa cagtttcctc tggtatgctt agcaagaaac     240
aacggaaaca gcactgatcc gacctcgttc tgggagaacg atatatctga aactcaaagg     300

<210> SEQ ID NO 68
<211> LENGTH: 23
<212> TYPE: DNA
<213> ORGANISM: Artificial Sequence
<220> FEATURE:
<223> OTHER INFORMATION: gRNA

<400> SEQUENCE: 68
tttggtttct tcgtgttcta cgg                                           23

<210> SEQ ID NO 69
<211> LENGTH: 23
<212> TYPE: DNA
<213> ORGANISM: Artificial Sequence
<220> FEATURE:
<223> OTHER INFORMATION: gRNA

```
<400> SEQUENCE: 69
ttggtttctt cgtgttctac ggg                                               23

<210> SEQ ID NO 70
<211> LENGTH: 23
<212> TYPE: DNA
<213> ORGANISM: Artificial Sequence
<220> FEATURE:
<223> OTHER INFORMATION: gRNA

<400> SEQUENCE: 70
tggtttcttc gtgttctacg ggg                                               23

<210> SEQ ID NO 71
<211> LENGTH: 23
<212> TYPE: DNA
<213> ORGANISM: Artificial Sequence
<220> FEATURE:
<223> OTHER INFORMATION: gRNA

<400> SEQUENCE: 71
tcttcgtgtt ctacggggaa tgg                                               23

<210> SEQ ID NO 72
<211> LENGTH: 23
<212> TYPE: DNA
<213> ORGANISM: Artificial Sequence
<220> FEATURE:
<223> OTHER INFORMATION: gRNA

<400> SEQUENCE: 72
tcgtgttcta cggggaatgg agg                                               23

<210> SEQ ID NO 73
<211> LENGTH: 23
<212> TYPE: DNA
<213> ORGANISM: Artificial Sequence
<220> FEATURE:
<223> OTHER INFORMATION: gRNA

<400> SEQUENCE: 73
gatccgatca gcctcacgaa tgg                                               23

<210> SEQ ID NO 74
<211> LENGTH: 23
<212> TYPE: DNA
<213> ORGANISM: Artificial Sequence
<220> FEATURE:
<223> OTHER INFORMATION: gRNA

<400> SEQUENCE: 74
gcctcacgaa tggttctcca tgg                                               23

<210> SEQ ID NO 75
<211> LENGTH: 23
<212> TYPE: DNA
<213> ORGANISM: Artificial Sequence
<220> FEATURE:
<223> OTHER INFORMATION: gRNA

<400> SEQUENCE: 75
tctccatgga tcacaacagt tgg                                               23

<210> SEQ ID NO 76
<211> LENGTH: 23
```

<212> TYPE: DNA
<213> ORGANISM: Artificial Sequence
<220> FEATURE:
<223> OTHER INFORMATION: gRNA

<400> SEQUENCE: 76
ccatggatca caacagttgg tgg                                      23

<210> SEQ ID NO 77
<211> LENGTH: 23
<212> TYPE: DNA
<213> ORGANISM: Artificial Sequence
<220> FEATURE:
<223> OTHER INFORMATION: gRNA

<400> SEQUENCE: 77
tggatcacaa cagttggtgg tgg                                      23

<210> SEQ ID NO 78
<211> LENGTH: 23
<212> TYPE: DNA
<213> ORGANISM: Artificial Sequence
<220> FEATURE:
<223> OTHER INFORMATION: gRNA

<400> SEQUENCE: 78
tggtggtggt gcaagtacca tgg                                      23

<210> SEQ ID NO 79
<211> LENGTH: 23
<212> TYPE: DNA
<213> ORGANISM: Artificial Sequence
<220> FEATURE:
<223> OTHER INFORMATION: gRNA

<400> SEQUENCE: 79
gtttccagcg actgtgaagc tgg                                      23

<210> SEQ ID NO 80
<211> LENGTH: 23
<212> TYPE: DNA
<213> ORGANISM: Artificial Sequence
<220> FEATURE:
<223> OTHER INFORMATION: gRNA

<400> SEQUENCE: 80
agtagtatga gagccttcaa agg                                      23

<210> SEQ ID NO 81
<211> LENGTH: 23
<212> TYPE: DNA
<213> ORGANISM: Artificial Sequence
<220> FEATURE:
<223> OTHER INFORMATION: gRNA

<400> SEQUENCE: 81
gcacaataac agttctgtct cgg                                      23

<210> SEQ ID NO 82
<211> LENGTH: 23
<212> TYPE: DNA
<213> ORGANISM: Artificial Sequence
<220> FEATURE:
<223> OTHER INFORMATION: gRNA

<400> SEQUENCE: 82

```
gaccaaacaa cagtttcctc tgg                                               23
```

\<210\> SEQ ID NO 83
\<211\> LENGTH: 23
\<212\> TYPE: DNA
\<213\> ORGANISM: Artificial Sequence
\<220\> FEATURE:
\<223\> OTHER INFORMATION: gRNA

\<400\> SEQUENCE: 83

```
gtatgcttag caagaaacaa cgg                                               23
```

\<210\> SEQ ID NO 84
\<211\> LENGTH: 23
\<212\> TYPE: DNA
\<213\> ORGANISM: Artificial Sequence
\<220\> FEATURE:
\<223\> OTHER INFORMATION: gRNA

\<400\> SEQUENCE: 84

```
gcactgatcc gacctcgttc tgg                                               23
```

\<210\> SEQ ID NO 85
\<211\> LENGTH: 23
\<212\> TYPE: DNA
\<213\> ORGANISM: Artificial Sequence
\<220\> FEATURE:
\<223\> OTHER INFORMATION: gRNA

\<400\> SEQUENCE: 85

```
acgatatatc tgaaactcaa agg                                               23
```

\<210\> SEQ ID NO 86
\<211\> LENGTH: 300
\<212\> TYPE: DNA
\<213\> ORGANISM: Cannabis sativa

\<400\> SEQUENCE: 86

```
cctttgagtt tcagatatat cgttctccca gaacgaggtc ggatcagtgc tgtttccgtt       60
gtttcttgct aagcatacca gaggaaactg ttgtttggtc cgagacagaa ctgttattgt      120
gcttactcct ttgaaggctc tcatactact tcccagcttc acagtcgctg gaaactctct      180
gtccatggta cttgcaccac caccaactgt tgtgatccat ggagaaccat tcgtgaggct      240
gatcggatca gaccctccat tccccgtaga acacgaagaa accaaagctc tcatctccat      300
```

\<210\> SEQ ID NO 87
\<211\> LENGTH: 23
\<212\> TYPE: DNA
\<213\> ORGANISM: Artificial Sequence
\<220\> FEATURE:
\<223\> OTHER INFORMATION: gRNA

\<400\> SEQUENCE: 87

```
tatatcgttc tcccagaacg agg                                               23
```

\<210\> SEQ ID NO 88
\<211\> LENGTH: 23
\<212\> TYPE: DNA
\<213\> ORGANISM: Artificial Sequence
\<220\> FEATURE:
\<223\> OTHER INFORMATION: gRNA

\<400\> SEQUENCE: 88

```
tcgttctccc agaacgaggt cgg                                               23
```

```
<210> SEQ ID NO 89
<211> LENGTH: 23
<212> TYPE: DNA
<213> ORGANISM: Artificial Sequence
<220> FEATURE:
<223> OTHER INFORMATION: gRNA

<400> SEQUENCE: 89
tttcttgcta agcataccag agg                                              23

<210> SEQ ID NO 90
<211> LENGTH: 23
<212> TYPE: DNA
<213> ORGANISM: Artificial Sequence
<220> FEATURE:
<223> OTHER INFORMATION: gRNA

<400> SEQUENCE: 90
taccagagga aactgttgtt tgg                                              23

<210> SEQ ID NO 91
<211> LENGTH: 23
<212> TYPE: DNA
<213> ORGANISM: Artificial Sequence
<220> FEATURE:
<223> OTHER INFORMATION: gRNA

<400> SEQUENCE: 91
tattgtgctt actcctttga agg                                              23

<210> SEQ ID NO 92
<211> LENGTH: 23
<212> TYPE: DNA
<213> ORGANISM: Artificial Sequence
<220> FEATURE:
<223> OTHER INFORMATION: gRNA

<400> SEQUENCE: 92
cttcccagct tcacagtcgc tgg                                              23

<210> SEQ ID NO 93
<211> LENGTH: 23
<212> TYPE: DNA
<213> ORGANISM: Artificial Sequence
<220> FEATURE:
<223> OTHER INFORMATION: gRNA

<400> SEQUENCE: 93
cgctggaaac tctctgtcca tgg                                              23

<210> SEQ ID NO 94
<211> LENGTH: 23
<212> TYPE: DNA
<213> ORGANISM: Artificial Sequence
<220> FEATURE:
<223> OTHER INFORMATION: gRNA

<400> SEQUENCE: 94
ccaccaactg ttgtgatcca tgg                                              23

<210> SEQ ID NO 95
<211> LENGTH: 23
<212> TYPE: DNA
<213> ORGANISM: Artificial Sequence
<220> FEATURE:
```

<223> OTHER INFORMATION: gRNA

<400> SEQUENCE: 95
tccatggaga accattcgtg agg    23

<210> SEQ ID NO 96
<211> LENGTH: 23
<212> TYPE: DNA
<213> ORGANISM: Artificial Sequence
<220> FEATURE:
<223> OTHER INFORMATION: gRNA

<400> SEQUENCE: 96
gaaccattcg tgaggctgat cgg    23

<210> SEQ ID NO 97
<211> LENGTH: 100
<212> TYPE: PRT
<213> ORGANISM: Capsella rubella

<400> SEQUENCE: 97

Met Glu Met Arg Ala Leu Val Ser Ser Cys Ser Thr Gly Asn Gly Gly
1               5                   10                  15

Ser Asp Pro Ile Ser Leu Thr Asn Val Ser Pro Trp Ile Thr Thr Val
            20                  25                  30

Gly Gly Gly Ala Ser Ser Ile Asp Arg Glu Phe Pro Thr Thr Val Lys
        35                  40                  45

Leu Gly Ser Ser Leu Arg Thr Phe Lys Gly Val Ser Ser Thr Thr Val
    50                  55                  60

Leu Ser Arg Thr Lys Gln Gln Phe Pro Leu Val Cys Leu Ala Arg Asn
65                  70                  75                  80

Asn Ala Asn Ser Thr Asp Pro Thr Leu Phe Trp Glu Asn Asp Ile Ser
                85                  90                  95

Glu Ala Gln Ser
            100

<210> SEQ ID NO 98
<211> LENGTH: 300
<212> TYPE: DNA
<213> ORGANISM: Capsella rubella

<400> SEQUENCE: 98
atggagatga gagctttggt ttcttcgtgt tctaccggta atggaggttc tgatccgatt    60
agcctcacga atgtttctcc atggatcaca acagttggtg gtggtgcaag ttccattgac    120
agagagtttc caacgactgt gaagctggga agtagtctga aactttcaa aggagtaagc    180 tctacgacag ttttgtctcg gaccaaacaa cagtttcctc tggtttgttt agcaagaaac    240
aatgccaaca gcactgatcc aaccttgttc tgggaaaatg acatatctga agctcaaagc    300

<210> SEQ ID NO 99
<211> LENGTH: 23
<212> TYPE: DNA
<213> ORGANISM: Artificial Sequence
<220> FEATURE:
<223> OTHER INFORMATION: gRNA

<400> SEQUENCE: 99
ttggtttctt cgtgttctac cgg    23

<210> SEQ ID NO 100

```
<211> LENGTH: 23
<212> TYPE: DNA
<213> ORGANISM: Artificial Sequence
<220> FEATURE:
<223> OTHER INFORMATION: gRNA

<400> SEQUENCE: 100
tcttcgtgtt ctaccggtaa tgg                                              23

<210> SEQ ID NO 101
<211> LENGTH: 23
<212> TYPE: DNA
<213> ORGANISM: Artificial Sequence
<220> FEATURE:
<223> OTHER INFORMATION: gRNA

<400> SEQUENCE: 101
tcgtgttcta ccggtaatgg agg                                              23

<210> SEQ ID NO 102
<211> LENGTH: 23
<212> TYPE: DNA
<213> ORGANISM: Artificial Sequence
<220> FEATURE:
<223> OTHER INFORMATION: gRNA

<400> SEQUENCE: 102
gcctcacgaa tgtttctcca tgg                                              23

<210> SEQ ID NO 103
<211> LENGTH: 23
<212> TYPE: DNA
<213> ORGANISM: Artificial Sequence
<220> FEATURE:
<223> OTHER INFORMATION: gRNA

<400> SEQUENCE: 103
tctccatgga tcacaacagt tgg                                              23

<210> SEQ ID NO 104
<211> LENGTH: 23
<212> TYPE: DNA
<213> ORGANISM: Artificial Sequence
<220> FEATURE:
<223> OTHER INFORMATION: gRNA

<400> SEQUENCE: 104
ccatggatca caacagttgg tgg                                              23

<210> SEQ ID NO 105
<211> LENGTH: 23
<212> TYPE: DNA
<213> ORGANISM: Artificial Sequence
<220> FEATURE:
<223> OTHER INFORMATION: gRNA

<400> SEQUENCE: 105
gtttccaacg actgtgaagc tgg                                              23

<210> SEQ ID NO 106
<211> LENGTH: 23
<212> TYPE: DNA
<213> ORGANISM: Artificial Sequence
<220> FEATURE:
<223> OTHER INFORMATION: gRNA

<400> SEQUENCE: 106
```

```
agtagtctga aactttcaa agg                                             23

<210> SEQ ID NO 107
<211> LENGTH: 23
<212> TYPE: DNA
<213> ORGANISM: Artificial Sequence
<220> FEATURE:
<223> OTHER INFORMATION: gRNA

<400> SEQUENCE: 107
gctctacgac agttttgtct cgg                                            23

<210> SEQ ID NO 108
<211> LENGTH: 23
<212> TYPE: DNA
<213> ORGANISM: Artificial Sequence
<220> FEATURE:
<223> OTHER INFORMATION: gRNA

<400> SEQUENCE: 108
gaccaaacaa cagtttcctc tgg                                            23

<210> SEQ ID NO 109
<211> LENGTH: 23
<212> TYPE: DNA
<213> ORGANISM: Artificial Sequence
<220> FEATURE:
<223> OTHER INFORMATION: gRNA

<400> SEQUENCE: 109
gcactgatcc aaccttgttc tgg                                            23

<210> SEQ ID NO 110
<211> LENGTH: 300
<212> TYPE: DNA
<213> ORGANISM: Capsella rubella

<400> SEQUENCE: 110
gctttgagct tcagatatgt cattttccca gaacaaggtt ggatcagtgc tgttggcatt    60
gtttcttgct aaacaaacca gaggaaactg ttgtttggtc cgagacaaaa ctgtcgtaga   120
gcttactcct ttgaaagttc tcagactact tcccagcttc acagtcgttg gaaactctct   180
gtcaatggaa cttgcaccac caccaactgt tgtgatccat ggagaaacat tcgtgaggct   240
aatcggatca gaacctccat taccggtaga acacgaagaa accaaagctc tcatctccat   300

<210> SEQ ID NO 111
<211> LENGTH: 23
<212> TYPE: DNA
<213> ORGANISM: Artificial Sequence
<220> FEATURE:
<223> OTHER INFORMATION: gRNA

<400> SEQUENCE: 111
tatgtcattt tcccagaaca agg                                            23

<210> SEQ ID NO 112
<211> LENGTH: 23
<212> TYPE: DNA
<213> ORGANISM: Artificial Sequence
<220> FEATURE:
<223> OTHER INFORMATION: gRNA

<400> SEQUENCE: 112
```

```
tcattttccc agaacaaggt tgg                                              23

<210> SEQ ID NO 113
<211> LENGTH: 23
<212> TYPE: DNA
<213> ORGANISM: Artificial Sequence
<220> FEATURE:
<223> OTHER INFORMATION: gRNA

<400> SEQUENCE: 113
caaggttgga tcagtgctgt tgg                                              23

<210> SEQ ID NO 114
<211> LENGTH: 23
<212> TYPE: DNA
<213> ORGANISM: Artificial Sequence
<220> FEATURE:
<223> OTHER INFORMATION: gRNA

<400> SEQUENCE: 114
tttcttgcta aacaaaccag agg                                              23

<210> SEQ ID NO 115
<211> LENGTH: 23
<212> TYPE: DNA
<213> ORGANISM: Artificial Sequence
<220> FEATURE:
<223> OTHER INFORMATION: gRNA

<400> SEQUENCE: 115
aaccagagga aactgttgtt tgg                                              23

<210> SEQ ID NO 116
<211> LENGTH: 23
<212> TYPE: DNA
<213> ORGANISM: Artificial Sequence
<220> FEATURE:
<223> OTHER INFORMATION: gRNA

<400> SEQUENCE: 116
cttcccagct tcacagtcgt tgg                                              23

<210> SEQ ID NO 117
<211> LENGTH: 23
<212> TYPE: DNA
<213> ORGANISM: Artificial Sequence
<220> FEATURE:
<223> OTHER INFORMATION: gRNA

<400> SEQUENCE: 117
cgttggaaac tctctgtcaa tgg                                              23

<210> SEQ ID NO 118
<211> LENGTH: 23
<212> TYPE: DNA
<213> ORGANISM: Artificial Sequence
<220> FEATURE:
<223> OTHER INFORMATION: gRNA

<400> SEQUENCE: 118
ccaccaactg ttgtgatcca tgg                                              23

<210> SEQ ID NO 119
<211> LENGTH: 23
<212> TYPE: DNA
<213> ORGANISM: Artificial Sequence
```

```
<220> FEATURE:
<223> OTHER INFORMATION: gRNA

<400> SEQUENCE: 119
tccatggaga aacattcgtg agg                                               23

<210> SEQ ID NO 120
<211> LENGTH: 23
<212> TYPE: DNA
<213> ORGANISM: Artificial Sequence
<220> FEATURE:
<223> OTHER INFORMATION: gRNA

<400> SEQUENCE: 120
gaaacattcg tgaggctaat cgg                                               23

<210> SEQ ID NO 121
<211> LENGTH: 23
<212> TYPE: DNA
<213> ORGANISM: Artificial Sequence
<220> FEATURE:
<223> OTHER INFORMATION: gRNA

<400> SEQUENCE: 121
cggatcagaa cctccattac cgg                                               23

<210> SEQ ID NO 122
<211> LENGTH: 100
<212> TYPE: PRT
<213> ORGANISM: Brassica oleracea

<400> SEQUENCE: 122

Met Glu Met Arg Ala Leu Val Ser Cys Ser Ala Ala Gly Asn Gly Ala
1               5                   10                  15

Ser Asp Arg Phe Arg Leu Ser Asn Val Ser Pro Trp Ile Thr Ser Ala
                20                  25                  30

Arg Gly Ala Ser Gly Ser Asp Ser Pro Ala Thr Val Lys Leu Arg Ser
            35                  40                  45

Ser Ser Met Ile Arg Ala Phe Lys Gly Val Ser Ile Tyr Lys Asn Lys
        50                  55                  60

Thr Arg Arg Asn Val Leu Ser Gln Arg Asn Lys Gln Phe Arg Pro Met
65                  70                  75                  80

Ala Tyr Leu Gly Arg Lys Asp Leu Ser Ser Pro Asp Pro Thr Ser Phe
                85                  90                  95

Cys Asp Asn Asp
            100

<210> SEQ ID NO 123
<211> LENGTH: 300
<212> TYPE: DNA
<213> ORGANISM: Brassica oleracea

<400> SEQUENCE: 123
atggagatga gagctttggt ttcgtgttct gctgccggaa atggagcttc tgatcggttt       60
agactctcca tgtttcacc atggatcaca tctgctcgtg gtgcaagtgg cagtgactcc      120
ccagccacag tgaagctgag aagcagctct atgattagag ctttcaaagg agtttcgatt     180
tacaaaaaca agaccagaag aaatgttctg tctcaaagga caaacagtt ccgtcctatg      240 gcctacttag gaaggaagga cttgagcagc cctgatccga cctccttctg cgataatgat     300
```

<210> SEQ ID NO 124
<211> LENGTH: 23
<212> TYPE: DNA
<213> ORGANISM: Artificial Sequence
<220> FEATURE:
<223> OTHER INFORMATION: gRNA

<400> SEQUENCE: 124
ttggtttcgt gttctgctgc cgg                                           23

<210> SEQ ID NO 125
<211> LENGTH: 23
<212> TYPE: DNA
<213> ORGANISM: Artificial Sequence
<220> FEATURE:
<223> OTHER INFORMATION: gRNA

<400> SEQUENCE: 125
tcgtgttctg ctgccggaaa tgg                                           23

<210> SEQ ID NO 126
<211> LENGTH: 23
<212> TYPE: DNA
<213> ORGANISM: Artificial Sequence
<220> FEATURE:
<223> OTHER INFORMATION: gRNA

<400> SEQUENCE: 126
ccggaaatgg agcttctgat cgg                                           23

<210> SEQ ID NO 127
<211> LENGTH: 23
<212> TYPE: DNA
<213> ORGANISM: Artificial Sequence
<220> FEATURE:
<223> OTHER INFORMATION: gRNA

<400> SEQUENCE: 127
gactctccaa tgtttcacca tgg                                           23

<210> SEQ ID NO 128
<211> LENGTH: 23
<212> TYPE: DNA
<213> ORGANISM: Artificial Sequence
<220> FEATURE:
<223> OTHER INFORMATION: gRNA

<400> SEQUENCE: 128
ccatggatca catctgctcg tgg                                           23

<210> SEQ ID NO 129
<211> LENGTH: 23
<212> TYPE: DNA
<213> ORGANISM: Artificial Sequence
<220> FEATURE:
<223> OTHER INFORMATION: gRNA

<400> SEQUENCE: 129
acatctgctc gtggtgcaag tgg                                           23

<210> SEQ ID NO 130
<211> LENGTH: 23
<212> TYPE: DNA
<213> ORGANISM: Artificial Sequence
<220> FEATURE:
<223> OTHER INFORMATION: gRNA

```
<400> SEQUENCE: 130
tctatgatta gagctttcaa agg                                              23

<210> SEQ ID NO 131
<211> LENGTH: 23
<212> TYPE: DNA
<213> ORGANISM: Artificial Sequence
<220> FEATURE:
<223> OTHER INFORMATION: gRNA

<400> SEQUENCE: 131
gaagaaatgt tctgtctcaa agg                                              23

<210> SEQ ID NO 132
<211> LENGTH: 23
<212> TYPE: DNA
<213> ORGANISM: Artificial Sequence
<220> FEATURE:
<223> OTHER INFORMATION: gRNA

<400> SEQUENCE: 132
gaacaaacag ttccgtccta tgg                                              23

<210> SEQ ID NO 133
<211> LENGTH: 23
<212> TYPE: DNA
<213> ORGANISM: Artificial Sequence
<220> FEATURE:
<223> OTHER INFORMATION: gRNA

<400> SEQUENCE: 133
ttccgtccta tggcctactt agg                                              23

<210> SEQ ID NO 134
<211> LENGTH: 23
<212> TYPE: DNA
<213> ORGANISM: Artificial Sequence
<220> FEATURE:
<223> OTHER INFORMATION: gRNA

<400> SEQUENCE: 134
gtcctatggc ctacttagga agg                                              23

<210> SEQ ID NO 135
<211> LENGTH: 23
<212> TYPE: DNA
<213> ORGANISM: Artificial Sequence
<220> FEATURE:
<223> OTHER INFORMATION: gRNA

<400> SEQUENCE: 135
tatggcctac ttaggaagga agg                                              23

<210> SEQ ID NO 136
<211> LENGTH: 300
<212> TYPE: DNA
<213> ORGANISM: Brassica oleracea

<400> SEQUENCE: 136
atcattatcg cagaaggagg tcggatcagg gctgctcaag tccttccttc ctaagtaggc      60
cataggacgg aactgtttgt tcctttgaga cagaacattt cttctggtct tgttttttgta    120 aatcgaaact cctttgaaag ctctaatcat agagctgctt ctcagcttca ctgtggctgg    180
ggagtcactg ccacttgcac cacgagcaga tgtgatccat ggtgaaacat tggagagtct    240
```

```
aaaccgatca gaagctccat ttccggcagc agaacacgaa accaaagctc tcatctccat    300
```

<210> SEQ ID NO 137
<211> LENGTH: 23
<212> TYPE: DNA
<213> ORGANISM: Artificial Sequence
<220> FEATURE:
<223> OTHER INFORMATION: gRNA

<400> SEQUENCE: 137

```
tcattatcgc agaaggaggt cgg                                             23
```

<210> SEQ ID NO 138
<211> LENGTH: 23
<212> TYPE: DNA
<213> ORGANISM: Artificial Sequence
<220> FEATURE:
<223> OTHER INFORMATION: gRNA

<400> SEQUENCE: 138

```
tcgcagaagg aggtcggatc agg                                             23
```

<210> SEQ ID NO 139
<211> LENGTH: 23
<212> TYPE: DNA
<213> ORGANISM: Artificial Sequence
<220> FEATURE:
<223> OTHER INFORMATION: gRNA

<400> SEQUENCE: 139

```
caagtccttc cttcctaagt agg                                             23
```

<210> SEQ ID NO 140
<211> LENGTH: 23
<212> TYPE: DNA
<213> ORGANISM: Artificial Sequence
<220> FEATURE:
<223> OTHER INFORMATION: gRNA

<400> SEQUENCE: 140

```
ttccttccta agtaggccat agg                                             23
```

<210> SEQ ID NO 141
<211> LENGTH: 23
<212> TYPE: DNA
<213> ORGANISM: Artificial Sequence
<220> FEATURE:
<223> OTHER INFORMATION: gRNA

<400> SEQUENCE: 141

```
ttcctaagta ggccatagga cgg                                             23
```

<210> SEQ ID NO 142
<211> LENGTH: 23
<212> TYPE: DNA
<213> ORGANISM: Artificial Sequence
<220> FEATURE:
<223> OTHER INFORMATION: gRNA

<400> SEQUENCE: 142

```
tggatcacaa cagttggtgg tgg                                             23
```

<210> SEQ ID NO 143
<211> LENGTH: 23
<212> TYPE: DNA

```
<213> ORGANISM: Artificial Sequence
<220> FEATURE:
<223> OTHER INFORMATION: gRNA

<400> SEQUENCE: 143
ttgagacaga acatttcttc tgg                                              23

<210> SEQ ID NO 144
<211> LENGTH: 23
<212> TYPE: DNA
<213> ORGANISM: Artificial Sequence
<220> FEATURE:
<223> OTHER INFORMATION: gRNA

<400> SEQUENCE: 144
gctgcttctc agcttcactg tgg                                              23

<210> SEQ ID NO 145
<211> LENGTH: 23
<212> TYPE: DNA
<213> ORGANISM: Artificial Sequence
<220> FEATURE:
<223> OTHER INFORMATION: gRNA

<400> SEQUENCE: 145
cttctcagct tcactgtggc tgg                                              23

<210> SEQ ID NO 146
<211> LENGTH: 23
<212> TYPE: DNA
<213> ORGANISM: Artificial Sequence
<220> FEATURE:
<223> OTHER INFORMATION: gRNA

<400> SEQUENCE: 146
ttctcagctt cactgtggct ggg                                              23

<210> SEQ ID NO 147
<211> LENGTH: 23
<212> TYPE: DNA
<213> ORGANISM: Artificial Sequence
<220> FEATURE:
<223> OTHER INFORMATION: gRNA

<400> SEQUENCE: 147
tctcagcttc actgtggctg ggg                                              23

<210> SEQ ID NO 148
<211> LENGTH: 23
<212> TYPE: DNA
<213> ORGANISM: Artificial Sequence
<220> FEATURE:
<223> OTHER INFORMATION: gRNA

<400> SEQUENCE: 148
ccacgagcag atgtgatcca tgg                                              23

<210> SEQ ID NO 149
<211> LENGTH: 23
<212> TYPE: DNA
<213> ORGANISM: Artificial Sequence
<220> FEATURE:
<223> OTHER INFORMATION: gRNA

<400> SEQUENCE: 149
tgtgatccat ggtgaaacat tgg                                              23
```

<210> SEQ ID NO 150
<211> LENGTH: 23
<212> TYPE: DNA
<213> ORGANISM: Artificial Sequence
<220> FEATURE:
<223> OTHER INFORMATION: gRNA

<400> SEQUENCE: 150
ccgatcagaa gctccatttc cgg                                              23

<210> SEQ ID NO 151
<211> LENGTH: 371
<212> TYPE: PRT
<213> ORGANISM: Brassica napus

<400> SEQUENCE: 151

Met Glu Met Arg Ala Leu Val Ser Cys Ser Ala Ala Gly Asn Gly Ala
1               5                   10                  15

Ser Asp Arg Phe Arg Leu Ser Asn Val Ser Pro Trp Ile Thr Ser Ala
                20                  25                  30

Arg Gly Ala Ser Gly Ser Asp Ser Pro Ala Thr Val Lys Leu Gly Ser
            35                  40                  45

Ser Ser Met Ile Arg Ala Phe Lys Gly Val Ser Ile Tyr Lys Asn Lys
        50                  55                  60

Thr Arg Arg Asn Val Leu Ser Gln Arg Asn Lys Gln Phe Arg Pro Met
65                  70                  75                  80

Ala Tyr Leu Gly Arg Lys Asp Leu Ser Ser Pro Asp Pro Thr Ser Phe
                85                  90                  95

Cys Asp Asn Asp Ile Ser Glu Pro Gln Gly Thr Gly Ser Ile Asn Gly
            100                 105                 110

Asn Asp His Ser Ala Val Arg Val Ser Gln Val Asp Glu Phe Cys Lys
        115                 120                 125

Ala His Gly Gly Lys Arg Pro Ile His Ser Ile Leu Val Ala Thr Asn
    130                 135                 140

Gly Met Ala Ala Val Lys Leu Ile Arg Ser Val Arg Ala Trp Ser Tyr
145                 150                 155                 160

Gln Thr Phe Gly Ser Glu Lys Ser Ile Ser Leu Val Ala Met Ala Thr
                165                 170                 175

Pro Glu Asp Met Arg Ile Asn Ala Glu His Ile Arg Ile Ala Asp Gln
            180                 185                 190

Phe Met Gln Val Pro Gly Gly Thr Asn Asn Asn Tyr Ala Asn Val
        195                 200                 205

His Leu Ile Val Glu Met Ala Gln Ala Thr Gly Val Asp Ala Val Trp
    210                 215                 220

Pro Gly Trp Gly His Ala Ser Glu Asn Pro Glu Leu Pro Asp Ala Leu
225                 230                 235                 240

Lys Ala Lys Gly Val Ile Phe Leu Gly Pro Thr Ala Ala Ser Met Leu
                245                 250                 255

Ala Leu Gly Asp Lys Ile Gly Ser Ser Leu Ile Ala Gln Ala Ala Asp
            260                 265                 270

Val Pro Thr Leu Pro Trp Ser Gly Ser His Val Lys Ile Pro Pro Gly
        275                 280                 285

Ser Ser Met Val Thr Ile Pro Glu Glu Met Tyr Arg Gln Ala Cys Val
    290                 295                 300

Tyr Thr Thr Glu Glu Ala Val Ala Ser Cys Gln Val Val Gly Tyr Pro

```
            305                 310                 315                 320
Ala Met Ile Lys Ala Ser Trp Gly Gly Gly Lys Gly Ile Arg Glu
                325                 330                 335

Val His Asp Asp Glu Val Arg Thr Leu Phe Lys Gln Val Gln Gly
                340                 345                 350

Glu Val Pro Gly Ser Pro Ile Phe Ile Met Lys Val Ala Ser Gln Ser
                355                 360                 365

Arg His Leu
    370

<210> SEQ ID NO 152
<211> LENGTH: 298
<212> TYPE: DNA
<213> ORGANISM: Brassica napus

<400> SEQUENCE: 152
atggagatga gagctttagt ttcgtgttct gctgccggaa atggagcttc tgatcggttt      60
agactctcca atgtttcacc atggatcaca tcagctcgtg gtgcaagtgg cagtgactcc    120
ccagccacag tgaagctggg aagcagctct atgattagag cttttcaaagg cgtttcgatt   180 tacaaaaaca agaccagaag gaatgttctg tctcaaagga caaaacagtt ccgtcctatg    240
gcctacttag gaaggaagga cttgagcagc cctgatccga cctccttctg cgataatg     298

<210> SEQ ID NO 153
<211> LENGTH: 23
<212> TYPE: DNA
<213> ORGANISM: Artificial Sequence
<220> FEATURE:
<223> OTHER INFORMATION: gRNA

<400> SEQUENCE: 153
ttagtttcgt gttctgctgc cgg                                             23

<210> SEQ ID NO 154
<211> LENGTH: 23
<212> TYPE: DNA
<213> ORGANISM: Artificial Sequence
<220> FEATURE:
<223> OTHER INFORMATION: gRNA

<400> SEQUENCE: 154
tcgtgttctg ctgccggaaa tgg                                             23

<210> SEQ ID NO 155
<211> LENGTH: 23
<212> TYPE: DNA
<213> ORGANISM: Artificial Sequence
<220> FEATURE:
<223> OTHER INFORMATION: gRNA

<400> SEQUENCE: 155
ccggaaatgg agcttctgat cgg                                             23

<210> SEQ ID NO 156
<211> LENGTH: 23
<212> TYPE: DNA
<213> ORGANISM: Artificial Sequence
<220> FEATURE:
<223> OTHER INFORMATION: gRNA

<400> SEQUENCE: 156
gactctccaa tgtttcacca tgg                                             23
```

```
<210> SEQ ID NO 157
<211> LENGTH: 23
<212> TYPE: DNA
<213> ORGANISM: Artificial Sequence
<220> FEATURE:
<223> OTHER INFORMATION: gRNA

<400> SEQUENCE: 157
ccatggatca catcagctcg tgg                                              23

<210> SEQ ID NO 158
<211> LENGTH: 23
<212> TYPE: DNA
<213> ORGANISM: Artificial Sequence
<220> FEATURE:
<223> OTHER INFORMATION: gRNA

<400> SEQUENCE: 158
acatcagctc gtggtgcaag tgg                                              23

<210> SEQ ID NO 159
<211> LENGTH: 23
<212> TYPE: DNA
<213> ORGANISM: Artificial Sequence
<220> FEATURE:
<223> OTHER INFORMATION: gRNA

<400> SEQUENCE: 159
ctccccagcc acagtgaagc tgg                                              23

<210> SEQ ID NO 160
<211> LENGTH: 23
<212> TYPE: DNA
<213> ORGANISM: Artificial Sequence
<220> FEATURE:
<223> OTHER INFORMATION: gRNA

<400> SEQUENCE: 160
tccccagcca cagtgaagct ggg                                              23

<210> SEQ ID NO 161
<211> LENGTH: 23
<212> TYPE: DNA
<213> ORGANISM: Artificial Sequence
<220> FEATURE:
<223> OTHER INFORMATION: gRNA

<400> SEQUENCE: 161
tctatgatta gagctttcaa agg                                              23

<210> SEQ ID NO 162
<211> LENGTH: 23
<212> TYPE: DNA
<213> ORGANISM: Artificial Sequence
<220> FEATURE:
<223> OTHER INFORMATION: gRNA

<400> SEQUENCE: 162
tttacaaaaa caagaccaga agg                                              23

<210> SEQ ID NO 163
<211> LENGTH: 23
<212> TYPE: DNA
<213> ORGANISM: Artificial Sequence
<220> FEATURE:
```

<223> OTHER INFORMATION: gRNA

<400> SEQUENCE: 163
gaaggaatgt tctgtctcaa agg                                              23

<210> SEQ ID NO 164
<211> LENGTH: 23
<212> TYPE: DNA
<213> ORGANISM: Artificial Sequence
<220> FEATURE:
<223> OTHER INFORMATION: gRNA

<400> SEQUENCE: 164
gaacaaacag ttccgtccta tgg                                              23

<210> SEQ ID NO 165
<211> LENGTH: 23
<212> TYPE: DNA
<213> ORGANISM: Artificial Sequence
<220> FEATURE:
<223> OTHER INFORMATION: gRNA

<400> SEQUENCE: 165
ttccgtccta tggcctactt agg                                              23

<210> SEQ ID NO 166
<211> LENGTH: 23
<212> TYPE: DNA
<213> ORGANISM: Artificial Sequence
<220> FEATURE:
<223> OTHER INFORMATION: gRNA

<400> SEQUENCE: 166
gtcctatggc ctacttagga agg                                              23

<210> SEQ ID NO 167
<211> LENGTH: 23
<212> TYPE: DNA
<213> ORGANISM: Artificial Sequence
<220> FEATURE:
<223> OTHER INFORMATION: gRNA

<400> SEQUENCE: 167
tatggcctac ttaggaagga agg                                              23

<210> SEQ ID NO 168
<211> LENGTH: 298
<212> TYPE: DNA
<213> ORGANISM: Brassica napus

<400> SEQUENCE: 168
cattatcgca gaaggaggtc ggatcagggc tgctcaagtc cttccttcct aagtaggcca     60
taggacggaa ctgtttgttc ctttgagaca gaacattcct tctggtcttg ttttgtaaa    120 tcgaaacgcc tttgaaagct ctaatcatag agctgcttcc cagcttcact gtggctgggg   180
agtcactgcc acttgcacca cgagctgatg tgatccatgg tgaaacattg gagagtctaa   240
accgatcaga agctccattt ccggcagcag aacacgaaac taaagctctc atctccat     298

<210> SEQ ID NO 169
<211> LENGTH: 23
<212> TYPE: DNA
<213> ORGANISM: Artificial Sequence
<220> FEATURE:
<223> OTHER INFORMATION: gRNA

```
<400> SEQUENCE: 169
tcgcagaagg aggtcggatc agg                                              23

<210> SEQ ID NO 170
<211> LENGTH: 23
<212> TYPE: DNA
<213> ORGANISM: Artificial Sequence
<220> FEATURE:
<223> OTHER INFORMATION: gRNA

<400> SEQUENCE: 170
cgcagaagga ggtcggatca ggg                                              23

<210> SEQ ID NO 171
<211> LENGTH: 23
<212> TYPE: DNA
<213> ORGANISM: Artificial Sequence
<220> FEATURE:
<223> OTHER INFORMATION: gRNA

<400> SEQUENCE: 171
caagtccttc cttcctaagt agg                                              23

<210> SEQ ID NO 172
<211> LENGTH: 23
<212> TYPE: DNA
<213> ORGANISM: Artificial Sequence
<220> FEATURE:
<223> OTHER INFORMATION: gRNA

<400> SEQUENCE: 172
ttccttccta agtaggccat agg                                              23

<210> SEQ ID NO 173
<211> LENGTH: 23
<212> TYPE: DNA
<213> ORGANISM: Artificial Sequence
<220> FEATURE:
<223> OTHER INFORMATION: gRNA

<400> SEQUENCE: 173
ttcctaagta ggccatagga cgg                                              23

<210> SEQ ID NO 174
<211> LENGTH: 23
<212> TYPE: DNA
<213> ORGANISM: Artificial Sequence
<220> FEATURE:
<223> OTHER INFORMATION: gRNA

<400> SEQUENCE: 174
ttgagacaga acattccttc tgg                                              23

<210> SEQ ID NO 175
<211> LENGTH: 23
<212> TYPE: DNA
<213> ORGANISM: Artificial Sequence
<220> FEATURE:
<223> OTHER INFORMATION: gRNA

<400> SEQUENCE: 175
cttcccagct tcactgtggc tgg                                              23

<210> SEQ ID NO 176
```

```
<210> SEQ ID NO 176
<211> LENGTH: 23
<212> TYPE: DNA
<213> ORGANISM: Artificial Sequence
<220> FEATURE:
<223> OTHER INFORMATION: gRNA

<400> SEQUENCE: 176
ttcccagctt cactgtggct ggg                                           23

<210> SEQ ID NO 177
<211> LENGTH: 23
<212> TYPE: DNA
<213> ORGANISM: Artificial Sequence
<220> FEATURE:
<223> OTHER INFORMATION: gRNA

<400> SEQUENCE: 177
tcccagcttc actgtggctg ggg                                           23

<210> SEQ ID NO 178
<211> LENGTH: 23
<212> TYPE: DNA
<213> ORGANISM: Artificial Sequence
<220> FEATURE:
<223> OTHER INFORMATION: gRNA

<400> SEQUENCE: 178
ccacgagctg atgtgatcca tgg                                           23

<210> SEQ ID NO 179
<211> LENGTH: 23
<212> TYPE: DNA
<213> ORGANISM: Artificial Sequence
<220> FEATURE:
<223> OTHER INFORMATION: gRNA

<400> SEQUENCE: 179
tgtgatccat ggtgaaacat tgg                                           23

<210> SEQ ID NO 180
<211> LENGTH: 23
<212> TYPE: DNA
<213> ORGANISM: Artificial Sequence
<220> FEATURE:
<223> OTHER INFORMATION: gRNA

<400> SEQUENCE: 180
ccgatcagaa gctccatttc cgg                                           23

<210> SEQ ID NO 181
<211> LENGTH: 455
<212> TYPE: PRT
<213> ORGANISM: Brassica napus

<400> SEQUENCE: 181

Met Glu Met Arg Ala Leu Val Ser Cys Ser Ala Gly Asn Gly Ala
1               5                   10                  15

Ser Asp Arg Phe Arg Leu Ser Asn Val Ser Pro Trp Ile Thr Ser Ala
                20                  25                  30

Arg Gly Ala Ser Gly Ser Asp Ser Pro Ala Thr Val Lys Leu Gly Ser
            35                  40                  45

Ser Ser Met Ile Arg Ala Phe Lys Gly Val Ser Ile Tyr Lys Asn Lys
        50                  55                  60

Thr Arg Arg Asn Val Leu Ser Gln Arg Asn Lys Gln Phe Arg Pro Met
```

```
                65                  70                  75                  80
Ala Tyr Leu Gly Arg Lys Asp Leu Ser Ser Pro Asp Pro Thr Ser Phe
                    85                  90                  95

Cys Asp Asn Asp Ile Ser Glu Pro Gln Gly Thr Gly Ser Ile Asn Gly
                100                 105                 110

Asn Asp His Ser Ala Val Arg Val Ser Gln Val Asp Glu Phe Cys Lys
                115                 120                 125

Ala His Gly Gly Lys Arg Pro Ile His Arg Ile Leu Val Ala Thr Asn
130                 135                 140

Gly Met Ala Ala Val Lys Phe Ile Arg Ser Val Arg Ala Trp Ser Tyr
145                 150                 155                 160

Gln Thr Phe Gly Ser Glu Lys Ser Ile Ser Leu Val Ala Met Ala Thr
                    165                 170                 175

Pro Glu Asp Met Arg Ile Asn Ala Glu His Ile Arg Ile Ala Asp Gln
                180                 185                 190

Phe Met Gln Val Pro Gly Gly Thr Asn Asn Asn Tyr Ala Asn Val
                195                 200                 205

His Leu Ile Val Glu Met Ala Glu Ala Thr Gly Val Asp Ala Val Trp
    210                 215                 220

Pro Gly Trp Gly His Ala Ser Glu Asn Pro Glu Leu Pro Asp Ala Leu
225                 230                 235                 240

Lys Ala Lys Gly Val Ile Phe Leu Gly Pro Thr Ala Ala Ser Met Leu
                    245                 250                 255

Ala Leu Gly Asp Lys Ile Gly Ser Ser Leu Ile Ala Gln Ala Ala Asp
                260                 265                 270

Val Pro Thr Leu Pro Trp Ser Gly Ser His Val Lys Ile Pro Pro Gly
                275                 280                 285

Ser Ser Leu Val Thr Ile Pro Glu Glu Met Tyr Arg Gln Ala Cys Val
    290                 295                 300

Tyr Thr Thr Glu Glu Ala Val Ala Ser Cys Gln Val Val Gly Tyr Pro
305                 310                 315                 320

Ala Met Ile Lys Ala Ser Trp Gly Gly Gly Lys Gly Ile Arg Lys
                    325                 330                 335

Val His Asp Asp Glu Val Arg Ala Leu Phe Lys Gln Val Gln Gly
                340                 345                 350

Glu Val Pro Gly Ser Pro Ile Phe Ile Met Lys Val Ala Ser Gln Ser
                355                 360                 365

Arg His Leu Glu Val Gln Leu Leu Cys Asp Gln Tyr Gly Asn Val Ser
    370                 375                 380

Ala Leu His Ser Arg Asp Cys Ser Val Gln Arg Arg His Gln Lys Ile
385                 390                 395                 400

Ile Glu Glu Gly Pro Ile Thr Val Ala Pro Arg Asp Thr Val Lys Lys
                    405                 410                 415

Leu Glu Gln Ala Ala Arg Arg Leu Ala Lys Ser Val Asn Tyr Val Gly
                420                 425                 430

Ala Ala Thr Val Glu Phe Leu Tyr Ser Met Asp Thr Gly Asp Tyr Phe
                435                 440                 445

Phe Leu Glu Leu Asn Pro Arg
    450                 455

<210> SEQ ID NO 182
<211> LENGTH: 298
<212> TYPE: DNA
<213> ORGANISM: Brassica napus
```

<400> SEQUENCE: 182

| | | | | | |
|---|---|---|---|---|---|
| atggagatga | gagctttggt | ttcgtgttct | gctgccggaa | atggagcttc | tgatcggttt | 60
| agactctcca | atgtttcacc | atggatcaca | tcagctcgtg | gtgcaagtgg | cagtgactcc | 120
| ccagccacag | tgaagctggg | aagcagctct | atgatcagag | ccttcaaagg | agtttcgatt | 180
| tacaaaaaca | agaccagaag | aaatgttttg | tctcaaagga | acaaacagtt | tcgtcctatg | 240
| gcctacttag | gaaggaagga | cttgagcagc | cctgatccga | cctccttctg | cgataatg | 298

<210> SEQ ID NO 183
<211> LENGTH: 23
<212> TYPE: DNA
<213> ORGANISM: Artificial Sequence
<220> FEATURE:
<223> OTHER INFORMATION: gRNA

<400> SEQUENCE: 183
ttggtttcgt gttctgctgc cgg         23

<210> SEQ ID NO 184
<211> LENGTH: 23
<212> TYPE: DNA
<213> ORGANISM: Artificial Sequence
<220> FEATURE:
<223> OTHER INFORMATION: gRNA

<400> SEQUENCE: 184
tcgtgttctg ctgccggaaa tgg         23

<210> SEQ ID NO 185
<211> LENGTH: 23
<212> TYPE: DNA
<213> ORGANISM: Artificial Sequence
<220> FEATURE:
<223> OTHER INFORMATION: gRNA

<400> SEQUENCE: 185
ccggaaatgg agcttctgat cgg         23

<210> SEQ ID NO 186
<211> LENGTH: 23
<212> TYPE: DNA
<213> ORGANISM: Artificial Sequence
<220> FEATURE:
<223> OTHER INFORMATION: gRNA

<400> SEQUENCE: 186
gactctccaa tgtttcacca tgg         23

<210> SEQ ID NO 187
<211> LENGTH: 23
<212> TYPE: DNA
<213> ORGANISM: Artificial Sequence
<220> FEATURE:
<223> OTHER INFORMATION: gRNA

<400> SEQUENCE: 187
ccatggatca catcagctcg tgg         23

<210> SEQ ID NO 188
<211> LENGTH: 23
<212> TYPE: DNA
<213> ORGANISM: Artificial Sequence
<220> FEATURE:

<223> OTHER INFORMATION: gRNA

<400> SEQUENCE: 188
acatcagctc gtggtgcaag tgg                                              23

<210> SEQ ID NO 189
<211> LENGTH: 23
<212> TYPE: DNA
<213> ORGANISM: Artificial Sequence
<220> FEATURE:
<223> OTHER INFORMATION: gRNA

<400> SEQUENCE: 189
ctccccagcc acagtgaagc tgg                                              23

<210> SEQ ID NO 190
<211> LENGTH: 23
<212> TYPE: DNA
<213> ORGANISM: Artificial Sequence
<220> FEATURE:
<223> OTHER INFORMATION: gRNA

<400> SEQUENCE: 190
tccccagcca cagtgaagct ggg                                              23

<210> SEQ ID NO 191
<211> LENGTH: 23
<212> TYPE: DNA
<213> ORGANISM: Artificial Sequence
<220> FEATURE:
<223> OTHER INFORMATION: gRNA

<400> SEQUENCE: 191
tctatgatca gagccttcaa agg                                              23

<210> SEQ ID NO 192
<211> LENGTH: 23
<212> TYPE: DNA
<213> ORGANISM: Artificial Sequence
<220> FEATURE:
<223> OTHER INFORMATION: gRNA

<400> SEQUENCE: 192
gaagaaatgt tttgtctcaa agg                                              23

<210> SEQ ID NO 193
<211> LENGTH: 23
<212> TYPE: DNA
<213> ORGANISM: Artificial Sequence
<220> FEATURE:
<223> OTHER INFORMATION: gRNA

<400> SEQUENCE: 193
gaacaaacag tttcgtccta tgg                                              23

<210> SEQ ID NO 194
<211> LENGTH: 23
<212> TYPE: DNA
<213> ORGANISM: Artificial Sequence
<220> FEATURE:
<223> OTHER INFORMATION: gRNA

<400> SEQUENCE: 194
tttcgtccta tggcctactt agg                                              23

```
<210> SEQ ID NO 195
<211> LENGTH: 23
<212> TYPE: DNA
<213> ORGANISM: Artificial Sequence
<220> FEATURE:
<223> OTHER INFORMATION: gRNA

<400> SEQUENCE: 195
gtcctatggc ctacttagga agg                                            23

<210> SEQ ID NO 196
<211> LENGTH: 23
<212> TYPE: DNA
<213> ORGANISM: Artificial Sequence
<220> FEATURE:
<223> OTHER INFORMATION: gRNA

<400> SEQUENCE: 196
tatggcctac ttaggaagga agg                                            23

<210> SEQ ID NO 197
<211> LENGTH: 298
<212> TYPE: DNA
<213> ORGANISM: Brassica napus

<400> SEQUENCE: 197
cattatcgca gaaggaggtc ggatcagggc tgctcaagtc cttccttcct aagtaggcca    60
taggacgaaa ctgtttgttc cttttgagaca aacatttct tctggtcttg ttttttgtaaa  120 tcgaaactcc tttgaaggct ctgatcatag agctgcttcc cagcttcact gtggctgggg   180
agtcactgcc acttgcacca cgagctgatg tgatccatgg tgaaacattg gagagtctaa   240
accgatcaga agctccattt ccggcagcag aacacgaaac caaagctctc atctccat     298

<210> SEQ ID NO 198
<211> LENGTH: 23
<212> TYPE: DNA
<213> ORGANISM: Artificial Sequence
<220> FEATURE:
<223> OTHER INFORMATION: gRNA

<400> SEQUENCE: 198
tcgcagaagg aggtcggatc agg                                            23

<210> SEQ ID NO 199
<211> LENGTH: 23
<212> TYPE: DNA
<213> ORGANISM: Artificial Sequence
<220> FEATURE:
<223> OTHER INFORMATION: gRNA

<400> SEQUENCE: 199
cgcagaagga ggtcggatca ggg                                            23

<210> SEQ ID NO 200
<211> LENGTH: 23
<212> TYPE: DNA
<213> ORGANISM: Artificial Sequence
<220> FEATURE:
<223> OTHER INFORMATION: gRNA

<400> SEQUENCE: 200
caagtccttc cttcctaagt agg                                            23

<210> SEQ ID NO 201
```

```
<211> LENGTH: 23
<212> TYPE: DNA
<213> ORGANISM: Artificial Sequence
<220> FEATURE:
<223> OTHER INFORMATION: gRNA

<400> SEQUENCE: 201
ttccttccta agtaggccat agg                                              23

<210> SEQ ID NO 202
<211> LENGTH: 23
<212> TYPE: DNA
<213> ORGANISM: Artificial Sequence
<220> FEATURE:
<223> OTHER INFORMATION: gRNA

<400> SEQUENCE: 202
ttgagacaaa acatttcttc tgg                                              23

<210> SEQ ID NO 203
<211> LENGTH: 23
<212> TYPE: DNA
<213> ORGANISM: Artificial Sequence
<220> FEATURE:
<223> OTHER INFORMATION: gRNA

<400> SEQUENCE: 203
gtaaatcgaa actcctttga agg                                              23

<210> SEQ ID NO 204
<211> LENGTH: 23
<212> TYPE: DNA
<213> ORGANISM: Artificial Sequence
<220> FEATURE:
<223> OTHER INFORMATION: gRNA

<400> SEQUENCE: 204
gctgcttccc agcttcactg tgg                                              23

<210> SEQ ID NO 205
<211> LENGTH: 23
<212> TYPE: DNA
<213> ORGANISM: Artificial Sequence
<220> FEATURE:
<223> OTHER INFORMATION: gRNA

<400> SEQUENCE: 205
cttcccagct tcactgtggc tgg                                              23

<210> SEQ ID NO 206
<211> LENGTH: 23
<212> TYPE: DNA
<213> ORGANISM: Artificial Sequence
<220> FEATURE:
<223> OTHER INFORMATION: gRNA

<400> SEQUENCE: 206
ttcccagctt cactgtggct ggg                                              23

<210> SEQ ID NO 207
<211> LENGTH: 23
<212> TYPE: DNA
<213> ORGANISM: Artificial Sequence
<220> FEATURE:
<223> OTHER INFORMATION: gRNA

<400> SEQUENCE: 207
```

```
tcccagcttc actgtggctg ggg                                              23

<210> SEQ ID NO 208
<211> LENGTH: 23
<212> TYPE: DNA
<213> ORGANISM: Artificial Sequence
<220> FEATURE:
<223> OTHER INFORMATION: gRNA

<400> SEQUENCE: 208
ccacgagctg atgtgatcca tgg                                              23

<210> SEQ ID NO 209
<211> LENGTH: 23
<212> TYPE: DNA
<213> ORGANISM: Artificial Sequence
<220> FEATURE:
<223> OTHER INFORMATION: gRNA

<400> SEQUENCE: 209
tgtgatccat ggtgaaacat tgg                                              23

<210> SEQ ID NO 210
<211> LENGTH: 23
<212> TYPE: DNA
<213> ORGANISM: Artificial Sequence
<220> FEATURE:
<223> OTHER INFORMATION: gRNA

<400> SEQUENCE: 210
ccgatcagaa gctccatttc cgg                                              23

<210> SEQ ID NO 211
<211> LENGTH: 100
<212> TYPE: PRT
<213> ORGANISM: Brassica rapa

<400> SEQUENCE: 211

Met Glu Met Arg Ala Leu Val Ser Cys Ser Ala Ala Gly Asn Gly Ala
1               5                   10                  15

Ser Asp Arg Phe Arg Leu Ser Asn Val Ser Pro Trp Ile Thr Ser Ala
                20                  25                  30

Arg Gly Ala Ser Gly Ser Asp Ser Pro Ala Thr Val Lys Leu Gly Ser
            35                  40                  45

Ser Ser Met Ile Arg Ala Phe Lys Gly Val Ser Ile Tyr Lys Asn Lys
        50                  55                  60

Ser Arg Arg Asn Val Leu Ser Gln Arg Asn Lys Gln Phe Arg Pro Met
65                  70                  75                  80

Ala Tyr Leu Gly Arg Lys Asp Leu Ser Ser Pro Asp Pro Thr Ser Phe
                85                  90                  95

Cys Asp Asn Asp
            100

<210> SEQ ID NO 212
<211> LENGTH: 300
<212> TYPE: DNA
<213> ORGANISM: Brassica rapa

<400> SEQUENCE: 212
atggagatga gagcttttggt ttcgtgttct gctgccggaa atggagcttc tgatcggttt    60
agactctcca atgtttcacc atggatcaca tcagctcgtg gtgcaagtgg cagtgactcc    120
```

```
ccagccacag tgaagctggg aagcagctct atgatcagag ccttcaaagg agtttcgatt      180
tacaaaaaca agagcagaag aaatgttctg tctcaaagga acaaacagtt tcgtcctatg      240
gcctacttag gaaggaagga cttgagcagc cctgatccga cctccttctg cgataatgat      300
```

<210> SEQ ID NO 213
<211> LENGTH: 23
<212> TYPE: DNA
<213> ORGANISM: Artificial Sequence
<220> FEATURE:
<223> OTHER INFORMATION: gRNA

<400> SEQUENCE: 213

```
ttggtttcgt gttctgctgc cgg                                              23
```

<210> SEQ ID NO 214
<211> LENGTH: 23
<212> TYPE: DNA
<213> ORGANISM: Artificial Sequence
<220> FEATURE:
<223> OTHER INFORMATION: gRNA

<400> SEQUENCE: 214

```
tcgtgttctg ctgccggaaa tgg                                              23
```

<210> SEQ ID NO 215
<211> LENGTH: 23
<212> TYPE: DNA
<213> ORGANISM: Artificial Sequence
<220> FEATURE:
<223> OTHER INFORMATION: gRNA

<400> SEQUENCE: 215

```
ccggaaatgg agcttctgat cgg                                              23
```

<210> SEQ ID NO 216
<211> LENGTH: 23
<212> TYPE: DNA
<213> ORGANISM: Artificial Sequence
<220> FEATURE:
<223> OTHER INFORMATION: gRNA

<400> SEQUENCE: 216

```
gactctccaa tgtttcacca tgg                                              23
```

<210> SEQ ID NO 217
<211> LENGTH: 23
<212> TYPE: DNA
<213> ORGANISM: Artificial Sequence
<220> FEATURE:
<223> OTHER INFORMATION: gRNA

<400> SEQUENCE: 217

```
ccatggatca catcagctcg tgg                                              23
```

<210> SEQ ID NO 218
<211> LENGTH: 23
<212> TYPE: DNA
<213> ORGANISM: Artificial Sequence
<220> FEATURE:
<223> OTHER INFORMATION: gRNA

<400> SEQUENCE: 218

```
acatcagctc gtggtgcaag tgg                                              23
```

```
<210> SEQ ID NO 219
<211> LENGTH: 23
<212> TYPE: DNA
<213> ORGANISM: Artificial Sequence
<220> FEATURE:
<223> OTHER INFORMATION: gRNA

<400> SEQUENCE: 219
ctccccagcc acagtgaagc tgg                                              23

<210> SEQ ID NO 220
<211> LENGTH: 23
<212> TYPE: DNA
<213> ORGANISM: Artificial Sequence
<220> FEATURE:
<223> OTHER INFORMATION: gRNA

<400> SEQUENCE: 220
tctatgatca gagccttcaa agg                                              23

<210> SEQ ID NO 221
<211> LENGTH: 23
<212> TYPE: DNA
<213> ORGANISM: Artificial Sequence
<220> FEATURE:
<223> OTHER INFORMATION: gRNA

<400> SEQUENCE: 221
gaagaaatgt tctgtctcaa agg                                              23

<210> SEQ ID NO 222
<211> LENGTH: 95
<212> TYPE: PRT
<213> ORGANISM: Arabidopsis thaliana

<400> SEQUENCE: 222

Met Ala Gly Ser Val Asn Gly Asn His Ser Ala Val Gly Pro Gly Ile
1               5                   10                  15

Asn Tyr Glu Thr Val Ser Gln Val Asp Glu Phe Cys Lys Ala Leu Arg
            20                  25                  30

Gly Lys Arg Pro Ile His Ser Ile Leu Ile Ala Asn Asn Gly Met Ala
        35                  40                  45

Ala Val Lys Phe Ile Arg Ser Val Arg Thr Trp Ala Tyr Glu Thr Phe
    50                  55                  60

Gly Thr Glu Lys Ala Ile Leu Leu Val Gly Met Ala Thr Pro Glu Asp
65                  70                  75                  80

Met Arg Ile Asn Ala Glu His Ile Arg Ile Ala Asp Gln Phe Val
                85                  90                  95

<210> SEQ ID NO 223
<211> LENGTH: 23
<212> TYPE: DNA
<213> ORGANISM: Artificial Sequence
<220> FEATURE:
<223> OTHER INFORMATION: gRNA

<400> SEQUENCE: 223
tttcgtccta tggcctactt agg                                              23

<210> SEQ ID NO 224
<211> LENGTH: 23
<212> TYPE: DNA
<213> ORGANISM: Artificial Sequence
```

```
<220> FEATURE:
<223> OTHER INFORMATION: gRNA

<400> SEQUENCE: 224
gtcctatggc ctacttagga agg                                              23

<210> SEQ ID NO 225
<211> LENGTH: 23
<212> TYPE: DNA
<213> ORGANISM: Artificial Sequence
<220> FEATURE:
<223> OTHER INFORMATION: gRNA

<400> SEQUENCE: 225
tatggcctac ttaggaagga agg                                              23

<210> SEQ ID NO 226
<211> LENGTH: 300
<212> TYPE: DNA
<213> ORGANISM: Brassica napus

<400> SEQUENCE: 226
atcattatcg cagaaggagg tcggatcagg gctgctcaag tccttccttc ctaagtaggc      60
cataggacga aactgtttgt tcctttgaga cagaacattt cttctgctct tgtttttgta    120
aatcgaaact cctttgaagg ctctgatcat agagctgctt cccagcttca ctgtggctgg    180
ggagtcactg ccacttgcac cacgagctga tgtgatccat ggtgaaacat tggagagtct    240
aaaccgatca gaagctccat ttccggcagc agaacacgaa accaaagctc tcatctccat    300

<210> SEQ ID NO 227
<211> LENGTH: 23
<212> TYPE: DNA
<213> ORGANISM: Artificial Sequence
<220> FEATURE:
<223> OTHER INFORMATION: gRNA

<400> SEQUENCE: 227
tcattatcgc agaaggaggt cgg                                              23

<210> SEQ ID NO 228
<211> LENGTH: 23
<212> TYPE: DNA
<213> ORGANISM: Artificial Sequence
<220> FEATURE:
<223> OTHER INFORMATION: gRNA

<400> SEQUENCE: 228
tcgcagaagg aggtcggatc agg                                              23

<210> SEQ ID NO 229
<211> LENGTH: 23
<212> TYPE: DNA
<213> ORGANISM: Artificial Sequence
<220> FEATURE:
<223> OTHER INFORMATION: gRNA

<400> SEQUENCE: 229
caagtccttc cttcctaagt agg                                              23

<210> SEQ ID NO 230
<211> LENGTH: 23
<212> TYPE: DNA
<213> ORGANISM: Artificial Sequence
<220> FEATURE:
```

<223> OTHER INFORMATION: gRNA

<400> SEQUENCE: 230
ttccttccta agtaggccat agg                                          23

<210> SEQ ID NO 231
<211> LENGTH: 23
<212> TYPE: DNA
<213> ORGANISM: Artificial Sequence
<220> FEATURE:
<223> OTHER INFORMATION: gRNA

<400> SEQUENCE: 231
gtaaatcgaa actcctttga agg                                          23

<210> SEQ ID NO 232
<211> LENGTH: 23
<212> TYPE: DNA
<213> ORGANISM: Artificial Sequence
<220> FEATURE:
<223> OTHER INFORMATION: gRNA

<400> SEQUENCE: 232
gctgcttccc agcttcactg tgg                                          23

<210> SEQ ID NO 233
<211> LENGTH: 23
<212> TYPE: DNA
<213> ORGANISM: Artificial Sequence
<220> FEATURE:
<223> OTHER INFORMATION: gRNA

<400> SEQUENCE: 233
cttcccagct tcactgtggc tgg                                          23

<210> SEQ ID NO 234
<211> LENGTH: 23
<212> TYPE: DNA
<213> ORGANISM: Artificial Sequence
<220> FEATURE:
<223> OTHER INFORMATION: gRNA

<400> SEQUENCE: 234
ttcccagctt cactgtggct ggg                                          23

<210> SEQ ID NO 235
<211> LENGTH: 23
<212> TYPE: DNA
<213> ORGANISM: Artificial Sequence
<220> FEATURE:
<223> OTHER INFORMATION: gRNA

<400> SEQUENCE: 235
tcccagcttc actgtggctg ggg                                          23

<210> SEQ ID NO 236
<211> LENGTH: 23
<212> TYPE: DNA
<213> ORGANISM: Artificial Sequence
<220> FEATURE:
<223> OTHER INFORMATION: gRNA

<400> SEQUENCE: 236
ccacgagctg atgtgatcca tgg                                          23

```
<210> SEQ ID NO 237
<211> LENGTH: 23
<212> TYPE: DNA
<213> ORGANISM: Artificial Sequence
<220> FEATURE:
<223> OTHER INFORMATION: gRNA

<400> SEQUENCE: 237
tgtgatccat ggtgaaacat tgg                                            23

<210> SEQ ID NO 238
<211> LENGTH: 23
<212> TYPE: DNA
<213> ORGANISM: Artificial Sequence
<220> FEATURE:
<223> OTHER INFORMATION: gRNA

<400> SEQUENCE: 238
ccgatcagaa gctccatttc cgg                                            23

<210> SEQ ID NO 239
<211> LENGTH: 23
<212> TYPE: DNA
<213> ORGANISM: Artificial Sequence
<220> FEATURE:
<223> OTHER INFORMATION: gRNA

<400> SEQUENCE: 239
tccatggaga tatattcgtg agg                                            23

<210> SEQ ID NO 240
<211> LENGTH: 23
<212> TYPE: DNA
<213> ORGANISM: Artificial Sequence
<220> FEATURE:
<223> OTHER INFORMATION: gRNA

<400> SEQUENCE: 240
ccctcacgaa tatatctcca tgg                                            23

<210> SEQ ID NO 241
<211> LENGTH: 23
<212> TYPE: DNA
<213> ORGANISM: Artificial Sequence
<220> FEATURE:
<223> OTHER INFORMATION: gRNA

<400> SEQUENCE: 241
gatatattcg tgagggtaat tgg                                            23

<210> SEQ ID NO 242
<211> LENGTH: 23
<212> TYPE: DNA
<213> ORGANISM: Artificial Sequence
<220> FEATURE:
<223> OTHER INFORMATION: gRNA

<400> SEQUENCE: 242
cttctcagct tcactgtcga cgg                                            23

<210> SEQ ID NO 243
<211> LENGTH: 23
<212> TYPE: DNA
<213> ORGANISM: Artificial Sequence
<220> FEATURE:
<223> OTHER INFORMATION: gRNA
```

<400> SEQUENCE: 243
ccatggagat atattcgtga ggg					23

<210> SEQ ID NO 244
<211> LENGTH: 23
<212> TYPE: DNA
<213> ORGANISM: Artificial Sequence
<220> FEATURE:
<223> OTHER INFORMATION: gRNA

<400> SEQUENCE: 244
cttcgacaag agttttgtct cgg					23

<210> SEQ ID NO 245
<211> LENGTH: 23
<212> TYPE: DNA
<213> ORGANISM: Artificial Sequence
<220> FEATURE:
<223> OTHER INFORMATION: gRNA

<400> SEQUENCE: 245
tcaagagtga gaacctttaa agg					23

<210> SEQ ID NO 246
<211> LENGTH: 23
<212> TYPE: DNA
<213> ORGANISM: Artificial Sequence
<220> FEATURE:
<223> OTHER INFORMATION: gRNA

<400> SEQUENCE: 246
tcttcgtgtt ctactggtaa tgg					23

<210> SEQ ID NO 247
<211> LENGTH: 23
<212> TYPE: DNA
<213> ORGANISM: Artificial Sequence
<220> FEATURE:
<223> OTHER INFORMATION: gRNA

<400> SEQUENCE: 247
ttgggttctt cgtgttctac tgg					23

<210> SEQ ID NO 248
<211> LENGTH: 23
<212> TYPE: DNA
<213> ORGANISM: Artificial Sequence
<220> FEATURE:
<223> OTHER INFORMATION: gRNA

<400> SEQUENCE: 248
tgtcgaagaa actcctttaa agg					23

<210> SEQ ID NO 249
<211> LENGTH: 23
<212> TYPE: DNA
<213> ORGANISM: Artificial Sequence
<220> FEATURE:
<223> OTHER INFORMATION: gRNA

<400> SEQUENCE: 249
tcttgacgaa actcctttga agg					23

<210> SEQ ID NO 250
<211> LENGTH: 23

```
<212> TYPE: DNA
<213> ORGANISM: Artificial Sequence
<220> FEATURE:
<223> OTHER INFORMATION: gRNA

<400> SEQUENCE: 250
agtagtttga gaaccttcaa agg                                              23

<210> SEQ ID NO 251
<211> LENGTH: 23
<212> TYPE: DNA
<213> ORGANISM: Artificial Sequence
<220> FEATURE:
<223> OTHER INFORMATION: gRNA

<400> SEQUENCE: 251
tcgtgttcta ctggtaatgg agg                                              23

<210> SEQ ID NO 252
<211> LENGTH: 23
<212> TYPE: DNA
<213> ORGANISM: Artificial Sequence
<220> FEATURE:
<223> OTHER INFORMATION: gRNA

<400> SEQUENCE: 252
ggaaaaactg ttgtgatcca tgg                                              23

<210> SEQ ID NO 253
<211> LENGTH: 23
<212> TYPE: DNA
<213> ORGANISM: Artificial Sequence
<220> FEATURE:
<223> OTHER INFORMATION: gRNA

<400> SEQUENCE: 253
aaacagagga aactgttgtt tgg                                              23

<210> SEQ ID NO 254
<211> LENGTH: 23
<212> TYPE: DNA
<213> ORGANISM: Artificial Sequence
<220> FEATURE:
<223> OTHER INFORMATION: gRNA

<400> SEQUENCE: 254
gggtttagga aacaaaacag agg                                              23

<210> SEQ ID NO 255
<211> LENGTH: 24
<212> TYPE: DNA
<213> ORGANISM: Artificial Sequence
<220> FEATURE:
<223> OTHER INFORMATION: ACC2 target

<400> SEQUENCE: 255
gattgcctca cgaatatatc tcca                                             24

<210> SEQ ID NO 256
<211> LENGTH: 24
<212> TYPE: DNA
<213> ORGANISM: Artificial Sequence
<220> FEATURE:
<223> OTHER INFORMATION: ACC2 target

<400> SEQUENCE: 256
```

```
aaactggaga tatattcgtg aggc                                              24

<210> SEQ ID NO 257
<211> LENGTH: 24
<212> TYPE: DNA
<213> ORGANISM: Artificial Sequence
<220> FEATURE:
<223> OTHER INFORMATION: primer

<400> SEQUENCE: 257
tctcttcctc cttaaaaagc caca                                              24

<210> SEQ ID NO 258
<211> LENGTH: 20
<212> TYPE: DNA
<213> ORGANISM: Artificial Sequence
<220> FEATURE:
<223> OTHER INFORMATION: primer

<400> SEQUENCE: 258
ctaggattcg aaaccagcgt                                                   20

<210> SEQ ID NO 259
<211> LENGTH: 23
<212> TYPE: DNA
<213> ORGANISM: Artificial Sequence
<220> FEATURE:
<223> OTHER INFORMATION: Zm-PPR10  wt binding site

<400> SEQUENCE: 259
attgtatcct taaccatttc ttt                                               23

<210> SEQ ID NO 260
<211> LENGTH: 23
<212> TYPE: DNA
<213> ORGANISM: Artificial Sequence
<220> FEATURE:
<223> OTHER INFORMATION: Bn-PPR10 wt binding site

<400> SEQUENCE: 260
attgtatcat taactatttc ttt                                               23

<210> SEQ ID NO 261
<211> LENGTH: 23
<212> TYPE: DNA
<213> ORGANISM: Artificial Sequence
<220> FEATURE:
<223> OTHER INFORMATION: Zm-PPR10GG mut binding site

<400> SEQUENCE: 261
attgtaggct taaccatttc ttt                                               23

<210> SEQ ID NO 262
<211> LENGTH: 1140
<212> TYPE: DNA
<213> ORGANISM: Artificial Sequence
<220> FEATURE:
<223> OTHER INFORMATION: Prrn-PPR10GG-GFP-TrbcL

<400> SEQUENCE: 262
gagctcgctc ccccgccgtc gttcaatgag aatggataag aggctcgtgg gattgacgtg       60 aggggcagg gatggctata tttctgggag ttacttctac ccgatagagc ttagaagttg       120
gaagtaataa tttcttggtt gattgtaggc ttaaccattt cttttttttt gacacgagga      180
actcatcatg gctagcagta aaggagaaga acttttcact ggagttgtcc caattcttgt      240
```

```
tgaattagat ggtgatgtta atgggcacaa attttctgtc agtggagagg gtgaaggtga    300
tgcaacatac ggaaaactta cccttaaatt tatttgcact actggaaaac tacctgttcc    360
ttggccaaca cttgtcacta ctttctctta tggtgttcaa tgcttttcaa gatacccaga    420
tcatatgaag cggcacgact tcttcaagag cgccatgcct gagggatacg tgcaggagag    480
gaccatctct ttcaaggacg acgggaacta caagacacgt gctgaagtca gtttgaggg    540 agacaccctc gtcaacagga tcgagcttaa gggaatcgat ttcaaggagg acggaaacat    600
cctcggccac aagttggaat acaactacaa ctcccacaac gtatacatca cggcagacaa    660
acaaaagaat ggaatcaaag ctaacttcaa aattagacac aacattgaag atggaagcgt    720
tcaactagca gaccattatc aacaaaatac tccaattggc gatggccctg tccttttacc    780
agacaaccat tacctgtcca cacaatctgc cctttcgaaa gatcccaacg aaaagagaga    840
ccacatggtc cttcttgagt ttgtaacagc tgctgggatt acacatggca tggatgaact    900
gtacaaataa atctagaaaa cagtagacat tagcagataa attagcagga aataaagaag    960
gataaggaga aagaactcaa gtaattatcc ttcgttctct taattgaatt gcaattaaac   1020
tcggcccaat cttttactaa aaggattgag ccgaatacaa caaagattct attgcatata   1080
ttttgactaa gtatatactt acctagatat acaagatttg aaatacaaaa tctaaagctt   1140
```

<210> SEQ ID NO 263
<211> LENGTH: 147
<212> TYPE: DNA
<213> ORGANISM: Artificial Sequence
<220> FEATURE:
<223> OTHER INFORMATION: tRNA

<400> SEQUENCE: 263

```
aagtctttac aatgacaatg gaaaccgatg taaagggatg tagcgcagct tggtagcgcg     60
tttgttttgg gtacaaaatg tcacaggttc aaatcctgtc atccctatcc ctaacttgta    120
gttatcgtat cagcagtaac aatagat                                        147
```

<210> SEQ ID NO 264
<211> LENGTH: 2361
<212> TYPE: DNA
<213> ORGANISM: Zea mays

<400> SEQUENCE: 264

```
atggaggcca ccggcagggg gctgttcccg aacaagccca ccctcccggc ggggccgagg     60
aaacggggcc cgctcctccc ggccgcgccc ccgccaccgt cccctcctc gctcccgctc    120 gactcgctcc tgctccacct caccgcgccc gccccgcgc cggccccgc gccgcggcgg     180 tcgcaccaga cgccgacgcc gccgcactcc ttcctctccc ccgacgcgca ggtgctggtg    240
ctcgccatct cctcgcaccc gctccccacg ctggcggcct tcctggcctc ccgccgcgac    300
gagctcctcc gcgcggacat cacgtccctg ctcaaggcgc tggagctctc ggggcactgg    360
gagtgggcgc tcgcgctcct ccggtgggca ggcaaggagg gtgccgccga cgcgtcggcg    420
ctcgagatgg tcgtccgcgc gctgggccgc gagggccagc acgacgccgt ctgcgcgctg    480
ctcgacgaaa cgccgctccc gccgggctcc cgcctcgacg tccgcgccta caccaccgtg    540
ctgcacgcgc tctcccgcgc gggccggtac gagcgcgcgc tcgagctctt cgccgagctc    600
cggcgccagg gggtggcgcc cacgctcgtc acctacaacg tcgtgctgga cgtgtacggg    660
cggatgggcc ggtcgtggcc gcggatcgtc gccctcctcg atgagatgcg cgccgccggg    720
```

```
gtcgagcccg acggcttcac cgccagcacg gtgatcgccg cgtgctgccg cgacgggctg      780
gttgacgagg cggtggcgtt cttcgaggac ctcaaggccc gcggccacgc ccgtgcgtc       840 gtcacgtaca acgcgttgct ccaggtgttc ggcaaggccg gaactacac ggaggcgctg       900 cgcgtgctcg gggagatgga gcagaacggc tgccagccag atgctgtgac gtacaacgag      960
ctcgccggaa cgtacgcccg ggctgggttc ttcgaggagg ctgccaggtg cctggacaca     1020
atggcatcca agggtctgtt gccaaacgca ttcacgtaca acaccgtgat gacagcctat     1080
gggaatgttg ggaaggtgga tgaggcgctc gctctgtttg accagatgaa gaagaccggg     1140
ttcgtgccga acgtgaacac gtacaatctt gtccttggca tgcttggcaa gaagtcaagg     1200
ttcacggtga tgctagagat gcttggagag atgtcgagga gcggatgcac accgaaccgg     1260
gtaacatgga acacaatgct tgcagtctgt gggaagcgtg gcatggagga ctacgtcacc     1320
cgggttctgg aggggatgag gtcttgcggg gttgaactga gccgagacac ctacaacacc     1380
ctgatagctg cgtacggccg gtgtggctcg aggactaatg ccttcaagat gtacaacgag     1440
atgaccagcg ctggattcac cccctgcatc accacgtaca acgcgttgct gaacgtgctg     1500
tcgcggcagg gcgactggtc caccgcccag tcgatcgtaa gcaaaatgag gaccaagggg     1560
ttcaagccga acgagcagtc gtattcgctg ctgctccagt gctacgcgaa gggggcaac     1620 gtggcaggga tagccgcgat cgagaacgag gtgtacggat caggtgccgt tttcccaagc     1680
tgggtgatcc tgaggaccct tgtcatcgcc aatttcaagt gccggcgact ggatggcatg     1740
gagacggcgt ttcaagaggt gaaggccaga ggctacaacc cggacctcgt gatattcaac     1800
tccatgctgt ccatctacgc gaagaacggg atgtacagca aggccaccga ggtcttcgac     1860
tccatcaagc ggagcgggct gagccccgac ctcatcacct acaacagcct gatggacatg     1920
tacgccaagt gcagcgagtc gtgggaggcc gagaagatac tgaaccagct caagtgctcc     1980
cagacgatga agcccgacgt ggtgtcctac aacacggtca taaacgggtt ctgcaagcag     2040
gggctggtga agaggcccca gagggtcctc tcggagatgg tcgccgacgg catggccccc     2100
tgcgccgtga cctaccacac gctcgtcggg ggttactcca gcctggagat gttcagcgag     2160
gccagggagg tcatcggcta catggtccag cacggcctca agcctatgga gctgacctac     2220
aggagagtcg tcgagagcta ctgcagagcg aagcggttcg aggaggctcg cggcttcctg     2280
tccgaggtct cggagaccga cctggatttt gacaagaagg cgctcgaagc ctatatagag     2340
gatgcgcagt ttggaaggta g                                              2361

<210> SEQ ID NO 265
<211> LENGTH: 2361
<212> TYPE: DNA
<213> ORGANISM: Artificial Sequence
<220> FEATURE:
<223> OTHER INFORMATION: Zm_PPR10 GG

<400> SEQUENCE: 265
atggaggcca ccggcagggg gctgttcccg aacaagccca ccctcccggc ggggccgagg       60
aaacggggcc cgctcctccc ggccgcgccc ccgccaccgt cccctcctc gctcccgctc      120 gactcgctcc tgctccacct caccgcgccc gccccgcgc cggccccgc gccgcggcgg      180 tcgcaccaga cgccgacgcc gccgcactcc ttcctctccc cgacgcgca ggtgctggtg      240 ctcgccatct cctcgcaccc gctccccacg ctggcggcct tcctggcctc cgccgcgac      300 gagctcctcc gcgcggacat cacgtccctg ctcaaggcgc tggagctctc ggggcactgg      360
gagtgggcgc tcgcgctcct ccggtgggca ggcaaggagg gtgccgccga cgcgtcggcg      420
```

```
ctcgagatgg tcgtccgcgc gctgggccgc gagggccagc acgacgccgt ctgcgcgctg      480
ctcgacgaaa cgccgctccc gccgggctcc cgcctcgacg tccgcgccta caccaccgtg      540
ctgcacgcgc tctcccgcgc gggccggtac gagcgcgcgc tcgagctctt cgccgagctc      600
cggcgccagg gggtggcgcc cacgctcgtc acctacaacg tcgtgctgga cgtgtacggg      660
cggatgggcc ggtcgtggcc gcggatcgtc gccctcctcg atgagatgcg cgccgccggg      720
gtcgagcccg acggcttcac cgccagcacg gtgatcgccg cgtgctgccg cgacgggctg      780
gttgacgagg cggtggcgtt cttcgaggac ctcaaggccc gcggccacgc cccgtgcgtc      840
gtcacgtaca cagcgttgct ccaggtgttc ggcaaggccg ggaactacac ggaggcgctg      900
cgcgtgctcg gggagatgga gcagaacggc tgccagccag atgctgtgac gtacaccgag      960
ctcgccggaa cgtacgcccg ggctgggttc ttcgaggagg ctgccaggtg cctggacaca     1020
atggcatcca agggtctgtt gccaaacgca ttcacgtaca acaccgtgat gacagcctat     1080
gggaatgttg gaaggtgga tgaggcgctc gctctgtttg accagatgaa gaagaccggg     1140
ttcgtgccga acgtgaacac gtacaatctt gtccttggca tgcttggcaa gaagtcaagg     1200
ttcacggtga tgctagagat gcttggagag atgtcgagga gcggatgcac accgaaccgg     1260
gtaacatgga acacaatgct tgcagtctgt gggaagcgtg gcatggagga ctacgtcacc     1320
cgggttctgg aggggatgag gtcttgcggg gttgaactga gccgagacac ctacaacacc     1380
ctgatagctg cgtacggccg gtgtggctcg aggactaatg ccttcaagat gtacaacgag     1440
atgaccagcg ctggattcac ccctgcatc accacgtaca acgcgttgct gaacgtgctg     1500
tcgcggcagg gcgactggtc caccgcccag tcgatcgtaa gcaaaatgag gaccaagggg     1560
ttcaagccga acgagcagtc gtattcgctg ctgctccagt gctacgcgaa gggggggcaac     1620 gtggcaggga tagccgcgat cgagaacgag gtgtacggat caggtgccgt tttcccaagc     1680
tgggtgatcc tgaggaccct tgtcatcgcc aatttcaagt gccggcgact ggatggcatg     1740
gagacggcgt ttcaagaggt gaaggccaga ggctacaacc cggacctcgt gatattcaac     1800
tccatgctgt ccatctacgc gaagaacggg atgtacagca aggccaccga ggtcttcgac     1860
tccatcaagc ggagcgggct gagccccgac ctcatcacct acaacagcct gatggacatg     1920
tacgccaagt gcagcgagtc gtgggaggcc gagaagatac tgaaccagct caagtgctcc     1980
cagacgatga agcccgacgt ggtgtcctac aacacggtca taaacgggtt ctgcaagcag     2040
gggctggtga agaggcccca gagggtcctc tcggagatgg tcgccgacgg catggccccc     2100
tgcgccgtga cctaccacac gctcgtcggg ggttactcca gcctggagat gttcagcgag     2160
gccagggagg tcatcggcta catggtccag cacggcctca agcctatgga gctgacctac     2220
aggagagtcg tcgagagcta ctgcagagcg aagcggttcg aggaggctcg cggcttcctg     2280
tccgaggtct cggagaccga cctggatttt gacaagaagg cgctcgaagc ctatatagag     2340
gatgcgcagt ttggaaggta g                                              2361
```

<210> SEQ ID NO 266
<211> LENGTH: 1415
<212> TYPE: DNA
<213> ORGANISM: Artificial Sequence
<220> FEATURE:
<223> OTHER INFORMATION: Phaseolin promoter

<400> SEQUENCE: 266

```
ggtcgacggt atcgataagc ttgatatcga attcctgcag cccaattcat tgtactccca       60
```

-continued

| | |
|---|---|
| gtatcattat agtgaaagtt ttggctctct cgccggtggt tttttacctc tatttaaagg | 120 |
| ggttttccac ctaaaaattc tggtatcatt ctcactttac ttgttacttt aatttctcat | 180 |
| aatctttggt tgaaattatc acgcttccgc acacgatatc cctacaaatt tattatttgt | 240 |
| taaacatttt caaaccgcat aaaattttat gaagtcccgt ctatcttaa tgtagtctaa | 300 |
| catttcata ttgaaatata taatttactt aattttagcg ttggtagaaa gcataatgat | 360 |
| ttattcttat tcttcttcat ataaatgttt aatatacaat ataaacaaat tctttacctt | 420 |
| aagaaggatt tcccatttta tattaaaa atatatttat caaatatttt tcaaccacgt | 480 |
| aaatctcata ataataagtt gtttcaaaag taataaaatt taactccata attttttat | 540 |
| tcgactgatc ttaaagcaac acccagtgac acaactagcc atttttttct ttggataaaa | 600 |
| aaatccaatt atcattgtat ttttttata caatgaaaat ttcaccaaac aatcatttgt | 660 |
| ggtatttctg aagcaagtca tgttatgcaa aattctataa ttcccatttg acactacgga | 720 |
| agtaactgaa gatctgcttt tacatgcgag acacatcttc taaagtaatt ttaataatag | 780 |
| ttactatatt caagatttca tatatcaaat actcaatatt acttctaaaa aattaattag | 840 |
| atataattaa aatattactt tttaatttt aagtttaatt gttgaatttg tgactattga | 900 |
| tttattattc tactatgttt aaattgtttt atagatagtt taaagtaaat ataagtaatg | 960 |
| tagtagagtg ttagagtgtt accctaaacc ataaactata acatttatgg tggactaatt | 1020 |
| ttcatatatt tcttattgct tttaccttt cttggtatgt aagtccgtaa ctagaattac | 1080 |
| tgtgggttgc catggcactc tgtggtcttt tggttcatgc atggatgctt gcgcaagaaa | 1140 |
| aagacaaaga acaaagaaaa aagacaaaac agagagacaa aacgcaatca cacaaccaac | 1200 |
| tcaaattagt cactggctga tcaagatcgc cgcgtccatg tatgtctaaa tgccatgcaa | 1260 |
| agcaacacgt gcttaacatg cactttaaat ggctcaccca tctcaaccca cacacaaaca | 1320 |
| cattgccttt ttcttcatca tcaccacaac cacctgtata tattcattct cttccgccac | 1380 |
| ctcaatttct tcacttcaac acacgtcaac ctgca | 1415 |

<210> SEQ ID NO 267
<211> LENGTH: 22
<212> TYPE: DNA
<213> ORGANISM: Brassica napus

<400> SEQUENCE: 267

| | |
|---|---|
| ggtttagact ctccaatgtt tc | 22 |

<210> SEQ ID NO 268
<211> LENGTH: 24
<212> TYPE: DNA
<213> ORGANISM: Artificial Sequence
<220> FEATURE:
<223> OTHER INFORMATION: Forward Oligo

<400> SEQUENCE: 268

| | |
|---|---|
| gattgctttg taacctctca gatt | 24 |

<210> SEQ ID NO 269
<211> LENGTH: 24
<212> TYPE: DNA
<213> ORGANISM: Artificial Sequence
<220> FEATURE:
<223> OTHER INFORMATION: Reverse Oligo

<400> SEQUENCE: 269

| | |
|---|---|
| aaacaatctg agaggttaca aagc | 24 |

<210> SEQ ID NO 270
<211> LENGTH: 22
<212> TYPE: DNA
<213> ORGANISM: Brassica napus

<400> SEQUENCE: 270
ggaaggaagg acttgagcag cc                                              22

<210> SEQ ID NO 271
<211> LENGTH: 24
<212> TYPE: DNA
<213> ORGANISM: Artificial Sequence
<220> FEATURE:
<223> OTHER INFORMATION: Forward Oligo

<400> SEQUENCE: 271
gattgccgac gagttcagga agga                                            24

<210> SEQ ID NO 272
<211> LENGTH: 24
<212> TYPE: DNA
<213> ORGANISM: Artificial Sequence
<220> FEATURE:
<223> OTHER INFORMATION: Reverse Oligo

<400> SEQUENCE: 272
aaactccttc ctgaactcgt cggc                                            24

<210> SEQ ID NO 273
<211> LENGTH: 22
<212> TYPE: DNA
<213> ORGANISM: Brassica napus

<400> SEQUENCE: 273
ggtgaaacat tggagagtct aa                                              22

<210> SEQ ID NO 274
<211> LENGTH: 24
<212> TYPE: DNA
<213> ORGANISM: Artificial Sequence
<220> FEATURE:
<223> OTHER INFORMATION: Forward Oligo

<400> SEQUENCE: 274
gattgaatct gagaggttac aaag                                            24

<210> SEQ ID NO 275
<211> LENGTH: 24
<212> TYPE: DNA
<213> ORGANISM: Artificial Sequence
<220> FEATURE:
<223> OTHER INFORMATION: Reverse Oligo

<400> SEQUENCE: 275
aaacctttgt aacctctcag attc                                            24

<210> SEQ ID NO 276
<211> LENGTH: 22
<212> TYPE: DNA
<213> ORGANISM: Brassica napus

<400> SEQUENCE: 276
ggagcttctg atcggtttag ac                                              22

```
<210> SEQ ID NO 277
<211> LENGTH: 22
<212> TYPE: DNA
<213> ORGANISM: Brassica napus

<400> SEQUENCE: 277
ggtgcaagtg gcagtgactc cc                                              22

<210> SEQ ID NO 278
<211> LENGTH: 22
<212> TYPE: DNA
<213> ORGANISM: Brassica napus

<400> SEQUENCE: 278
gacaccgacc cctcagtgac gg                                              22

<210> SEQ ID NO 279
<211> LENGTH: 22
<212> TYPE: DNA
<213> ORGANISM: Brassica napus

<400> SEQUENCE: 279
ggagtttcga tttacaaaaa ca                                              22

<210> SEQ ID NO 280
<211> LENGTH: 22
<212> TYPE: DNA
<213> ORGANISM: Brassica napus

<400> SEQUENCE: 280
ggcctactta ggaaggaagg ac                                              22

<210> SEQ ID NO 281
<211> LENGTH: 22
<212> TYPE: DNA
<213> ORGANISM: Brassica napus

<400> SEQUENCE: 281
ggaaggactt gagcagccct ga                                              22

<210> SEQ ID NO 282
<211> LENGTH: 23
<212> TYPE: DNA
<213> ORGANISM: Brassica napus

<400> SEQUENCE: 282
gtcctatggc ctacttagga agg                                             23

<210> SEQ ID NO 283
<211> LENGTH: 22
<212> TYPE: DNA
<213> ORGANISM: Brassica napus

<400> SEQUENCE: 283
ggacttgagc agccctgatc cg                                              22

<210> SEQ ID NO 284
<211> LENGTH: 22
<212> TYPE: DNA
<213> ORGANISM: Brassica napus

<400> SEQUENCE: 284
atggcctact taggaaggaa gg                                              22
```

```
<210> SEQ ID NO 285
<211> LENGTH: 22
<212> TYPE: DNA
<213> ORGANISM: Brassica napus

<400> SEQUENCE: 285
cgacctcctt ctgcgataat gg                                              22

<210> SEQ ID NO 286
<211> LENGTH: 22
<212> TYPE: DNA
<213> ORGANISM: Brassica napus

<400> SEQUENCE: 286
ggagagtcta aaccgatcag aa                                              22

<210> SEQ ID NO 287
<211> LENGTH: 22
<212> TYPE: DNA
<213> ORGANISM: Brassica napus

<400> SEQUENCE: 287
ggagtcactg ccacttgcac ca                                              22

<210> SEQ ID NO 288
<211> LENGTH: 23
<212> TYPE: DNA
<213> ORGANISM: Brassica napus

<400> SEQUENCE: 288
ggggagtcac tgccacttgc acc                                             23

<210> SEQ ID NO 289
<211> LENGTH: 23
<212> TYPE: DNA
<213> ORGANISM: Brassica napus

<400> SEQUENCE: 289
ggctggggag tcactgccac ttg                                             23

<210> SEQ ID NO 290
<211> LENGTH: 22
<212> TYPE: DNA
<213> ORGANISM: Brassica napus

<400> SEQUENCE: 290
ggtcttgttt ttgtaaatcg aa                                              22

<210> SEQ ID NO 291
<211> LENGTH: 22
<212> TYPE: DNA
<213> ORGANISM: Brassica napus

<400> SEQUENCE: 291
tccttcctaa gtaggccata gg                                              22

<210> SEQ ID NO 292
<211> LENGTH: 22
<212> TYPE: DNA
<213> ORGANISM: Brassica napus

<400> SEQUENCE: 292
```
aagtccttcc ttcctaagta gg          22

<210> SEQ ID NO 293
<211> LENGTH: 22
<212> TYPE: DNA
<213> ORGANISM: Brassica napus

<400> SEQUENCE: 293
ggctgctcaa gtccttcctt cc          22

<210> SEQ ID NO 294
<211> LENGTH: 22
<212> TYPE: DNA
<213> ORGANISM: Brassica napus

<400> SEQUENCE: 294
gcagaaggag gtcggatcag gg          22

<210> SEQ ID NO 295
<211> LENGTH: 22
<212> TYPE: DNA
<213> ORGANISM: Brassica napus

<400> SEQUENCE: 295
gggctgctca agtccttcct tc          22

<210> SEQ ID NO 296
<211> LENGTH: 22
<212> TYPE: DNA
<213> ORGANISM: Brassica napus

<400> SEQUENCE: 296
cgcagaagga ggtcggatca gg          22

<210> SEQ ID NO 297
<211> LENGTH: 22
<212> TYPE: DNA
<213> ORGANISM: Brassica napus

<400> SEQUENCE: 297
cattatcgca gaaggaggtc gg          22

<210> SEQ ID NO 298
<211> LENGTH: 22
<212> TYPE: DNA
<213> ORGANISM: Brassica napus

<400> SEQUENCE: 298
ggtcggatca gggctgctca ag          22

<210> SEQ ID NO 299
<211> LENGTH: 22
<212> TYPE: DNA
<213> ORGANISM: Brassica napus

<400> SEQUENCE: 299
ggaggtcgga tcagggctgc tc          22

<210> SEQ ID NO 300
<211> LENGTH: 22
<212> TYPE: DNA
<213> ORGANISM: Brassica napus

<400> SEQUENCE: 300

<210> SEQ ID NO 301
<211> LENGTH: 197
<212> TYPE: PRT
<213> ORGANISM: Arabidopsis thaliana

<400> SEQUENCE: 301

Met Glu Met Arg Ala Leu Gly Ser Ser Cys Ser Thr Gly Asn Gly Gly
1               5                   10                  15

Ser Ala Pro Ile Thr Leu Thr Asn Ile Ser Pro Trp Ile Thr Thr Val
                20                  25                  30

Phe Pro Ser Thr Val Lys Leu Arg Ser Ser Leu Arg Thr Phe Lys Gly
            35                  40                  45

Val Ser Arg Val Arg Thr Phe Lys Gly Val Ser Thr Arg Val
    50                  55                  60

Leu Ser Arg Thr Lys Gln Gln Phe Pro Leu Phe Cys Phe Leu Asn Pro
65                  70                  75                  80

Asp Pro Ile Ser Phe Leu Glu Asn Asp Val Ser Glu Ala Glu Arg Thr
                85                  90                  95

Val Val Leu Pro Asp Gly Ser Val Asn Gly Ala Gly Ser Val Asn Gly
            100                 105                 110

Tyr His Ser Asp Val Val Pro Gly Arg Asn Val Ala Glu Val Asn Glu
        115                 120                 125

Phe Cys Lys Ala Leu Gly Gly Lys Arg Pro Ile His Ser Ile Leu Val
    130                 135                 140

Ala Thr Asn Gly Met Ala Val Lys Phe Ile Arg Ser Val Arg Thr
145                 150                 155                 160

Trp Ala Tyr Glu Thr Phe Gly Ser Glu Lys Ala Val Lys Leu Val Ala
                165                 170                 175

Met Ala Thr Pro Glu Asp Met Arg Ile Asn Ala Glu His Ile Arg Ile
            180                 185                 190

Ala Asp Gln Phe Val
        195

<210> SEQ ID NO 302
<211> LENGTH: 92
<212> TYPE: PRT
<213> ORGANISM: Artificial Sequence
<220> FEATURE:
<223> OTHER INFORMATION: consensus sequence
<220> FEATURE:
<221> NAME/KEY: SITE
<222> LOCATION: (20)..(20)
<223> OTHER INFORMATION: Xaa is any one of N,D,Q, E, B, and Z.
<220> FEATURE:
<221> NAME/KEY: SITE
<222> LOCATION: (20)..(20)
<223> OTHER INFORMATION: Xaa is any one of N, D, Q, E, B, and Z.
<220> FEATURE:
<221> NAME/KEY: SITE
<222> LOCATION: (22)..(22)
<223> OTHER INFORMATION: Xaa is any one of N,D,Q, E, B, and Z.
<220> FEATURE:
<221> NAME/KEY: SITE
<222> LOCATION: (39)..(39)
<223> OTHER INFORMATION: Xaa is I or V.
<220> FEATURE:
<221> NAME/KEY: SITE
<222> LOCATION: (67)..(67)
<223> OTHER INFORMATION: Xaa is I or V.

<400> SEQUENCE: 302

Gly Ala Gly Ser Val Asn Gly Asn His Ser Ala Val Gly Pro Gly Arg
1               5                   10                  15

Asn Val Ala Xaa Val Xaa Glu Phe Cys Lys Ala Leu Arg Gly Lys Arg
            20              25                  30

Pro Ile His Ser Ile Leu Xaa Ala Asn Asn Gly Met Ala Ala Val Lys
            35              40                  45

Phe Ile Arg Ser Val Arg Thr Trp Ala Tyr Glu Thr Phe Gly Ser Glu
            50              55                  60

Lys Ala Xaa Leu Leu Val Ala Met Ala Thr Pro Glu Asp Met Arg Ile
65              70                  75                  80

Asn Ala Glu His Ile Arg Ile Ala Asp Gln Phe Val
            85                  90

<210> SEQ ID NO 303
<211> LENGTH: 200
<212> TYPE: PRT
<213> ORGANISM: Arabidopsis thaliana

<400> SEQUENCE: 303

Met Ala Gly Ser Val Asn Gly Asn His Ser Ala Val Gly Pro Gly Ile
1               5                   10                  15

Asn Tyr Glu Thr Val Ser Gln Val Asp Glu Phe Cys Lys Ala Leu Arg
            20              25                  30

Gly Lys Arg Pro Ile His Ser Ile Leu Ile Ala Asn Asn Gly Met Ala
            35              40                  45

Ala Val Lys Phe Ile Arg Ser Val Arg Thr Trp Ala Tyr Glu Thr Phe
            50              55                  60

Gly Thr Glu Lys Ala Ile Leu Leu Val Gly Met Ala Thr Pro Glu Asp
65              70                  75                  80

Met Arg Ile Asn Ala Glu His Ile Arg Ile Ala Asp Gln Phe Val Glu
            85                  90                  95

Val Pro Gly Gly Thr Asn Asn Asn Tyr Ala Asn Val Gln Leu Ile
            100             105             110

Val Glu Met Ala Glu Val Thr Arg Val Asp Ala Val Trp Pro Gly Trp
            115             120                 125

Gly His Ala Ser Glu Asn Pro Glu Leu Pro Asp Ala Leu Asp Ala Lys
            130             135                 140

Gly Ile Ile Phe Leu Gly Pro Pro Ala Ser Ser Met Ala Ala Leu Gly
145             150             155                 160

Asp Lys Ile Gly Ser Ser Leu Ile Ala Gln Ala Ala Asp Val Pro Thr
            165             170                 175

Leu Pro Trp Ser Gly Ser His Val Lys Ile Pro Pro Asn Ser Asn Leu
            180             185                 190

Val Thr Ile Pro Glu Glu Ile Tyr
            195             200

<210> SEQ ID NO 304
<211> LENGTH: 200
<212> TYPE: PRT
<213> ORGANISM: Arabidopsis lyrata

<400> SEQUENCE: 304

Met Ala Gly Ser Val Asn Gly Tyr Gln Ser Ala Ile Gly Pro Gly Ile
1               5                   10                  15

Asn Tyr Glu Thr Val Ser Gln Val Asp Glu Phe Cys Lys Ala Leu Gly
            20              25                  30

```
Gly Lys Arg Pro Ile His Ser Ile Leu Ile Ala Asn Asn Gly Met Ala
            35                  40                  45

Ala Val Lys Phe Ile Arg Ser Val Arg Thr Trp Ala Tyr Glu Thr Phe
 50                  55                  60

Gly Thr Glu Lys Ala Ile Leu Leu Val Gly Met Ala Thr Pro Glu Asp
 65                  70                  75                  80

Met Arg Ile Asn Ala Glu His Ile Arg Ile Ala Asp Gln Phe Val Glu
                85                  90                  95

Val Pro Gly Gly Thr Asn Asn Asn Tyr Ala Asn Val Gln Leu Ile
                100                 105                 110

Val Glu Met Ala Glu Val Thr Arg Val Asp Ala Val Trp Pro Gly Trp
                115                 120                 125

Gly His Ala Ser Glu Asn Pro Glu Leu Pro Asp Ala Leu Asp Ala Lys
            130                 135                 140

Gly Ile Ile Phe Leu Gly Pro Pro Ala Ala Ser Met Ala Ala Leu Gly
145                 150                 155                 160

Asp Lys Ile Gly Ser Ser Leu Ile Ala Gln Ala Ala Asp Val Pro Thr
                165                 170                 175

Leu Pro Trp Ser Gly Ser His Val Lys Met Pro Pro Asn Ser Asn Leu
            180                 185                 190

Val Thr Ile Pro Glu Glu Ile Tyr
            195                 200

<210> SEQ ID NO 305
<211> LENGTH: 200
<212> TYPE: PRT
<213> ORGANISM: Camelina sativa

<400> SEQUENCE: 305

Met Ala Gly Ser Val Asn Gly Tyr Gln Ser Ala Val Gly Pro Gly Ile
  1               5                  10                  15

Asn Tyr Glu Ser Val Ser Gln Val Asp Glu Phe Cys Lys Ala Leu Gly
                20                  25                  30

Gly Lys Arg Pro Ile His Ser Ile Leu Ile Ala Asn Asn Gly Met Ala
            35                  40                  45

Ala Val Lys Phe Ile Arg Ser Val Arg Thr Trp Ala Tyr Glu Thr Phe
 50                  55                  60

Gly Thr Glu Lys Ala Ile Leu Leu Val Gly Met Ala Thr Pro Glu Asp
 65                  70                  75                  80

Met Arg Ile Asn Ala Glu His Ile Arg Ile Ala Asp Gln Phe Val Glu
                85                  90                  95

Val Pro Gly Gly Thr Asn Asn Asn Tyr Ala Asn Val Gln Leu Ile
                100                 105                 110

Val Glu Met Ala Glu Val Thr Arg Val Asp Ala Val Trp Pro Gly Trp
                115                 120                 125

Gly His Ala Ser Glu Asn Pro Glu Leu Pro Asp Ala Leu Asp Ala Lys
            130                 135                 140

Gly Ile Ile Phe Leu Gly Pro Pro Ala Ala Ser Met Gly Ala Leu Gly
145                 150                 155                 160

Asp Lys Ile Gly Ser Ser Leu Ile Ala Gln Ala Ala Asp Val Pro Thr
                165                 170                 175

Leu Pro Trp Ser Gly Ser His Val Lys Ile Pro Pro Asn Ser Asn Leu
            180                 185                 190

Val Thr Ile Pro Glu Glu Ile Tyr
```

-continued

```
                    195                 200

<210> SEQ ID NO 306
<211> LENGTH: 200
<212> TYPE: PRT
<213> ORGANISM: Camelina sativa

<400> SEQUENCE: 306

Met Ala Gly Ser Val Asn Gly Tyr Gln Ser Ala Val Gly Pro Gly Ile
1               5                   10                  15

Asn Tyr Glu Thr Val Ser Gln Val Asp Glu Phe Cys Lys Ala Leu Gly
            20                  25                  30

Gly Asn Arg Pro Ile His Ser Ile Leu Ile Ala Asn Asn Gly Met Ala
        35                  40                  45

Ala Val Lys Phe Ile Arg Ser Val Arg Thr Trp Ala Tyr Glu Thr Phe
    50                  55                  60

Gly Thr Glu Lys Ala Ile Leu Leu Val Gly Met Ala Thr Pro Glu Asp
65                  70                  75                  80

Met Arg Ile Asn Ala Glu His Ile Arg Ile Ala Asp Gln Phe Val Glu
                85                  90                  95

Val Pro Gly Gly Thr Asn Asn Asn Asn Tyr Ala Asn Val Gln Leu Ile
            100                 105                 110

Val Glu Met Ala Glu Val Thr Arg Val Asp Ala Val Trp Pro Gly Trp
        115                 120                 125

Gly His Ala Ser Glu Asn Pro Glu Leu Pro Asp Ala Leu Asp Ala Lys
    130                 135                 140

Gly Ile Ile Phe Leu Gly Pro Pro Ala Ala Ser Met Gly Ala Leu Gly
145                 150                 155                 160

Asp Lys Ile Gly Ser Ser Leu Ile Ala Gln Ala Ala Asp Val Pro Thr
                165                 170                 175

Leu Pro Trp Ser Gly Ser His Val Lys Ile Pro Pro Asn Ser Asn Leu
            180                 185                 190

Val Thr Ile Pro Glu Glu Ile Tyr
        195                 200

<210> SEQ ID NO 307
<211> LENGTH: 200
<212> TYPE: PRT
<213> ORGANISM: Capsella rubella

<400> SEQUENCE: 307

Met Ala Gly Ser Val Asn Gly Tyr Gln Ser Ser Val Gly Pro Gly Ile
1               5                   10                  15

Asn Tyr Glu Thr Val Ser Gln Val Asp Glu Phe Cys Lys Ser Leu Gly
            20                  25                  30

Gly Lys Arg Pro Ile His Ser Ile Leu Ile Ala Asn Asn Gly Met Ala
        35                  40                  45

Ala Val Lys Phe Ile Arg Ser Val Arg Thr Trp Ala Tyr Glu Thr Phe
    50                  55                  60

Gly Thr Glu Lys Ala Ile Leu Leu Val Gly Met Ala Thr Pro Glu Asp
65                  70                  75                  80

Met Arg Ile Asn Ala Glu His Ile Arg Ile Ala Asp Gln Phe Val Glu
                85                  90                  95

Val Pro Gly Gly Thr Asn Asn Asn Asn Tyr Ala Asn Val Gln Leu Ile
            100                 105                 110

Val Glu Met Ala Glu Val Thr Arg Val Asp Ala Val Trp Pro Gly Trp
```

```
                    115                 120                 125
Gly His Ala Ser Glu Asn Pro Glu Leu Pro Asp Ala Leu Asp Ala Lys
            130                 135                 140

Gly Ile Ile Phe Leu Gly Pro Pro Ala Ala Ser Met Ala Ala Leu Gly
145                 150                 155                 160

Asp Lys Ile Gly Ser Ser Leu Ile Ala Gln Ala Ala Asp Val Pro Thr
                165                 170                 175

Leu Pro Trp Ser Gly Ser His Val Lys Ile Pro Pro Asn Ser Asn Leu
            180                 185                 190

Val Thr Ile Pro Glu Glu Ile Tyr
        195                 200

<210> SEQ ID NO 308
<211> LENGTH: 197
<212> TYPE: PRT
<213> ORGANISM: Brassica oleracea

<400> SEQUENCE: 308

Met Ala Gly Ser Val Asn Gly Tyr Gln Thr Pro Gly Arg Asn His Val
1               5                   10                  15

Ser Val Ser Glu Val Asp Asp Phe Cys Ile Ala Leu Gly Gly Lys Arg
            20                  25                  30

Pro Ile His Ser Ile Leu Ile Ala Asn Asn Gly Met Ala Ala Val Lys
        35                  40                  45

Phe Ile Arg Ser Val Arg Thr Trp Ala Tyr Glu Thr Phe Gly Thr Glu
    50                  55                  60

Arg Ala Ile Leu Leu Val Gly Met Ala Thr Pro Glu Asp Met Arg Ile
65                  70                  75                  80

Asn Ala Glu His Ile Arg Ile Ala Asp Gln Phe Val Glu Val Pro Gly
                85                  90                  95

Gly Thr Asn Asn Asn Asn Tyr Ala Asn Val Gln Leu Ile Val Glu Met
            100                 105                 110

Ala Glu Val Thr Arg Val Asp Ala Val Trp Pro Gly Trp Gly His Ala
        115                 120                 125

Ser Glu Asn Pro Glu Leu Pro Asp Ala Leu Lys Ala Lys Gly Ile Ile
    130                 135                 140

Phe Leu Gly Pro Pro Ala Ala Ser Met Ala Ala Leu Gly Asp Lys Ile
145                 150                 155                 160

Gly Ser Ser Leu Ile Ala Gln Ala Ala Asp Val Pro Thr Leu Pro Trp
                165                 170                 175

Ser Gly Ser His Val Lys Ile Pro Pro Asp Ser Ser Leu Val Thr Ile
            180                 185                 190

Pro Glu Glu Ile Tyr
        195

<210> SEQ ID NO 309
<211> LENGTH: 197
<212> TYPE: PRT
<213> ORGANISM: Brassica napus

<400> SEQUENCE: 309

Met Ala Gly Ser Val Asn Gly Tyr Gln Thr Pro Gly Arg Asn His Val
1               5                   10                  15

Ser Val Ser Glu Val Asp Asp Phe Cys Ile Ala Leu Gly Gly Lys Arg
            20                  25                  30

Pro Ile His Ser Ile Leu Ile Ala Asn Asn Gly Met Ala Ala Val Lys
```

```
            35                  40                  45
Phe Ile Arg Ser Val Arg Thr Trp Ala Tyr Glu Thr Phe Gly Thr Glu
 50                  55                  60

Arg Ala Ile Leu Leu Val Gly Met Ala Thr Pro Glu Asp Met Arg Ile
 65                  70                  75                  80

Asn Ala Glu His Ile Arg Ile Ala Asp Gln Phe Val Glu Val Pro Gly
                 85                  90                  95

Gly Thr Asn Asn Asn Tyr Ala Asn Val Gln Leu Ile Val Glu Met
                100                 105                 110

Ala Glu Val Thr Arg Val Asp Ala Val Trp Pro Gly Trp Gly His Ala
                115                 120                 125

Ser Glu Asn Pro Glu Leu Pro Asp Ala Leu Lys Ala Lys Gly Ile Ile
    130                 135                 140

Phe Leu Gly Pro Pro Ala Ala Ser Met Ala Ala Leu Gly Asp Lys Ile
145                 150                 155                 160

Gly Ser Ser Leu Ile Ala Gln Ala Ala Asp Val Pro Thr Leu Pro Trp
                165                 170                 175

Ser Gly Ser His Val Lys Ile Pro Pro Asp Ser Ser Leu Val Thr Ile
                180                 185                 190

Pro Glu Glu Ile Tyr
                195

<210> SEQ ID NO 310
<211> LENGTH: 197
<212> TYPE: PRT
<213> ORGANISM: Brassica napus

<400> SEQUENCE: 310

Met Ala Gly Ser Val Asn Gly Tyr Gln Thr Pro Gly Arg Asn His Val
 1               5                  10                  15

Ser Val Ser Glu Val Asp Asp Phe Cys Ile Ala Leu Gly Gly Lys Arg
                20                  25                  30

Pro Ile His Ser Ile Leu Ile Ala Asn Asn Gly Met Ala Ala Val Lys
                35                  40                  45

Phe Ile Arg Ser Val Arg Thr Trp Ala Tyr Glu Thr Phe Gly Thr Glu
 50                  55                  60

Arg Ala Ile Leu Leu Val Gly Met Ala Thr Pro Glu Asp Met Arg Ile
 65                  70                  75                  80

Asn Ala Glu His Ile Arg Ile Ala Asp Gln Phe Val Glu Val Pro Gly
                 85                  90                  95

Gly Thr Asn Asn Asn Tyr Ala Asn Val Gln Leu Ile Val Glu Met
                100                 105                 110

Ala Glu Val Thr Arg Val Asp Ala Val Trp Pro Gly Trp Gly His Ala
                115                 120                 125

Ser Glu Asn Pro Glu Leu Pro Asp Ala Leu Lys Ala Lys Gly Ile Ile
    130                 135                 140

Phe Leu Gly Pro Pro Ala Ala Ser Met Ala Ala Leu Gly Asp Lys Ile
145                 150                 155                 160

Gly Ser Ser Leu Ile Ala Gln Ala Ala Asp Val Pro Thr Leu Pro Trp
                165                 170                 175

Ser Gly Ser His Val Lys Ile Pro Pro Asp Ser Ser Leu Val Thr Ile
                180                 185                 190

Pro Glu Glu Ile Tyr
                195
```

```
<210> SEQ ID NO 311
<211> LENGTH: 197
<212> TYPE: PRT
<213> ORGANISM: Brassica rapa

<400> SEQUENCE: 311

Met Ala Gly Ser Val Asn Gly Tyr Gln Thr Pro Gly Arg Asn His Val
1               5                   10                  15

Ser Val Ser Glu Val Asp Asp Phe Cys Ile Ala Leu Gly Gly Lys Arg
            20                  25                  30

Pro Ile His Ser Ile Leu Ile Ala Asn Asn Gly Met Ala Ala Val Lys
        35                  40                  45

Phe Ile Arg Ser Val Arg Thr Trp Ala Tyr Glu Thr Phe Gly Thr Glu
50                  55                  60

Arg Ala Ile Leu Leu Val Gly Met Ala Thr Pro Glu Asp Met Arg Ile
65                  70                  75                  80

Asn Ala Glu His Ile Arg Ile Ala Asp Gln Phe Val Glu Val Pro Gly
                85                  90                  95

Gly Thr Asn Asn Asn Asn Tyr Ala Asn Val Gln Leu Ile Val Glu Met
            100                 105                 110

Ala Glu Val Thr Arg Val Asp Ala Val Trp Pro Gly Trp Gly His Ala
        115                 120                 125

Ser Glu Asn Pro Glu Leu Pro Asp Ala Leu Lys Ala Lys Gly Ile Ile
    130                 135                 140

Phe Leu Gly Pro Pro Ala Ala Ser Met Ala Ala Leu Gly Asp Lys Ile
145                 150                 155                 160

Gly Ser Ser Leu Ile Ala Gln Ala Ala Asp Val Pro Thr Leu Pro Trp
                165                 170                 175

Ser Gly Ser His Val Lys Ile Pro Pro Asp Ser Ser Leu Val Thr Ile
            180                 185                 190

Pro Glu Glu Ile Tyr
        195

<210> SEQ ID NO 312
<211> LENGTH: 197
<212> TYPE: PRT
<213> ORGANISM: Artificial Sequence
<220> FEATURE:
<223> OTHER INFORMATION: consensus sequence
<220> FEATURE:
<221> NAME/KEY: SITE
<222> LOCATION: (20)..(20)
<223> OTHER INFORMATION: Xaa is any one of N, D, Q, E, B, and Z.
<220> FEATURE:
<221> NAME/KEY: SITE
<222> LOCATION: (23)..(23)
<223> OTHER INFORMATION: Xaa is any one of N, D, Q, E, B, and Z.
<220> FEATURE:
<221> NAME/KEY: SITE
<222> LOCATION: (186)..(186)
<223> OTHER INFORMATION: Xaa is any one of N, D, Q, E, B, and Z.

<400> SEQUENCE: 312

Met Ala Gly Ser Val Asn Gly Tyr Gln Thr Pro Gly Arg Asn His Val
1               5                   10                  15

Ser Val Ser Xaa Val Asp Xaa Phe Cys Ile Ala Leu Gly Gly Lys Arg
            20                  25                  30

Pro Ile His Ser Ile Leu Ile Ala Asn Asn Gly Met Ala Ala Val Lys
        35                  40                  45

Phe Ile Arg Ser Val Arg Thr Trp Ala Tyr Glu Thr Phe Gly Thr Glu
```

```
Arg Ala Ile Leu Leu Val Gly Met Ala Thr Pro Glu Asp Met Arg Ile
 65                  70                  75                  80

Asn Ala Glu His Ile Arg Ile Ala Asp Gln Phe Val Glu Val Pro Gly
                 85                  90                  95

Gly Thr Asn Asn Asn Tyr Ala Asn Val Gln Leu Ile Val Glu Met
            100                 105                 110

Ala Glu Val Thr Arg Val Asp Ala Val Trp Pro Gly Trp Gly His Ala
            115                 120                 125

Ser Glu Asn Pro Glu Leu Pro Asp Ala Leu Lys Ala Lys Gly Ile Ile
            130                 135                 140

Phe Leu Gly Pro Pro Ala Ala Ser Met Ala Ala Leu Gly Asp Lys Ile
145                 150                 155                 160

Gly Ser Ser Leu Ile Ala Gln Ala Ala Asp Val Pro Thr Leu Pro Trp
                165                 170                 175

Ser Gly Ser His Val Lys Ile Pro Pro Xaa Ser Ser Leu Val Thr Ile
                180                 185                 190

Pro Glu Glu Ile Tyr
            195

<210> SEQ ID NO 313
<211> LENGTH: 279
<212> TYPE: PRT
<213> ORGANISM: Arabidopsis thaliana

<400> SEQUENCE: 313

Met Glu Met Arg Ala Leu Gly Ser Ser Cys Ser Thr Gly Asn Gly Gly
  1               5                  10                  15

Ser Ala Pro Ile Thr Leu Thr Asn Ile Ser Pro Trp Ile Thr Thr Val
                 20                  25                  30

Phe Pro Ser Thr Val Lys Leu Arg Ser Ser Leu Arg Thr Phe Lys Gly
             35                  40                  45

Val Ser Ser Arg Val Arg Thr Phe Lys Gly Val Ser Ser Thr Arg Val
 50                  55                  60

Leu Ser Arg Thr Lys Gln Gln Phe Pro Leu Phe Cys Phe Leu Asn Pro
 65                  70                  75                  80

Asp Pro Ile Ser Phe Leu Glu Asn Asp Val Ser Glu Ala Glu Arg Thr
                 85                  90                  95

Val Val Leu Pro Asp Gly Ser Val Asn Gly Ala Gly Ser Val Asn Gly
            100                 105                 110

Tyr His Ser Asp Val Val Pro Gly Arg Asn Val Ala Glu Val Asn Glu
            115                 120                 125

Phe Cys Lys Ala Leu Gly Gly Lys Arg Pro Ile His Ser Ile Leu Val
            130                 135                 140

Ala Thr Asn Gly Met Ala Ala Val Lys Phe Ile Arg Ser Val Arg Thr
145                 150                 155                 160

Trp Ala Tyr Glu Thr Phe Gly Ser Glu Lys Ala Val Lys Leu Val Ala
                165                 170                 175

Met Ala Thr Pro Glu Asp Met Arg Ile Asn Ala Glu His Ile Arg Ile
            180                 185                 190

Ala Asp Gln Phe Val Glu Val Pro Gly Gly Thr Asn Asn Asn Asn Tyr
            195                 200                 205

Ala Asn Val Gln Leu Ile Val Glu Met Ala Glu Val Thr Arg Val Asp
            210                 215                 220
```

```
Ala Val Trp Pro Gly Trp Gly His Ala Ser Glu Asn Pro Glu Leu Pro
225                 230                 235                 240

Asp Ala Leu Lys Glu Lys Gly Ile Ile Phe Leu Gly Pro Pro Ala Asp
                245                 250                 255

Ser Met Ile Ala Leu Gly Asp Lys Ile Gly Ser Ser Leu Ile Ala Gln
            260                 265                 270

Ala Ala Asp Val Pro Thr Leu
        275

<210> SEQ ID NO 314
<211> LENGTH: 282
<212> TYPE: PRT
<213> ORGANISM: Arabidopsis lyrata

<400> SEQUENCE: 314

Met Glu Met Arg Ala Leu Val Ser Ser Cys Ala Thr Gly Asn Gly Gly
1               5                   10                  15

Ser Asp Pro Phe Ser Phe Thr Lys Val Ser Pro Trp Ile Thr Thr Val
            20                  25                  30

Gly Gly Lys Asp Arg Asp Phe Pro Thr Thr Val Lys Leu Arg Thr Ser
        35                  40                  45

Met Arg Thr Phe Lys Gly Val Ser Ile Arg Gly Arg Thr Phe Lys Gly
    50                  55                  60

Val Ser Thr Arg Val Leu Ser Arg Asn Lys Gln Gln Phe Pro Leu Phe
65                  70                  75                  80

Cys Phe Leu Asn Pro Asp Pro Thr Ser Phe Arg Asp Asn Asp Ile Ser
                85                  90                  95

Glu Ala Gln Arg Thr Val Val Leu Pro Gly Gly Ser Val Asn Gly Tyr
            100                 105                 110

His Gln Ser Glu Val Val Pro Gly Arg Asn Asp Gly Thr Val Ala Glu
        115                 120                 125

Val Asp Glu Phe Cys Lys Ala Leu Gly Gly Lys Arg Pro Ile His Ser
    130                 135                 140

Ile Leu Val Ala Thr Asn Gly Met Ala Ala Val Lys Phe Ile Arg Ser
145                 150                 155                 160

Ile Arg Thr Trp Ala Tyr Glu Thr Phe Gly Thr Glu Lys Ala Val Lys
                165                 170                 175

Leu Val Ala Met Ala Thr Pro Glu Asp Met Arg Ile Asn Ala Glu His
            180                 185                 190

Ile Arg Ile Ala Asp Gln Phe Val Glu Val Pro Gly Gly Thr Asn Asn
        195                 200                 205

Asn Asn Tyr Ala Asn Val Gln Leu Ile Val Glu Met Ala Glu Val Thr
    210                 215                 220

Arg Val Asp Ala Val Trp Pro Gly Trp Gly His Ala Ser Glu Asn Pro
225                 230                 235                 240

Glu Leu Pro Asp Ala Leu Lys Ala Lys Gly Ile Ile Phe Leu Gly Pro
                245                 250                 255

Pro Ala Ala Ser Met Ile Ala Leu Gly Asp Lys Ile Gly Ser Ser Leu
            260                 265                 270

Ile Ala Gln Ala Ala Asp Val Pro Thr Leu
        275                 280

<210> SEQ ID NO 315
<211> LENGTH: 280
<212> TYPE: PRT
<213> ORGANISM: Camelina sativa
```

<400> SEQUENCE: 315

Met Glu Met Arg Ala Leu Val Ser Ser Tyr Ser Thr Gly Asn Gly Gly
1               5                   10                  15

Ser Asp Pro Ile Ser Leu Thr Asn Gly Ser Pro Trp Ile Thr Thr Val
            20                  25                  30

Gly Gly Gly Ala Ser Thr Met Asp Arg Glu Phe Pro Leu Thr Val Lys
        35                  40                  45

Leu Gly Ser Ser Met Arg Ala Phe Lys Gly Val Ser Thr Thr Thr Val
    50                  55                  60

Leu Ser Arg Thr Lys Gln Gln Phe Pro Leu Val Cys Leu Ala Arg Asn
65                  70                  75                  80

Asn Ala Asn Ser Thr Asp Pro Thr Ser Phe Trp Glu Asn Asp Ile Ser
                85                  90                  95

Glu Val Gln Arg Thr Val Leu Pro Ala Glu Ser Ile Asn Gly Asp Lys
            100                 105                 110

Ser Ala Val Glu Pro Gly Arg Asn Asp Val Thr Val Ser Glu Val Asp
        115                 120                 125

Glu Phe Cys Lys Ala Leu Gly Gly Lys Arg Pro Ile His Ser Ile Leu
130                 135                 140

Val Ala Thr Asn Gly Met Ala Ser Val Lys Phe Ile Arg Ser Ile Arg
145                 150                 155                 160

Thr Trp Ala Tyr Gln Thr Phe Gly Ser Glu Lys Ala Ile Ser Leu Val
                165                 170                 175

Ala Met Ala Thr Pro Glu Asp Met Arg Ile Asn Ala Glu His Ile Arg
            180                 185                 190

Ile Ala Asp Gln Phe Val Glu Val Pro Gly Gly Thr Asn Asn Asn Asn
        195                 200                 205

Tyr Ala Asn Val Gln Leu Ile Val Glu Met Ala Glu Ala Thr Arg Val
    210                 215                 220

Asp Ala Val Trp Pro Gly Trp Gly His Ala Ser Glu Asn Pro Glu Leu
225                 230                 235                 240

Pro Asp Ala Leu Lys Ala Lys Gly Ile Ile Phe Leu Gly Pro Pro Ala
                245                 250                 255

Thr Ser Met Val Ala Leu Gly Asp Lys Ile Gly Ser Ser Leu Ile Ala
            260                 265                 270

Gln Ala Ala Asp Val Pro Thr Leu
        275                 280

<210> SEQ ID NO 316
<211> LENGTH: 280
<212> TYPE: PRT
<213> ORGANISM: Camelina sativa

<400> SEQUENCE: 316

Met Glu Met Arg Ala Leu Val Ser Ser Cys Ser Thr Gly Asn Gly Gly
1               5                   10                  15

Ser Asp Pro Ile Ser Leu Thr Asn Gly Ser Pro Trp Ile Thr Thr Val
            20                  25                  30

Gly Gly Gly Ala Ser Thr Met Asp Arg Glu Phe Pro Ala Thr Val Lys
        35                  40                  45

Leu Gly Ser Ser Met Arg Ala Phe Lys Gly Val Ser Thr Ile Thr Val
    50                  55                  60

Leu Ser Arg Thr Lys Gln Gln Phe Pro Leu Val Cys Leu Ala Arg Asn
65                  70                  75                  80

```
Asn Gly Asn Ser Thr Asp Pro Thr Ser Phe Trp Glu Asn Asp Ile Ser
                85                  90                  95

Glu Thr Gln Arg Thr Val Leu Pro Ala Glu Ser Ile Asn Gly Asp Lys
            100                 105                 110

Ser Ala Val Glu Pro Gly Arg Asn Asp Val Thr Val Ser Glu Val Asp
        115                 120                 125

Glu Phe Cys Lys Ala Leu Gly Gly Lys Arg Pro Ile His Arg Ile Met
    130                 135                 140

Val Ala Thr Asn Gly Met Ala Ala Val Lys Phe Ile Arg Ser Ile Arg
145                 150                 155                 160

Thr Trp Ala Tyr Gln Thr Phe Gly Ser Glu Lys Ala Ile Ser Leu Val
                165                 170                 175

Ala Met Ala Thr Pro Glu Asp Met Arg Ile Asn Ala Glu His Ile Arg
            180                 185                 190

Ile Ala Asp Gln Phe Val Glu Val Pro Gly Gly Thr Asn Asn Asn Asn
        195                 200                 205

Tyr Ala Asn Val Gln Leu Ile Val Glu Met Ala Glu Ala Thr Arg Val
    210                 215                 220

Asp Ala Val Trp Pro Gly Trp Gly His Ala Ser Glu Asn Pro Glu Leu
225                 230                 235                 240

Pro Asp Ala Leu Lys Ala Lys Gly Ile Ile Phe Leu Gly Pro Pro Ala
                245                 250                 255

Thr Ser Met Val Ala Leu Gly Asp Lys Ile Gly Ser Ser Leu Ile Ala
            260                 265                 270

Gln Ala Ala Asp Val Pro Thr Leu
        275                 280

<210> SEQ ID NO 317
<211> LENGTH: 277
<212> TYPE: PRT
<213> ORGANISM: Capsella rubella

<400> SEQUENCE: 317

Met Glu Met Arg Ala Leu Val Ser Ser Cys Ser Thr Gly Asn Gly Gly
1               5                   10                  15

Ser Asp Pro Ile Ser Leu Thr Asn Val Ser Pro Trp Ile Thr Thr Val
            20                  25                  30

Gly Gly Gly Ala Ser Ser Ile Asp Arg Glu Phe Pro Thr Thr Val Lys
        35                  40                  45

Leu Gly Ser Ser Leu Arg Thr Phe Lys Gly Val Ser Ser Thr Thr Val
    50                  55                  60

Leu Ser Arg Thr Lys Gln Gln Phe Pro Leu Val Cys Leu Ala Arg Asn
65                  70                  75                  80

Asn Ala Asn Ser Thr Asp Pro Thr Leu Phe Trp Glu Asn Asp Ile Ser
                85                  90                  95

Glu Ala Gln Ser Thr Val Leu Pro Ser Gly Ser Asp Glu Ser Ala Val
            100                 105                 110

Val Pro Ser Gly Asn Asp Val Lys Val Ser Glu Val Asp Glu Phe Cys
        115                 120                 125

Lys Ala Leu Gly Gly Lys Arg Pro Ile His Ser Ile Leu Val Ala Thr
    130                 135                 140

Asn Gly Met Ala Ala Val Lys Phe Ile Arg Ser Ile Arg Thr Trp Ala
145                 150                 155                 160

Tyr Gln Thr Phe Gly Thr Glu Lys Ala Ile Leu Leu Val Ala Met Ala
```

```
                    165                 170                 175
Thr Pro Glu Asp Met Arg Ile Asn Ala Glu His Ile Arg Ile Ala Asp
                180                 185                 190

Gln Phe Val Glu Val Pro Gly Gly Thr Asn Asn His Asn Tyr Ala Asn
            195                 200                 205

Val Gln Leu Ile Val Glu Met Ala Glu Ala Ala Ser Val Asp Ala Val
        210                 215                 220

Trp Pro Gly Trp Gly His Ala Ser Glu Asn Pro Glu Leu Pro Asp Ala
225                 230                 235                 240

Leu Lys Ala Lys Gly Ile Ile Phe Leu Gly Pro Ser Ala Ala Ser Met
                245                 250                 255

Val Ala Leu Gly Asp Lys Ile Gly Ser Ser Leu Ile Ala Gln Ala Ala
            260                 265                 270

Asp Val Pro Thr Leu
            275

<210> SEQ ID NO 318
<211> LENGTH: 276
<212> TYPE: PRT
<213> ORGANISM: Brassica oleracea

<400> SEQUENCE: 318

Met Glu Met Arg Ala Leu Val Ser Cys Ser Ala Gly Asn Gly Ala
1               5                   10                  15

Ser Asp Arg Phe Arg Leu Ser Asn Val Ser Pro Trp Ile Thr Ser Ala
                20                  25                  30

Arg Gly Ala Ser Gly Ser Asp Ser Pro Ala Thr Val Lys Leu Arg Ser
            35                  40                  45

Ser Ser Met Ile Arg Ala Phe Lys Gly Val Ser Ile Tyr Lys Asn Lys
        50                  55                  60

Thr Arg Arg Asn Val Leu Ser Gln Arg Asn Lys Gln Phe Arg Pro Met
65                  70                  75                  80

Ala Tyr Leu Gly Arg Lys Asp Leu Ser Ser Pro Asp Pro Thr Ser Phe
                85                  90                  95

Cys Asp Asn Asp Ile Ser Glu Pro Gln Gly Thr Gly Ser Ile Asn Gly
            100                 105                 110

Asn Asp His Ser Ala Val Arg Val Ser Gln Val Asp Glu Phe Cys Lys
        115                 120                 125

Ala His Gly Gly Lys Arg Pro Ile His Ser Ile Leu Val Ala Thr Asn
130                 135                 140

Gly Met Ala Ala Val Lys Leu Ile Arg Ser Val Arg Ala Trp Ser Cys
                145                 150                 155                 160

Gln Thr Phe Gly Ser Glu Lys Ser Ile Ser Leu Val Ala Met Ala Thr
                165                 170                 175

Pro Glu Asp Met Arg Ile Asn Ala Glu His Ile Arg Ile Ala Asp Gln
            180                 185                 190

Phe Met Gln Val Pro Gly Gly Thr Asn Asn Asn Tyr Ala Asn Val
        195                 200                 205

His Leu Ile Val Glu Met Ala Gln Ala Thr Gly Val Asp Ala Val Trp
    210                 215                 220

Pro Gly Trp Gly His Ala Ser Glu Asn Pro Glu Leu Pro Asp Ala Leu
225                 230                 235                 240

Lys Ala Lys Gly Val Ile Phe Leu Gly Pro Thr Ala Ala Ser Met Leu
                245                 250                 255
```

Ala Leu Gly Asp Lys Ile Gly Ser Ser Leu Ile Ala Gln Ala Ala Asp
            260                 265                 270

Val Pro Thr Leu
        275

<210> SEQ ID NO 319
<211> LENGTH: 276
<212> TYPE: PRT
<213> ORGANISM: Brassica napus

<400> SEQUENCE: 319

Met Glu Met Arg Ala Leu Val Ser Cys Ser Ala Gly Asn Gly Ala
1               5                   10                  15

Ser Asp Arg Phe Arg Leu Ser Asn Val Ser Pro Trp Ile Thr Ser Ala
                20                  25                  30

Arg Gly Ala Ser Gly Ser Asp Ser Pro Ala Thr Val Lys Leu Gly Ser
            35                  40                  45

Ser Ser Met Ile Arg Ala Phe Lys Gly Val Ser Ile Tyr Lys Asn Lys
        50                  55                  60

Thr Arg Arg Asn Val Leu Ser Gln Arg Asn Lys Gln Phe Arg Pro Met
65                  70                  75                  80

Ala Tyr Leu Gly Arg Lys Asp Leu Ser Ser Pro Asp Pro Thr Ser Phe
                85                  90                  95

Cys Asp Asn Asp Ile Ser Glu Pro Gln Gly Thr Gly Ser Ile Asn Gly
            100                 105                 110

Asn Asp His Ser Ala Val Arg Val Ser Gln Val Asp Glu Phe Cys Lys
        115                 120                 125

Ala His Gly Gly Lys Arg Pro Ile His Ser Ile Leu Val Ala Thr Asn
130                 135                 140

Gly Met Ala Ala Val Lys Leu Ile Arg Ser Val Arg Ala Trp Ser Tyr
145                 150                 155                 160

Gln Thr Phe Gly Ser Glu Lys Ser Ile Ser Leu Val Ala Met Ala Thr
                165                 170                 175

Pro Glu Asp Met Arg Ile Asn Ala Glu His Ile Arg Ile Ala Asp Gln
            180                 185                 190

Phe Met Gln Val Pro Gly Gly Thr Asn Asn Asn Asn Tyr Ala Asn Val
        195                 200                 205

His Leu Ile Val Glu Met Ala Gln Ala Thr Gly Val Asp Ala Val Trp
210                 215                 220

Pro Gly Trp Gly His Ala Ser Glu Asn Pro Glu Leu Pro Asp Ala Leu
225                 230                 235                 240

Lys Ala Lys Gly Val Ile Phe Leu Gly Pro Thr Ala Ala Ser Met Leu
                245                 250                 255

Ala Leu Gly Asp Lys Ile Gly Ser Ser Leu Ile Ala Gln Ala Ala Asp
            260                 265                 270

Val Pro Thr Leu
        275

<210> SEQ ID NO 320
<211> LENGTH: 276
<212> TYPE: PRT
<213> ORGANISM: Brassica napus

<400> SEQUENCE: 320

Met Glu Met Arg Ala Leu Val Ser Cys Ser Ala Gly Asn Gly Ala
1               5                   10                  15

Ser Asp Arg Phe Arg Leu Ser Asn Val Ser Pro Trp Ile Thr Ser Ala
                20                  25                  30

Arg Gly Ala Ser Gly Ser Asp Ser Pro Ala Thr Val Lys Leu Gly Ser
            35                  40                  45

Ser Ser Met Ile Arg Ala Phe Lys Gly Val Ser Ile Tyr Lys Asn Lys
        50                  55                  60

Thr Arg Arg Asn Val Leu Ser Gln Arg Asn Lys Gln Phe Arg Pro Met
65                  70                  75                  80

Ala Tyr Leu Gly Arg Lys Asp Leu Ser Ser Pro Asp Pro Thr Ser Phe
                85                  90                  95

Cys Asp Asn Asp Ile Ser Glu Pro Gln Gly Thr Gly Ser Ile Asn Gly
            100                 105                 110

Asn Asp His Ser Ala Val Arg Val Ser Gln Val Asp Glu Phe Cys Lys
        115                 120                 125

Ala His Gly Gly Lys Arg Pro Ile His Arg Ile Leu Val Ala Thr Asn
130                 135                 140

Gly Met Ala Ala Val Lys Phe Ile Arg Ser Val Arg Ala Trp Ser Tyr
145                 150                 155                 160

Gln Thr Phe Gly Ser Glu Lys Ser Ile Ser Leu Val Ala Met Ala Thr
                165                 170                 175

Pro Glu Asp Met Arg Ile Asn Ala Glu His Ile Arg Ile Ala Asp Gln
            180                 185                 190

Phe Met Gln Val Pro Gly Gly Thr Asn Asn Asn Tyr Ala Asn Val
        195                 200                 205

His Leu Ile Val Glu Met Ala Glu Ala Thr Gly Val Asp Ala Val Trp
210                 215                 220

Pro Gly Trp Gly His Ala Ser Glu Asn Pro Glu Leu Pro Asp Ala Leu
225                 230                 235                 240

Lys Ala Lys Gly Val Ile Phe Leu Gly Pro Thr Ala Ala Ser Met Leu
                245                 250                 255

Ala Leu Gly Asp Lys Ile Gly Ser Ser Leu Ile Ala Gln Ala Ala Asp
            260                 265                 270

Val Pro Thr Leu
        275

<210> SEQ ID NO 321
<211> LENGTH: 276
<212> TYPE: PRT
<213> ORGANISM: Brassica rapa

<400> SEQUENCE: 321

Met Glu Met Arg Ala Leu Val Ser Cys Ser Ala Ala Gly Asn Gly Ala
1               5                   10                  15

Ser Asp Arg Phe Arg Leu Ser Asn Val Ser Pro Trp Ile Thr Ser Ala
                20                  25                  30

Arg Gly Ala Ser Gly Ser Asp Ser Pro Ala Thr Val Lys Leu Gly Ser
            35                  40                  45

Ser Ser Met Ile Arg Ala Phe Lys Gly Val Ser Ile Tyr Lys Asn Lys
        50                  55                  60

Ser Arg Arg Asn Val Leu Ser Gln Arg Asn Lys Gln Phe Arg Pro Met
65                  70                  75                  80

Ala Tyr Leu Gly Arg Lys Asp Leu Ser Ser Pro Asp Pro Thr Ser Phe
                85                  90                  95

Cys Asp Asn Asp Ile Ser Glu Pro Gln Gly Thr Gly Ser Ile Asn Gly
            100                 105                 110

```
Asn Asp His Ser Ala Val Arg Val Ser Gln Val Asp Glu Phe Cys Lys
        115                 120                 125

Ala His Gly Gly Lys Arg Pro Ile His Arg Ile Leu Val Ala Thr Asn
    130                 135                 140

Gly Met Ala Ala Val Lys Phe Ile Arg Ser Val Arg Ala Trp Ser Tyr
145                 150                 155                 160

Gln Thr Phe Gly Ser Glu Lys Ser Ile Ser Leu Val Ala Met Ala Thr
                165                 170                 175

Pro Glu Asp Met Arg Ile Asn Ala Glu His Ile Arg Ile Ala Asp Gln
                180                 185                 190

Phe Met Gln Val Pro Gly Gly Thr Asn Asn Asn Tyr Ala Asn Val
                195                 200                 205

His Leu Ile Val Glu Met Ala Glu Ala Thr Gly Val Asp Ala Val Trp
    210                 215                 220

Pro Gly Trp Gly His Ala Ser Glu Asn Pro Glu Leu Pro Asp Ala Leu
225                 230                 235                 240

Lys Ala Lys Gly Val Ile Phe Leu Gly Pro Thr Ala Ala Ser Met Leu
                245                 250                 255

Ala Leu Gly Asp Lys Ile Gly Ser Ser Leu Ile Ala Gln Ala Ala Asp
                260                 265                 270

Val Pro Thr Leu
        275

<210> SEQ ID NO 322
<211> LENGTH: 254
<212> TYPE: PRT
<213> ORGANISM: Artificial Sequence
<220> FEATURE:
<223> OTHER INFORMATION: consensus sequence
<220> FEATURE:
<221> NAME/KEY: SITE
<222> LOCATION: (62)..(62)
<223> OTHER INFORMATION: Xaa is L or M.
<220> FEATURE:
<221> NAME/KEY: SITE
<222> LOCATION: (73)..(73)
<223> OTHER INFORMATION: Xaa is any one of N, D, Q, E, B, and Z.
<220> FEATURE:
<221> NAME/KEY: SITE
<222> LOCATION: (76)..(76)
<223> OTHER INFORMATION: Xaa is I or V.
<220> FEATURE:
<221> NAME/KEY: SITE
<222> LOCATION: (79)..(79)
<223> OTHER INFORMATION: Xaa is any one of N, D, Q, E, B, and Z.
<220> FEATURE:
<221> NAME/KEY: SITE
<222> LOCATION: (101)..(101)
<223> OTHER INFORMATION: Xaa is any one of N, D, Q, E, B, and Z.
<220> FEATURE:
<221> NAME/KEY: SITE
<222> LOCATION: (103)..(103)
<223> OTHER INFORMATION: Xaa is any one of N, D, Q, E, B, and Z.
<220> FEATURE:
<221> NAME/KEY: SITE
<222> LOCATION: (134)..(134)
<223> OTHER INFORMATION: Xaa is I or V.
<220> FEATURE:
<221> NAME/KEY: SITE
<222> LOCATION: (140)..(140)
<223> OTHER INFORMATION: Xaa is any one of N, D, Q, E, B, and Z.
<220> FEATURE:
<221> NAME/KEY: SITE
<222> LOCATION: (148)..(148)
<223> OTHER INFORMATION: Xaa is I or V.
<220> FEATURE:
<221> NAME/KEY: SITE
```

```
<222> LOCATION: (174)..(174)
<223> OTHER INFORMATION: Xaa is any one of N, D, Q, E, B, and Z.
<220> FEATURE:
<221> NAME/KEY: SITE
<222> LOCATION: (195)..(195)
<223> OTHER INFORMATION: Xaa is any one of N, D, Q, E, B, and Z.
<220> FEATURE:
<221> NAME/KEY: SITE
<222> LOCATION: (224)..(224)
<223> OTHER INFORMATION: Xaa is I or V.

<400> SEQUENCE: 322

Met Glu Met Arg Ala Leu Val Ser Ser Cys Ala Thr Gly Asn Gly Gly
1               5                   10                  15

Ser Asp Pro Phe Leu Thr Asn Val Ser Pro Trp Ile Thr Thr Val Gly
            20                  25                  30

Asp Phe Pro Thr Val Lys Leu Gly Ser Arg Ala Phe Lys Gly Val
        35                  40                  45

Ser Ile Lys Thr Val Leu Ser Arg Lys Gln Gln Phe Pro Xaa Cys Leu
    50                  55                  60

Arg Ser Pro Asp Pro Thr Ser Phe Xaa Asn Asp Xaa Ser Glu Xaa Arg
65                  70                  75                  80

Thr Val Leu Pro Gly Ser Ile Asn Gly Asp His Ser Ala Val Pro Gly
                85                  90                  95

Arg Asn Val Ser Xaa Val Xaa Glu Phe Cys Lys Ala Leu Gly Gly Lys
            100                 105                 110

Arg Pro Ile His Ser Ile Leu Val Ala Thr Asn Gly Met Ala Ala Val
        115                 120                 125

Lys Phe Ile Arg Ser Xaa Arg Thr Trp Ala Tyr Xaa Thr Phe Gly Ser
130                 135                 140

Glu Lys Ala Xaa Ser Leu Val Ala Met Ala Thr Pro Glu Asp Met Arg
145                 150                 155                 160

Ile Asn Ala Glu His Ile Arg Ile Ala Asp Gln Phe Val Xaa Val Pro
                165                 170                 175

Gly Gly Thr Asn Asn Asn Asn Tyr Ala Asn Val Gln Leu Ile Val Glu
            180                 185                 190

Met Ala Xaa Ala Thr Arg Val Asp Ala Val Trp Pro Gly Trp Gly His
        195                 200                 205

Ala Ser Glu Asn Pro Glu Leu Pro Asp Ala Leu Lys Ala Lys Gly Xaa
    210                 215                 220

Ile Phe Leu Gly Pro Pro Ala Ala Ser Met Ala Leu Gly Asp Lys Ile
225                 230                 235                 240

Gly Ser Ser Leu Ile Ala Gln Ala Ala Asp Val Pro Thr Leu
                245                 250

<210> SEQ ID NO 323
<211> LENGTH: 24
<212> TYPE: DNA
<213> ORGANISM: Artificial Sequence
<220> FEATURE:
<223> OTHER INFORMATION: oligonucleotide sequence

<400> SEQUENCE: 323
gcctcacgaa tatatctcca gttt                                          24

<210> SEQ ID NO 324
<211> LENGTH: 104
<212> TYPE: DNA
<213> ORGANISM: Artificial Sequence
<220> FEATURE:
```

<223> OTHER INFORMATION: the parental Ws/RLD sequence

<400> SEQUENCE: 324

```
atggagatga gagctttggg ttcttcgtgt tctactggta atggaggttc tgctccaatt    60
accctcacga atatatctcc atggatcaca acagtttttc cgtc                    104
```

<210> SEQ ID NO 325
<211> LENGTH: 105
<212> TYPE: DNA
<213> ORGANISM: Artificial Sequence
<220> FEATURE:
<223> OTHER INFORMATION: Ws-6-2

<400> SEQUENCE: 325

```
atggagatga aagctttggg ttcttcgtgt tctactggta atggaggttc tgctccaatt    60
accctcacga atatatcttc catggatcac aacagttttt ccgtc                   105
```

<210> SEQ ID NO 326
<211> LENGTH: 101
<212> TYPE: DNA
<213> ORGANISM: Artificial Sequence
<220> FEATURE:
<223> OTHER INFORMATION: RLD-6-2

<400> SEQUENCE: 326

```
atggagatga gagctttggg ttcttcgtgt tctactggta atggaggttc tgctccaatt    60
accctcacga atatatcttc catggatcac aacagttttt c                       101
```

<210> SEQ ID NO 327
<211> LENGTH: 105
<212> TYPE: DNA
<213> ORGANISM: Artificial Sequence
<220> FEATURE:
<223> OTHER INFORMATION: Ws-10-35

<400> SEQUENCE: 327

```
atggagatga gagctttggg ttcttcgtgt tctactggta atggaggttc tgctccaatt    60
accctcacga atatatcttc catggatcac aacagttttt ccgtc                   105
```

<210> SEQ ID NO 328
<211> LENGTH: 96
<212> TYPE: DNA
<213> ORGANISM: Artificial Sequence
<220> FEATURE:
<223> OTHER INFORMATION: Ws-11-5

<400> SEQUENCE: 328

```
atggagatga aagctttggg ttcttcgtgt tctactggta atggaggttc tgctccaatt    60
accctcacga atatggatca caacagtttt tccgtc                             96
```

<210> SEQ ID NO 329
<211> LENGTH: 105
<212> TYPE: DNA
<213> ORGANISM: Artificial Sequence
<220> FEATURE:
<223> OTHER INFORMATION: Ws-11-28

<400> SEQUENCE: 329

```
atggagatga gagctttggg ttcttcgtgt tctactggta atggaggttc tgctccaatt    60
accctcacga atatatcttc cagggatcac aacatttttt ccgcc                   105
```

-continued

```
<210> SEQ ID NO 330
<211> LENGTH: 105
<212> TYPE: DNA
<213> ORGANISM: Artificial Sequence
<220> FEATURE:
<223> OTHER INFORMATION: Ws-6-23

<400> SEQUENCE: 330
atggagatga aagctttggg ttcttcgtgt tctactggta atggaggttc tgctccaatt      60
accctcacga atatccctgc attggaacac attttctttc ccctc                     105

<210> SEQ ID NO 331
<211> LENGTH: 105
<212> TYPE: DNA
<213> ORGANISM: Artificial Sequence
<220> FEATURE:
<223> OTHER INFORMATION: Ws-6-11

<400> SEQUENCE: 331
atggagatga aagctttggg ttcttcgtgt tctactggta atggaggttc tgctccaatt      60
tccctcacca atggatctcc cctgttttc caccgttttt ccatc                      105

<210> SEQ ID NO 332
<211> LENGTH: 103
<212> TYPE: DNA
<213> ORGANISM: Artificial Sequence
<220> FEATURE:
<223> OTHER INFORMATION: Ws-6-9

<400> SEQUENCE: 332
atggagatga aagctttggg ttcttcgtgt tctactggta atggaggttc tgctccaatt      60
accctcacga atatatccca ggaaccaaaa aattttccc tcc                        103

<210> SEQ ID NO 333
<211> LENGTH: 94
<212> TYPE: DNA
<213> ORGANISM: Artificial Sequence
<220> FEATURE:
<223> OTHER INFORMATION: Ws-11-96

<400> SEQUENCE: 333
atggagatga gagctttggg ttcttcgtgt tctactggta atggaggttc tgctccaatt      60
accctcacga atatatcaca acagttttc cgtc                                  94

<210> SEQ ID NO 334
<211> LENGTH: 105
<212> TYPE: DNA
<213> ORGANISM: Artificial Sequence
<220> FEATURE:
<223> OTHER INFORMATION: Ws-6-19
<220> FEATURE:
<221> NAME/KEY: misc_feature
<222> LOCATION: (67)..(67)
<223> OTHER INFORMATION: n is a, c, g, or t

<400> SEQUENCE: 334
atggagatga aagctttggg ttcttcgtgt tctactggta atggaggttc tgctccaatt      60
accctcncga atatatcttc catggatcac aacagttttt ccgtc                     105

<210> SEQ ID NO 335
<211> LENGTH: 101
<212> TYPE: DNA
<213> ORGANISM: Artificial Sequence
<220> FEATURE:
```

<223> OTHER INFORMATION: RLD-10-25

<400> SEQUENCE: 335
atggagatga gagctttggg ttcttcgtgt tctactggta atggaggttc tgctccaatt        60
accctcacga atatatcttc catggatcac aacagttttt c        101

<210> SEQ ID NO 336
<211> LENGTH: 101
<212> TYPE: DNA
<213> ORGANISM: Artificial Sequence
<220> FEATURE:
<223> OTHER INFORMATION: RLD-6-10

<400> SEQUENCE: 336
atggagatga gagctttggg ttcttcgtgt tctactggta atggaggttc tgctccaatt        60
accctcacga atatatcttc catggatcac aacagttttt c        101

<210> SEQ ID NO 337
<211> LENGTH: 99
<212> TYPE: DNA
<213> ORGANISM: Artificial Sequence
<220> FEATURE:
<223> OTHER INFORMATION: RLD-10-2

<400> SEQUENCE: 337
atggagatga aagctttggg ttcttcgtgt tctactggta atggaggttc tgctccaatt        60
accctcacga atatatctaa tggatcacaa cagtttttc        99

<210> SEQ ID NO 338
<211> LENGTH: 101
<212> TYPE: DNA
<213> ORGANISM: Artificial Sequence
<220> FEATURE:
<223> OTHER INFORMATION: RLD-6-13

<400> SEQUENCE: 338
atggagatga gagctttggg ttcttcgtgt tctactggta atggaggttc tgctccaatt        60
accctcacga atatatcttc catggatcac aacagttttt c        101

<210> SEQ ID NO 339
<211> LENGTH: 101
<212> TYPE: DNA
<213> ORGANISM: Artificial Sequence
<220> FEATURE:
<223> OTHER INFORMATION: RLD-6-15

<400> SEQUENCE: 339
atggagatga gagctttggg ttcttcgtgt tctactggta atggaggttc tgctccaatt        60
accctcacga atatatcttc catggatcac aacagttttt c        101

<210> SEQ ID NO 340
<211> LENGTH: 98
<212> TYPE: DNA
<213> ORGANISM: Artificial Sequence
<220> FEATURE:
<223> OTHER INFORMATION: RLD-10-10

<400> SEQUENCE: 340
atggagatga gagctttggg ttcttcgtgt tctactggta atggaggttc tgctccaatt        60
accctcacga atatatccat ggatcacaac agttttttc        98

```
<210> SEQ ID NO 341
<211> LENGTH: 101
<212> TYPE: DNA
<213> ORGANISM: Artificial Sequence
<220> FEATURE:
<223> OTHER INFORMATION: RLD-6-6

<400> SEQUENCE: 341
atggagatga gagctttggg ttcttcgtgt tctactggta atggaggttc tgctccaatt    60
accctcacga atatatcttc catggatcac aacagttttt c                       101

<210> SEQ ID NO 342
<211> LENGTH: 98
<212> TYPE: DNA
<213> ORGANISM: Artificial Sequence
<220> FEATURE:
<223> OTHER INFORMATION: RLD-10-29

<400> SEQUENCE: 342
atggagatga gagctttggg ttcttcgtgt tctactggta atggaggttc tgctccaatt    60
accctcacga atatatccat ggatcacaac agttttttc                          98

<210> SEQ ID NO 343
<211> LENGTH: 101
<212> TYPE: DNA
<213> ORGANISM: Artificial Sequence
<220> FEATURE:
<223> OTHER INFORMATION: RLD-11-14
<220> FEATURE:
<221> NAME/KEY: misc_feature
<222> LOCATION: (94)..(94)
<223> OTHER INFORMATION: n is a, c, g, or t

<400> SEQUENCE: 343
atggagatga gagctttggg ttcttcgtgt tctactggta atggaggttc tgctccaatt    60
accctcacca agaatccctc catgttttcc aacnactttt c                       101

<210> SEQ ID NO 344
<211> LENGTH: 101
<212> TYPE: DNA
<213> ORGANISM: Artificial Sequence
<220> FEATURE:
<223> OTHER INFORMATION: RLD-10-8

<400> SEQUENCE: 344
atggagatga gagctttggg ttcttcgtgt tctactggta atggaggttc tgctccaatt    60
accctcacga atatatcctc ggaggatcac aattttttt c                        101

<210> SEQ ID NO 345
<211> LENGTH: 399
<212> TYPE: DNA
<213> ORGANISM: Artificial Sequence
<220> FEATURE:
<223> OTHER INFORMATION: N-terminal nucleotides of Brassica napus cv
      Darmor-bzh ACC2-Br: BnaA06g04070D

<400> SEQUENCE: 345
atggagatga gagctttggt ttcgtgttct gctgccggaa atggagcttc tgatcggttt    60
agactctcca atgtttcacc atggatcaca tcagctcgtg gtgcaagtgg cagtgactcc    120
ccagccacag tgaagctggg aagcagctct atgatcagag ccttcaaagg agtttcgatt    180
tacaaaaaca agaccagaag aaatgttttg tctcaaagga caaacagtt tcgtcctatg    240 gcctacttag gaaggaagga cttgagcagc cctgatccga cctccttctg cgataatgat    300
```

```
atatctgaac ctcaagggac tggatccatt aatgggaatg atcatagtgc tgtaagagtg    360
tctcaagtcg atgagttctg taaggctcac ggtggaaaa                            399

<210> SEQ ID NO 346
<211> LENGTH: 399
<212> TYPE: DNA
<213> ORGANISM: Artificial Sequence
<220> FEATURE:
<223> OTHER INFORMATION: N-terminal nucleotides of Brassica napus cv
      Darmor-bzh ACC2-Bo: BnaC06g01580D

<400> SEQUENCE: 346
atggagatga gagctttagt ttcgtgttct gctgccggaa atggagcttc tgatcggttt    60
agactctcca atgttccacc atggatcaca tcagctcgtg gtgcaagtgg cagtgactcc    120
ccagccacag tgaagctggg aagcagctct atgattagag ctttcaaagg agtttcgatt    180
tacaaaaaca agaccagaag gaatgttctg tctcaaagga acaaacagtt ccgtcctatg    240
gcctacttag gaaggaagga cttgagcagc cctgatccga cctccttctg cgataatgat    300
atatctgaac ctcaagggac cggatccatt aatgggaatg atcatagtgc tgtaagagtg    360
tctcaagtcg atgagttctg taaggctcat ggtggaaaa                            399

<210> SEQ ID NO 347
<211> LENGTH: 93
<212> TYPE: DNA
<213> ORGANISM: Artificial Sequence
<220> FEATURE:
<223> OTHER INFORMATION: N-terminal nucleotides of Brassica napus cv
      Darmor-bzh ACC1-Br: BnaA08g06180D

<400> SEQUENCE: 347
atggctggct ctgttaacgg gtatcaaact cccggtagaa atcatgtttc ggtgtctgaa    60
gtggatgact tttgcattgc acttggaggg aaa                                  93

<210> SEQ ID NO 348
<211> LENGTH: 93
<212> TYPE: DNA
<213> ORGANISM: Artificial Sequence
<220> FEATURE:
<223> OTHER INFORMATION: N-terminal nucleotides of Brassica napus cv
      Darmor-bzh ACC1-Bo: BnaC08g06560D

<400> SEQUENCE: 348
atggctggct ctgttaacgg gtatcaaact cccggtagaa atcatgtttc ggtgtctgaa    60
gtggatgact tttgcattgc acttggaggg aaa                                  93

<210> SEQ ID NO 349
<211> LENGTH: 22
<212> TYPE: DNA
<213> ORGANISM: Artificial Sequence
<220> FEATURE:
<223> OTHER INFORMATION: sgRNA-target

<400> SEQUENCE: 349
ggtttagact ctccaatgtt tc                                              22

<210> SEQ ID NO 350
<211> LENGTH: 22
<212> TYPE: DNA
<213> ORGANISM: Artificial Sequence
<220> FEATURE:
<223> OTHER INFORMATION: sgRNA-target
```

```
<400> SEQUENCE: 350
ggaaggaagg acttgagcag cc                                             22

<210> SEQ ID NO 351
<211> LENGTH: 22
<212> TYPE: DNA
<213> ORGANISM: Artificial Sequence
<220> FEATURE:
<223> OTHER INFORMATION: sgRNA-target

<400> SEQUENCE: 351
ttagactctc caatgtttca cc                                             22

<210> SEQ ID NO 352
<211> LENGTH: 298
<212> TYPE: DNA
<213> ORGANISM: Brassica napus

<400> SEQUENCE: 352
atggagatga gagctttagt ttcgtgttct gctgccggaa atggagcttc tgatcggttt     60
agactctcca atgtttcacc atggatcaca tcagctcgtg gtgcaagtgg cagtgactcc    120
ccagccacag tgaagctggg aagcagctct atgattagag ctttcaaagg cgtttcgatt    180
tacaaaaaca agaccagaag gaatgttctg tctcaaagga acaaacagtt ccgtcctatg    240
gcctacttag gaaggaagga cttgagcagc cctgatccga cctccttctg cgataatg     298

<210> SEQ ID NO 353
<211> LENGTH: 298
<212> TYPE: DNA
<213> ORGANISM: Brassica napus

<400> SEQUENCE: 353
atggagatga gactttggt ttcgtgttct gctgccggaa atggagcttc tgatcggttt      60
agactctcca atgtttcacc atggatcaca tcagctcgtg gtgcaagtgg cagtgactcc    120
ccagccacag tgaagctggg aagcagctct atgatcagag ccttcaaagg agtttcgatt    180
tacaaaaaca agaccagaag aaatgttttg tctcaaagga acaaacagtt tcgtcctatg    240
gcctacttag gaaggaagga cttgagcagc cctgatccga cctccttctg cgataatg     298
```

COMPOSITIONS AND METHODS FOR IMPROVING PLASTID TRANSFORMATION EFFICIENCY IN HIGHER PLANTS

This application is a continuation-in-part of PCT/US2018/013034 filed Jan. 9, 2018 which claims priority under 35 U.S.C. § 119(e) to U.S. Provisional Patent Application No. 62/444,307, filed on Jan. 9, 2017. The entire disclosure of each of the aforesaid applications is incorporated by reference in the present application.

INCORPORATION-BY-REFERENCE OF MATERIAL SUBMITTED IN ELECTRONIC FORM

Applicant hereby incorporates by reference the Sequence Listing material filed in electronic form herewith. This file is labeled "6424US01_20190925_03_SequenceListing_ST25.txt", created Sep. 25, 2019 and is 138,941 bytes in size.

FIELD OF THE INVENTION

The present invention relates the fields of plant biology and plastid transformation. More specifically, the invention pertains to molecular strategies for improving plastid transformation efficiency in recalcitrant plant species.

BACKGROUND OF THE INVENTION

Several publications and patent documents are cited throughout the specification in order to describe the state of the art to which this invention pertains. Each of these citations is incorporated by reference herein as though set forth in full.

Plastids are semi-autonomous plant organelles with thousands of copies of the ~155-kb genome localized in 10 to 100 plastids per cell. The plastid genome of higher plants encodes about one hundred genes, the products of which assemble with 3,000 nucleus-encoded proteins to form the plastid transcription and translation machinery and carry out complex metabolic functions, including photosynthesis, and fatty acid and amino acid biosynthesis. Transformation of the plastid genome in flowering plants was first accomplished in tobacco (*Nicotiana tabacum*), the current model species of plastid engineering (Svab et al., 1990; Svab and Maliga, 1993).

Plastid transformation is routine only in tobacco, but reproducible protocols for plastid transformation have also been described in tomato (Ruf et al., 2001), potato (Valkov et al., 2011), lettuce (Kanamoto et al., 2006; Ruhlman et al., 2010) and soybean (Dufourmantel et al., 2004). Still, the technology is available in only a relatively small number of crops. *Arabidopsis thaliana*, the most widely used model plant is one of the species that is recalcitrant to plastid transformation. In *Arabidopsis*, only 2 transplastomic events were identified in 201 samples (Sikdar et al., 1998), a sample size that would have yielded ~200 events in tobacco using the technology available in 1988 (Svab and Maliga, 1993). Until now the reasons for the low efficiency in *Arabidopsis* were not understood.

SUMMARY OF THE INVENTION

In accordance with the present invention, a method for increasing sensitivity to spectinomycin in plastids of higher plants for increasing plastid transformation efficiency is provided. An exemplary method comprises providing a plant having a nonfunctional ACC2 nuclear gene, introducing one or more plastid transformation vectors into plastids in cells from said plant, said one or more vectors comprising an aadA spectinomycin resistance marker sequence and a nucleic acid sequence encoding a protein of interest. The plant cells are then contacted with spectinomycin and spectinomycin resistant plant cells which accumulate the protein of interest in said plastids selected. The method also includes culturing said plant cells under conditions suitable to regenerate a transplastomic plant therefrom. In preferred embodiments, the plant is selected from the group consisting of *Arabidopsis* ssp., *Brassica* ssp., *Camelina* ssp., and *Crambe* spp. In a further aspect, the method entails excising the resistance marker from said plant. This can be achieved using the protocols provided in U.S. Pat. Nos. 8,841,511; 7,667,093 and 7,217,860.

Plants to be transformed can be naturally occurring ACC2 mutants which are defective in acc2 activity. Alternatively, desirable plant species can be identified and the ACC2 gene is inactivated in said plant using the CRISPR/Cas system and the appropriate guide strands.

In another embodiment, a method for seed-specific plastid expression is provided. An exemplary method comprises introducing a nuclear expression vector encoding a modified PPR10 binding protein driven by a seed-specific promoter and a plastid expression vector encoding a gene of interest linked to an upstream PPR10 binding site, wherein nuclear-expressed PPR10 is imported into plastids and binds said PPR10 binding site to drive expression of the gene of interest in seed plastids. In certain embodiments, the vector comprises a seed specific promoter selected from a napin or a phaseolin gene promoter. In other embodiments, the modified PPR10 binding protein is PPR10$^{GG}$ and encoded by SEQ ID NO: 265. The PPR10 binding site may also be encoded by SEQ ID NO: 261. The vector may also comprise the aadA spectinomycin resistance gene. Additionally, in another aspect, the plastid expressed gene of interest is linked to an upstream sequence encoding a maize atpH gene and/or tRNA sequence in said plastid vector.

In another aspect of the invention, a method for increasing sensitivity to plastid translation inhibitors in plastids of higher plants for increasing plastid transformation efficiency is provided. An exemplary method comprises providing a plant comprising a nonfunctional ACC2 nuclear gene, introducing one or more plastid transformation vectors into the plastids in cells from said plant, said one or more vectors comprising a nucleic acid sequence conferring resistance to said plastid translation inhibitor, and a nucleic acid sequence encoding a protein of interest. The method further entails contacting said cells with said inhibitor and selecting plant cells which are resistant to said inhibitor and accumulate said protein of interest in said plastids; and culturing said plant cells under conditions suitable to regenerate a transplastomic plant therefrom. In certain embodiments, the plastid translation inhibitor is selected from kanamycin, chloramphenicol, tobramycin and gentamycin.

BRIEF DESCRIPTION OF THE DRAWINGS

(FIG. 1A) In most accessions the heteromeric ACCase (hetACC) localizes in the chloroplast and is encoded by nuclear genes CAC1-A (At5g16390; Biotin Carboxyl Carrier Protein 1 (BCCP-1)), CAC1-B (At5g15530; Biotin Carboxyl Carrier Protein 2 (BCCP-2)) (not depicted in figure), CAC2 (At5g35360;

Biotin Carboxylase (BC)), CAC3 (At2g38040, a subunit of Carboxyltransferase (α-CT) and the plastid encoded gene accD (AtCg00500; (β subunit of Carboxyltransferase (β-CT)). The homomeric ACC1 (At1g36160; homACCase) enzyme localizes in the cytoplasm and the ACC2 (At1g36180; homACCase) enzyme is imported into the chloroplast via the TIC/TOC membrane protein complex. If translation of the plastid accD mRNA is blocked by spectinomycin, the nuclear homomeric ACC2 gene supplies the cells with lipids so that cellular viability is not affected. (FIG. 1B) In ACC2 mutants, the absence of the homomeric ACCase makes the plants dependent on plastid translation to produce the heteromeric ACCase enzyme for fatty acid biosynthesis.

(FIG. 3A) Sterile Sav-0 plants grown in Petri dishes (diameter 10 cm) for six weeks. (FIG. 3B) Two days after bombardment (biolistic transformation) the leaves are incised and transferred to selective spectinomycin (100 mg/L) medium. (FIG. 3C) Sav-0 leaves on selective medium one month after bombardment. Note scanty callus formation and green cell cluster (arrow). (FIG. 3D) Culture shown in FIG. 3C, illuminated with UV light. Note green fluorescence indicating GFP accumulation in green cell cluster. (FIG. 3E) Sav-0 plant regenerated from a transplastomic clone #6. (FIG. 3F) Culture shown in FIG. 3E, illuminated with UV light. Inset-Sav-0 #3 seed progeny illuminated with UV light. Bar=1 mm.

FIGS. 6A-6C. Alignment of homomeric ACCases in the Brassicaceae family. (FIG. 6A) Alignment of 200 the N-terminal amino acids of *Arabidopsis thaliana* ACC1 (At1g36160, SEQ ID NO: 222) and ACC2 (At1g36180, SEQ ID NO: 301) genes. The consensus sequence is provided as SEQ ID NO: 302. (FIG. 6B) Alignment of 200 the N-terminal amino acids of *Arabidopsis thaliana* ACC1: At1g36160 (SEQ ID NO: 303); *Arabidopsis lyrata* ACC1: XM_002891166.1 (SEQ ID NO: 304); *Camelina sativa* ACC1-1: LOC104777496 (SEQ ID NO: 305); *Camelina sativa* ACC1-2: LOC104743830 (SEQ ID NO: 306); *Capsella rubella* ACC1: CARUB_v10011872 mg (SEQ ID NO: 307); *Brassica oleracea* ACC1: LOC106311006 (SEQ ID NO: 308); *Brassica napus* ACC1-1: LOC106413885 (SEQ ID NO: 309); *Brassica napus* ACC1-2: LOC106418889 (SEQ ID NO: 310); *Brassica rapa* ACC1: LOC103833578 (SEQ ID NO: 311). The consensus sequence is provided as SEQ ID NO: 312. (FIG. 6C) Alignment of 300 the N-terminal amino acids of *Arabidopsis thaliana* ACC2: At1g36180 (SEQ ID NO: 313); *Arabidopsis lyrata* ACC2: XM_002891167.1 (SEQ ID NO: 314); *Camelina sativa* ACC2-1: LOC104777495 (SEQ ID NO: 315); *Camelina sativa* ACC2-2: LOC104742086 (SEQ ID NO: 316); *Capsella rubella* ACC2: CARUB_v10008063 mg (SEQ ID NO: 317); *Brassica oleracea* ACC2: LOC106301042 (SEQ ID NO: 318); *Brassica napus* ACC2-1: Y10302 (SEQ ID NO: 319); *Brassica napus* ACC2-2: X77576 (SEQ ID NO: 320); *Brassica rapa* ACC2: LOC103871500 (SEQ ID NO: 321). The consensus sequence is provided as SEQ ID NO: 322.

FIG. 7. Design of sgRNAs for simultaneous mutagenesis of both *B. napus* ACC2 gene copies. Aligned are the first exons encoding the N-terminal plastid targeting regions (Seq_1: SEQ ID NO: 352 and Seq_2: SEQ ID NO: 353). The GG of NGG of the PAM sequence is encircled; the 20 nucleotide forward guide sequence (5'-3') is marked with a horizontal line. The first nucleotide of the guide sequence should be changed to a G or an A, dependent on the use of U6 or U3 promoter, respectively (Belhaj et al., 2013). 9 of the 15 potential gRNA sequences are suitable for targeting both ACC2 copies (2-8 and 14,15). The reverse guide sequences are included in Table 3.

FIG. 8. Mutations generated by CRISPR/Cas9 mutagenesis in the *Arabidopsis* Wassiliewskija (Ws) and RLD ecotypes. Top—Columbia reference sequence (Col-0: nt 1 to 104 (top) or nt 1 to 100 (bottom) of SEQ ID NO: 6) and the parental Ws/RLD sequences (Ws/RLD: SEQ ID NO: 324 (top) or nt 1 to 100 (bottom) of SEQ ID NO: 324). Note mutations that alter the reading frame yielding non-functional protein, such as a one nucleotide insertion in Ws-6-2 (SEQ ID NO: 325 and RLD-6-2 (SEQ ID NO: 326) lines. Ws-10-35: SEQ ID NO: 327; Ws-11-5: SEQ ID NO: 328; Ws-11-28: SEQ ID NO: 329; Ws-6-23: SEQ ID NO: 330; Ws-6-11: SEQ ID NO: 331; Ws-6-9: SEQ ID NO: 332; Ws-11-96: SEQ ID NO: 333; Ws-6-19: SEQ ID NO: 334; RLD-10-25: SEQ ID NO: 335; RLD-6-10: SEQ ID NO: 336; RLD-10-2: SEQ ID NO: 337; RLD-6-13: SEQ ID NO: 338; RLD-6-15: SEQ ID NO: 339; RLD-10-10: SEQ ID NO: 340; RLD-6-6: SEQ ID NO: 341; RLD-10-29: SEQ ID NO: 342; RLD-11-14: SEQ ID NO: 343; and RLD-10-8: SEQ ID NO: 344. Bottom—oligonucleotide sequence used for construction of gRNA (sgRNA-ACC2-F2 and Seq_1 1: SEQ ID NO: 255; sgRNA-ACC2-R2: SEQ ID NO: 256; and Seq_2 1: SEQ ID NO: 323).

FIG. 11. A schematic diagram depicting system for seed-specific expression of plastid genes from acc2 defective plants.

(FIG. 12A) Plastid transgenes. P1 and T1 are the expression signals of the aadA marker gene. Preferred sequences are listed in text. P1 is the tobacco plastid Prrn sequence. The half circle is the maize sequence containing $BS^{ZmGG}$ sequence. gfp encodes green fluorescence protein. T1 is the rbcL gene terminator. Cloverleaf symbolizes tRNA gene. (FIG. 12B) The map of *Agrobacterium* binary vector pCAMBIA2300 with the PnpaA:Zm-PPR10GG:Tocs and selectable kanamycin resistance gene. P1 and T1 are Pnos/Tnos, the expression signals of kanamycin resistance (neo) gene. P2 is the PnpaA napin promoter; $PPR10^{GG}$ sequence is the mutant maize PPR10 protein coding sequence; T2 is Tocs octopine synthase transcription terminator. LB and RB are the T-DNA left and right border sequences.

FIG. 14A-14C. FIG. 14A Functional ACC2 copies make *B. napus* plants tolerant to spectinomycin, permitting growth beyond the cotyledon stage. FIG. 14B and FIG. 14C. Flowchart to obtain Cas9-free spectinomycin hypersensitive acc2 *Brassica napus*. (14B) Selection of CRISPR/Cas9 transgenic plants by kanamycin resistance. (14C) Hypersensitivity bioassay identifies T1 families with putative knockouts in all ACC2 copies, leading to the isolation of Cas9-free acc2 individuals. Non-uniform hypersensitivity to spectinomycin will prompt an additional cycle of screening in the next seed generation.

DETAILED DESCRIPTION OF THE INVENTION

Spectinomycin, a preferred agent used for selecting for transplastomic events, binds to the 16S ribosomal RNA, blocking translation on the prokaryotic type 70S plastid ribosomes (Wirmer and Westhof, 2006; Wilson, 2014) inhibiting greening and shoot regeneration in tissue culture cells (Svab et al., 1990). When the plastid genome is transformed with the aadA gene encoding aminoglycoside-3"-adenylyltransferase, the modified antibiotic no longer binds to the 16S rRNA and translation proceeds, enabling greening. Tobacco, when cultured on a spectinomycin medium, bleaches and proliferates at a slow rate due to inhibition of plastid translation. Transplastomic tobacco cells are identified in tissue culture by the ability to green and regenerate shoots. In contrast, *Arabidopsis* bleaches but continues to proliferate on a spectinomycin medium in the absence of chloroplast ribosomes (Zubko and Day, 1998). Two major studies by Parker et al. (Parker et al., 2014, 2016) revealed the existence of rare *Arabidopsis* accessions, in which plastids are extremely sensitive to spectinomycin. Seeds of most accessions in the study germinated on spectinomycin and developed into albino plants.

Figure 1A:
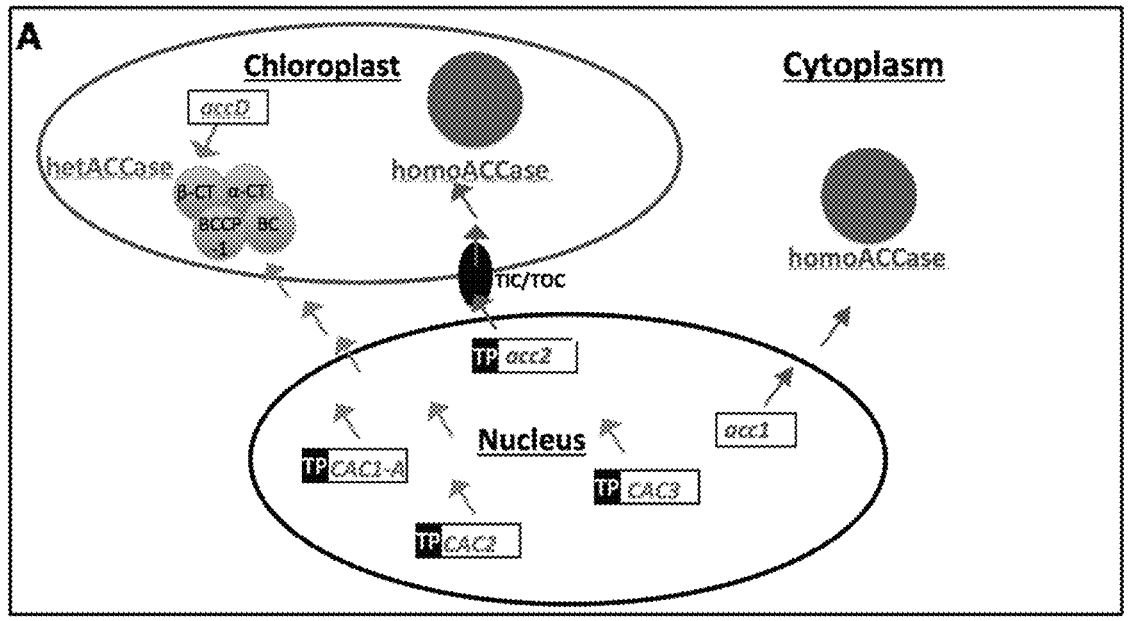
FIGS. 1A-1B. Defective ACC2 Gene Makes Chloroplasts More Sensitive to Spectinomycin.
Figure 1B:
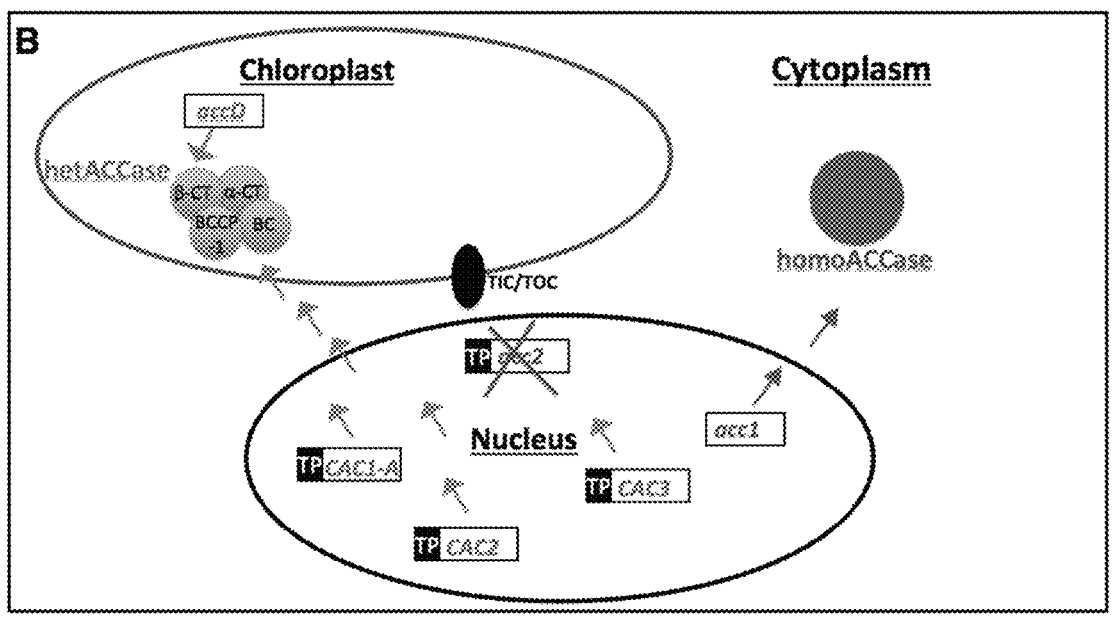

However, in certain accessions, spectinomycin blocked plant development: the seeds germinated, but did not develop beyond the cotyledonary stage. Genetic analysis revealed that spectinomycin sensitivity in these accessions is due to mutations in the ACC2 nuclear gene. The ACC2 gene produces the homomeric acetyl-CoA-carboxylase (ACCase) that is imported into plastids, and duplicates the function of heteromeric ACCase, one subunit of which is encoded in the plastid accD gene (FIG. 1A). When plastid translation is blocked by spectinomycin and no heteromeric ACCase is made, the homomeric enzyme enables a limited amount of fatty acid biosynthesis and development of albino plants. In the absence of a functional ACC2 gene, fatty acid biosynthesis is dependent on the availability of heteromeric ACCase enzyme, the (3-Carboxylase subunit of which is translated on plastid ribosomes (FIG. 1B).

We hypothesized that the inefficiency of plastid transformation observed in our early efforts with *Arabidopsis* was due to the lack of the sensitivity to spectinomycin, and that transformation of mutants defective in ACC2 function should increase efficient recovery of transplastomic clones. We report here that the efficiency of plastid transformation in the acct background in *Arabidopsis* is comparable to that of tobacco, confirming our hypothesis. Antibiotics kanamycin, chloramphenicol, tobramycin and gentamycin are similar to spectinomycin in that they also act through inhibition of plastid translation. Kanamycin resistance is conferred by the neo (nptll) gene, encoding neomycin phosphotransferase or the aphA-6 gene encoding an aminoglycoside phosphotransferase. Chloramphenicol resistance is conferred by the cat gene encoding chloramphenicol acetyltransferase. Tobramycin/gentamycin resistance is conferred by the bifunctional aac(6')-Ie/aph(2")-Ia gene, abbreviated as aac6-aph2 gene, encoding the bifunctional aminoglycoside phosphotransferase(6')-Ie/APH(2")-Ia enzyme.

Thus, improved recovery of transplastomic events is expected in the acc2 defective background using these inhibitors of organellar translation as selective markers.

In view of this finding, we have expanded our efforts to create additional strains of acc2 defective plants in the Brassicaceae family. Herein below protocols and expression vectors are provided for both nuclear and plastid transformation in such plants, which include, without limitation, *A. lyrata, C. sativa, C. ruella, B. oleracea, B. napus, B. rapa*. The inventor also provides suitable guide strands for introducing mutations in ACCases via a CRISPR/CAS.

The definitions below are provided to facilitate an understanding of the invention.

Heteroplastomic refers to the presence of a mixed population of different plastid genomes within a single plastid or in a population of plastids contained in plant cells or tissues.

Homoplastomic refers to a pure population of plastid genomes, either within a plastid or within a population contained in plant cells and tissues. Homoplastomic plastids, cells or tissues are genetically stable because they contain only one type of plastid genome. Hence, they remain homoplastomic even after the selection pressure has been removed, and selfed progeny are also homoplastomic. For purposes of the present invention, heteroplastomic populations of genomes that are functionally homoplastomic (i.e., contain only minor populations of wild-type DNA or transformed genomes with sequence variations) may be referred to herein as "functionally homoplastomic" or "substantially homoplastomic." These types of cells or tissues can be readily purified to a homoplastomic state by continued selection.

Plastome refers to the genome of a plastid.

Transplastome refers to a transformed plastid genome.

Transformation of plastids refers to the stable integration of transforming DNA into the plastid genome that is transmitted to the seed progeny of plants containing the transformed plastids. Transient expression of heterologous DNA into the plastid or nuclear compartments can also be employed.

Selectable marker gene refers to a gene that upon expression confers a phenotype by which successfully transformed plastids or cells or tissues carrying the transformed plastid can be identified.

Transforming DNA refers to homologous DNA, or heterologous DNA flanked by homologous DNA, which when introduced into plastids becomes part of the plastid genome by homologous recombination.

"Operably linked" refers to two different regions or two separate genes spliced together in a construct such that both regions will function to promote gene expression and/or protein translation.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

The term "functional" as used herein implies that the nucleic or amino acid sequence is functional for the recited assay or purpose.

Mao et al. provide detailed guidance for use of the CRISPR/Cas system in higher plants in Molecular Plant, 6: 2008-2011 (2013). The article entitled "Application of the CRISPR-Cas System for Efficient Genome Engineering in Plants" and its supplemental material is incorporated herein by reference as though set forth in full.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion, biolistic bombardment and the like.

"Floral dip transformation" refers to *Agrobacterium* mediated DNA transfer, in which the flower is brought in contact with the *Agrobacterium* solution. Floral dip transformation has been described in *Arabidopsis* (Clough and Bent, 1998) and *Brassica* spp. (Verma et al., 2008; Tan et al., 2011).

"T-DNA" refers to the transferred-region of the Ti (tumor-inducing) plasmid of *Agrobacterium tumefaciens*. Ti plasmids are natural gene transfer systems for the introduction of heterologous nucleic acids into the nucleus of higher plants. Binary *Agrobacterium* vectors such pBIN20 and pPZP222 (GenBank Accession Number U10463.1) are known in the art.

A "plastid transit peptide" is a sequence which, when linked to the N-terminus of a protein, directs transport of the protein from the cytoplasm to the plastid.

A "clone" or "clonal cell population" is a population of cells derived from a single cell or common ancestor by mitosis.

A "cell line" is a clone of a primary cell or cell population that is capable of stable growth in vitro for many generations.

A "defective" and "nonfunctional" gene, such as acct, refers to a gene which does not encode a functional protein. For example, a one nucleotide insertion on deletion may alter the reading frame to creates an in-frame stop codon.

Methods for Creating Transplastomic Plants Using the Compositions of the Invention Virtually all dicots have accD, an heteromeric ACCase subunit gene encoded in their plastid genome, but also have homomeric, plastid targeted nuclear ACC2 gene copies, which is the likely cause for the difficulty of extending the plastid transformation technology to all crops. Deletion of the nuclear ACC2 genes will enable plastid transformation in these dicot species and genetic lines.

The recognition that the plastid targeted ACCase in *Arabidopsis* is an impediment to plastid transformation provides a rational template to implement plastid transformation in recalcitrant crops. The accD gene is present on the plastid genome of most crops. The *Arabidopsis thaliana* ACC2 enzyme has an N-terminal extension relative to ACC1 that serves as an N-terminal plastid targeting sequence (Babijchuk et al., 2011). The ACC1 and ACC2 genes are present in all Brassicaceae species, including *Arabidopsis lyrata, Camelina* sativa, *Camelina rubella, Brassica oleracea, Brassica napus* and *Brassica rapa*. The homomeric ACC2 enzyme in these species has an N-terminal extension relative to ACC1. A targeted mutation in the N-terminal extension should selectively inactivate the ACC2 variant, expected to create a spectinomycin sensitive mutant similar to the Col-0 acct-1 mutant derivative (Parker et al., 2014). Plastid transformation has been achieved in cabbage (*Brassica oleracea* L. var. *capitata* L.), thus knockout of ACC2 is apparently not necessary to obtain transplastomic events in this crop, at least in the two cultivars tested (Liu et al., 2007; Liu et al., 2008). Plastid transformation in cauliflower (*Brassica oleracea* var. *botrytis*) has been obtained, but at a very low frequency (Nugent et al., 2006). Plastid transformation in oilseed rape (*Brassica napus*) has also been obtained, but no homoplastomic plants could be obtained (Hou et al., 2003; Cheng et al., 2010), or the transformation efficiency was low (Schneider et al., 2015). Plastid transformation in *Lesquerella fendleri*, another oilseed crop in the Brassicaceae, was feasible but inefficient (Skarjinskaia et al., 2003). Mutagenesis of ACC2 in the latter cases should significantly boost plastid transformation efficiency. Accordingly, a CRISPR/Cas approach for knocking out the ACC gene is provided in Example II.

Alternatively, desirable plant species could be screened for mutations in nuclear ACC genes and those strains harboring such mutations utilized in the plastid transformation methods disclosed herein. Such strains should inherently be more sensitive to spectinomycin.

The materials and methods set forth below were utilized in the performance of Example I.

Tissue Culture Media

The tissue culture media were adopted from Sikdar et al. (1998), originally described by Marton and Browse (1991). The culture media are based on Murashige and Skoog (MS) salts (Murashige and Skoog, 1962). ARM consists of MS salts, 3% (w/v) Suc, 0.8% (w/v) agar (A7921; Sigma), 200 mg of myoinositol, 0.1 mg of biotin (1 mL of 0.1 mg mL-1 stock), and 1 mL of vitamin solution (10 mg of vitamin B1, 1 mg of vitamin B6, 1 mg of nicotinic acid, and 1 mg of Gly per mL) per liter, pH 5.8. ARMS medium consists of ARM supplemented with 5% (w/v) Suc. ARMI medium consists of ARM containing 3 mg of IAA, 0.6 mg of benzyladenine, 0.15 mg of 2,4-D, and 0.3 mg of isopentenyladenine per liter. ARMIIr medium consists of ARM supplemented with 0.2 mg/L naphthaleneacetic acid and 0.4 mg of isopentenyladenine per liter. The stocks of filter-sterilized plant hormones and antibiotics (100 mg/L spectinomycin HCl) were added to media cooled to 45° C. after autoclaving.

Shoot regeneration in the transplastomic Sav-0 clones was obtained on an ARM containing 2,4-D (0.5 mg/L), kinetin (0.05 mg/L), and spectinomycin (100 mg/L; 3 d) followed by incubation on an ARM containing IAA (0.15 mg/L), phenyladenine (1.6 mg/L), and spectinomycin (100 mg/L; Motte et al., 2013). Seed was obtained by growing shoots on MS salt medium containing 3% (w/v) Suc and 0.8% (w/v) agar (A7921; Sigma), pH 5.8.

Plant Materials and Growth Conditions

The *Arabidopsis* (*Arabidopsis thaliana*) Sav-0 (CS28725) and Col-0 homozygous acc2-1 knockout line (SALK 148966C) seeds were obtained from the *Arabidopsis* Biological Resource Center. The Col-0 seeds were obtained from Juan Dong (Rutgers University). The RLD and Ler seeds were purchased form Lehle Seeds.

For surface sterilization, seeds (25 mg) were treated with 1.7% (w/v) sodium hypochlorite (5× diluted 8.5% (w/v) commercial bleach) in a 1.5-mL Eppendorf tube for 15 min with occasional mixing (vortex). The bleach was removed by pipetting and washed three times with sterile distilled water. Seeds were germinated on 50 mL of ARMS medium in deep petri dishes (20 mm high and 10 cm in diameter). The plates were illuminated for 8 h using cool-white fluorescent tubes (2,000 1x). The seeds germinated after 10 to 15 d of incubation at 24° C. To grow plants with larger leaves, seedlings were transferred individually to ARMS plates (four plants per deep petri dish). The plates were illuminated for 8 h with cool-white fluorescent bulbs (2,000 1x) and incubated at 21° C. during the day and 18° C. during the night. One- to 2-cm-long, dark green leaves were harvested for bombardment after incubation for an additional 5 to 6 weeks.

Plastid Transformation Vector

Figure 2:
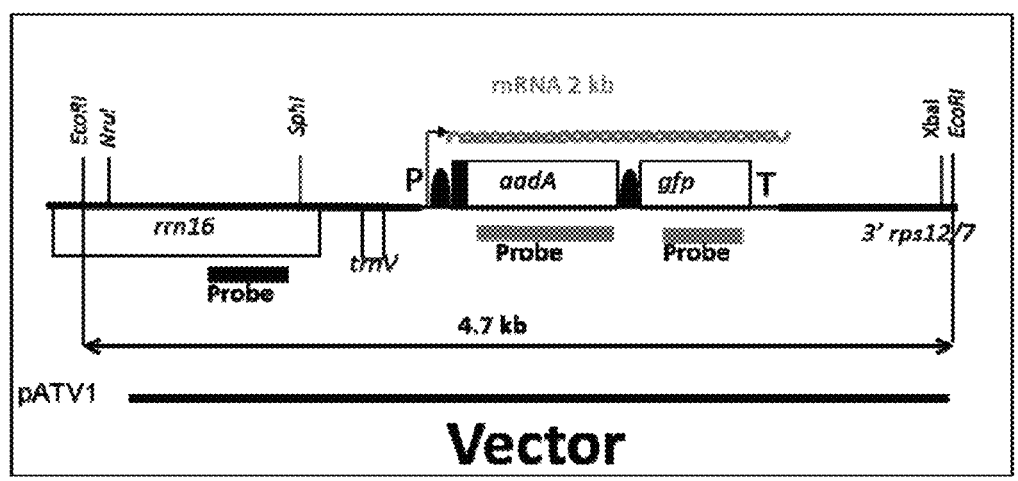
FIG. 2. Map of the Plastid Genome with the Integrated aadA-gfp Dicistronic Operon. The NruI-XbaI region is contained in the plastid transformation vector pATV1. P and T mark the positions of the PrrnL atpB promoter and the TpsbA terminator in the dicistronic vector. The black box at the aadA N terminus marks the atpB downstream box sequence (Kuroda and Maliga, 2001). The ribosome entry site is marked by black semi-ovals. The positions of the rrn16 and trnV plastid genes and relevant restriction enzyme sites are marked. Thick black and red lines indicate probes used for DNA and RNA gel-blot analyses, respectively.

The plastid transformation vector pATV1 targets insertion in the inverted repeat region of the plastid genome upstream of the trnV gene (FIG. 2). The targeting region is a 4.5 kb NruI/XbaI fragment derived from the *Arabidopsis thaliana* ptDNA (GenBank Accession No. NC_000932). The fragment was cloned in the KpnI-SacI site of a pBSKS+ BlueScript vector, ligating the vector KpnI site to the plastid NruI site and vector SacI site to the plastid XbaI site. The vector carries a dicistronic operon, in which the first open reading frame (ORF) encodes the aadA spectinomycin resistance gene and the second ORF encodes a green fluorescence protein (GFP). The operon is expressed from the PrrnLatpB promoter, obtained by fusing the plastid rRNA operon promoter (Prrn) with the atpB plastid gene leader (LatpB), originally described in the pHK30 plasmid (Kuroda and Maliga, 2001). The dicistronic aadA-gfp marker gene was excised as an EcoRI-HindIII fragment and cloned in the HindI site of the targeting region. In the dicistronic construct, 14 N-terminal amino acids of the ATP synthase beta subunit are translationally fused with the AAD N-terminus, as in plasmid pHK30 (Kuroda and Maliga, 2001). The intergenic region encodes the cry9Aa2 gene leader (Chakrabarti et al., 2006), followed by the gfp, coding region and the 3'-UTR of the plastid psbA gene (TpsbA) for the stabilization of the mRNA. The DNA sequence of the EcoRI-HindIII fragment encoding the aadA-gfp dicistronic operon in plasmid pMRR13 is shown below.

(SEQ ID NO: 1)
gagctcGCTCCCCCGCCGTCGTTCAATGAGAATGGATAAGAGGCTCGTGG

GATTGACGTGAGGGGGCAGGGATGGCTATATTTCTGGGAGAATTAACCGA

TCGACGTGCaAGCGGACATTTATTTTaAATTCGATAATTTTTGCAAAAAC

ATTTCGACATATTTATTTATTTTATTATTATGAGAATCAATCCTACTACT

TCTGGTTCTGGGGTTTCCACGgctactagcGAAGCGGTGATCGCCGAAGT

ATCGACTCAACTATCAGAGGTAGTTGGCGTCATCGAGCGCCATCTCGAAC

CGACGTTGCTGGCCGTACATTTGTACGGCTCCGCAGTGGATGGCGGCCTG

AAGCCACACAGTGATATTGATTTGCTGGTTACGGTGACCGTAAGGCTTGA

TGAAACAACGCGGCGAGCTTTGATCAACGACCTTTTGGAAACTTCGGCTT

CCCCTGGAGAGAGCGAGATTCTCCGCGCTGTAGAAGTCACCATTGTTGTG

CACGACGACATCATTCCGTGGCGTTATCCAGCTAAGCGCGAACTGCAATT

TGGAGAATGGCAGCGCAATGACATTCTTGCAGGTATCTTCGAGCCAGCCA

CGATCGACATTGATCTGGCTATCTTGCTGACAAAAGCAAGAGAACATAGC

GTTGCCTTGGTAGGTCCAGCGGCGGAGGAACTCTTTGATCCGGTTCCTGA

ACAGGATCTATTTGAGGCGCTAAATGAAACCTTAACGCTATGGAACTCGC

CGCCCGACTGGGCTGGCGATGAGCGAAATGTAGTGCTTACGTTGTCCCGC

ATTTGGTACAGCGCAGTAACCGGCAAAATCGCGCCGAAGGATGTCGCTGC

CGACTGGGCAATGGAGCGCCTGCCGGCCCAGTATCAGCCCGTCATACTTG

AAGCTAGACAGGCTTATCTTGGACAAGAAGAAGATCGCTTGGCCTCGCGC

GCAGATCAGTTGGAAGAATTTGTCCACTACGTGAAAGGCGAGATCACCAA

GGTAGTgGGCAAAgaaCAAAAACTCATTTCTGAAGAAGACTTGTAACTGC

AGATAACCCAAATAATGTTTTAAAATTTTAAAAATAATGTAGGAGGAAAA

ATTATGGCTAGCAGTAAAGGAGAAGAACTTTTCACTGGAGTTGTCCCAAT

TCTTGTTGAATTAGATGGTGATGTTAATGGGCACAAATTTTCTGTCAGTG

GAGAGGGTGAAGGTGATGCAACATACGGAAAACTTACCCTTAAATTTATT

TGCACTACTGGAAAACTACCTGTTCCtTGGCCAACACTTGTCACTACTTT

-continued
CTCTTATGGTGTTCAATGCTTTTCAAGATACCCAGATCATATGAAGCGGC

ACGACTTCTTCAAGAGCGCCATGCCTGAGGGATACGTGCAGGAGAGGACC

ATCTCTTTCAAGGACGACGGGAACTACAAGACACGTGCTGAAGTCAAGTT

TGAGGGAGACACCCTCGTCAACAGGATCGAGCTTAAGGGAATCGATTTCA

AGGAGGACGGAAACATCCTCGGCCACAAGTTGGAATACAACTACAACTCC

CACAACGTATACATCACGGCAGACAAACAAAAGAATGGAATCAAAGCTAA

CTTCAAAATTAGACACAACATTGAAGATGGAAGCGTTCAACTAGCAGACC

ATTATCAACAAAATACTCCAATTGGCGATGGCCCTGTCCTTTTACCAGAC

AACCATTACCTGTCCACACAATCTGCCCTTTCGAAAGATCCCAACGAAAA

GAGAGACCACATGGTCCTTCTTGAGTTTGTAACAGCTGCTGGGATTACAC

ATGGCATGGATGAACTATACAAATAAGctctagCTAGAGCgatcctggcc tagtctataggaggttttgaaaagaaaggagcaataatcattttcttgtt ctatcaagagggtgctattgctcctttcttttttttatttatttac tagtattttacttacatagactttttgtttacattatagaaaaagaagg agaggttattttcttgcatttattcatgGGGGATCAAAGCTT Transformation and Selection of Transplastomic Lines Plastid transformation in *Arabidopsis* was carried out using our 1998 protocol, as shown in FIG. 3A-3F (Sikdar et al., 1998). The leaves (10 to 20 mm) were harvested from aseptically grown plants and covered the surface of agar-solidified ARMI medium in a 10 cm petri dish. We used ~100 leaves to cover the surface of the plate. The leaves were cultured for 4 days on ARMI medium, then bombarded with pATV1 vector DNA. Transforming DNA was coated on the surface of microscopic (0.6 μm) gold particles, then introduced into chloroplasts by the biolistic process (1,100 psi) using a helium-driven PDS1000/He biolistic gun equipped with the Hepta-adaptor (Lutz et al., 2011). The plates were placed on the shelf at the lowest position for bombardment.

Following bombardment, the leaves were incubated for an additional 2 d on ARMI medium. After this time period, the leaves were stamped with a stack of 10 razor blades to create parallel incisions 1 mm apart. The stamped leaves were cut into smaller (1 cm2) pieces, transferred onto the same medium (ARMI) containing 100 mg/L spectinomycin, incubated at 28° C., and illuminated for 16 h with fluorescent tubes (CXL F025/741). After 8 to 10 d, the leaf strips were transferred onto selective ARMIIr medium containing 100 mg/L spectinomycin for the selection of spectinomycin-resistant clones. The leaf strips were transferred to a fresh selective ARMIIr medium every 2 weeks until putative transplastomic clones were identified as resistant green calli.

Confocal Microscopy to Detect GFP in Plastids

Subcellular localization of GFP fluorescence was determined by a Leica TCS SP5II confocal microscope. To detect GFP and chlorophyll fluorescence, excitation wavelengths were at 488 nm and 568 nm, and the detection filters were set to 500-530 nm and 650-700 nm, respectively.

DNA and RNA Gel-Blot Analyses

Total leaf DNA was prepared by the cetyltrimethylammonium bromide protocol (Tungsuchat-Huang and Maliga, 2012). DNA gel-blot analyses was carried out as described (Svab and Maliga, 1993). Total cellular DNA was digested with the EcoRI restriction enzyme. The DNA probe was the ApaI-SphI ptDNA fragment encoding the plastid rrn16 gene (FIG. 2).

Total cellular RNA was isolated from leaves frozen in liquid nitrogen using TRIzol (Ambion/Life Technologies) following the manufacturer's protocol. RNA gel-blot analyses were carried out as described (Kuroda and Maliga, 2001). The probes were as follows: for aadA, a 0.8-kb NcoI-XbaI fragment isolated from plasmid pHC1 (Carrer et al., 1991); and for gfp, a fragment amplified from the gfp coding region using primers gfp-forward p1 (5'-TTTTCTGTCAGTGGAGAGGGTG-3') (SEQ ID NO: 2) and gfp-reverse p2 (5'-CCCAGCAGCTGTTACAAACT-3' (SEQ ID NO: 3) (FIG. 2).

Alignment of Homomeric ACCases

The alignment of homomeric ACCases in the Brassicaceae family was carried out with MultAlin software (Corpet, 1988).

Accession Numbers

The DNA sequence of the pATV1 *Arabidopsis* plastid transformation vector was deposited in GenBank under accession number MF461355.

The following examples are provided to illustrate certain embodiments of the invention. They are not intended to limit the invention in any way.

Example I

Dicistronic pATV1 Vector for Identification of Transplastomic Events

The plastid transformation vector pATV1 targets insertion upstream of the trnV gene in the inverted repeat region of the plastid genome (FIG. 2). Vector pATV1 carries a dicistronic operon, in which the first open reading frame (ORF) encodes the aadA spectinomycin resistance gene and the second ORF encodes a green fluorescence protein (GFP) (FIG. 2). Polycistronic mRNAs are not translated on the eukaryotic-type 80S ribosomes in the cytoplasm, thus accumulation of GFP in chloroplasts in spectinomycin-resistant clones indicates plastid transformation.

Plastid Transformation and Identification of Transplastomic Events

Figure 3A:
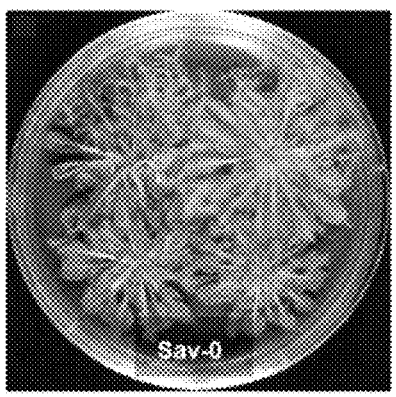
FIGS. 3A-3F. Identification of *Arabidopsis* Transplastomic Clones.
Figure 3C:
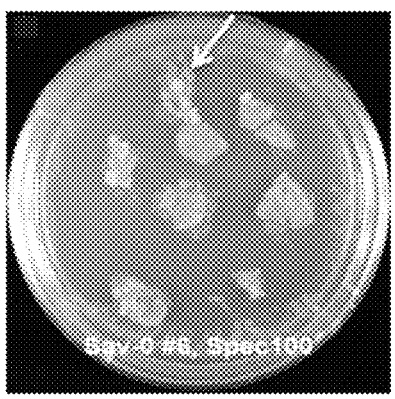
Figure 3E:
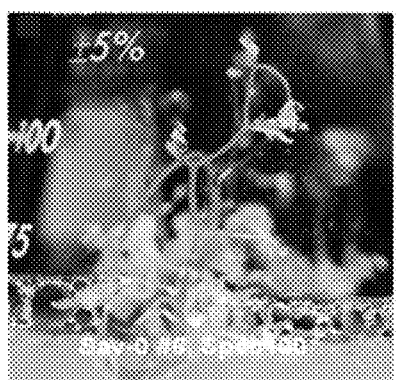
Figure 3B:
Figure 3D:
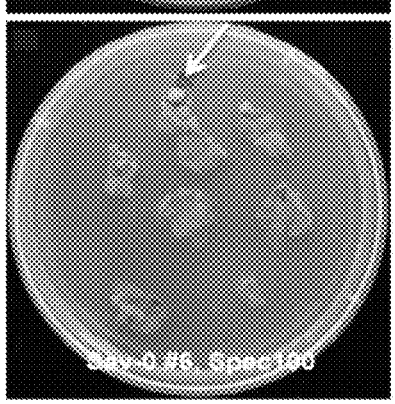

Plastid transformation was carried out in the Col-0 (Columbia) accession and the Columbia ACC2 T-DNA insertion line acct-1 (SALK 148966C) shown to be sensitive to spectinomycin in the Parker at el. study (Parker et al., 2014). We also evaluated plastid transformation efficiency in the Sav-0 (Slavice) accession that was the most sensitive to spectinomycin in the study (Parker et al., 2014). The Sav-0 ACC2 gene carries 15 missense mutations, but one variant alone (G135E) that alters a conserved residue immediately preceding the biotin carboxylase domain appears to be responsible for the hypersensitive phenotype (Parker et al., 2016). Plants were grown aseptically on ARMS medium (FIG. 3A); leaves for plastid transformation were harvested from sterile plants and placed on ARMI media. The leaf tissue was bombarded with gold particles coated with vector DNA. After two days, the leaves were stamped with a stack of razor blades to create a series of parallel incisions 1 mm apart. The mechanical wounds are essential to induce uniform callus formation in the leaf blades. The stamped leaves were transferred onto the same medium (ARMI) containing spectinomycin (100 mg/1; FIG. 3B) to facilitate preferential replication of plastids containing transformed ptDNA copies. The ARMI medium induces division of the leaf cells and formation of colorless, embryogenic callus. After 7-10 days of selection on ARMI medium, spectinomycin selection was continued on the ARMIIr medium, which induces greening. Since spectinomycin prevents greening of wild-type cells, only spectinomcyin-resistant cells formed green calli. Visible green cell clusters appeared within 21 to 40 days on the selective ARMIIr medium (FIG. 3C). Illumination of plates with UV light revealed intense fluorescence of GFP in the green calli (FIG. 3D).

In the wild-type Col-0 sample (four bombarded plates), no transplastomic event was found. We obtained eight events on five bombarded plates using leaf tissue in the acct-1 mutant background and four events in four bombarded plates in the Sav-0 accession (Table 1). This transformation efficiency is comparable to the transformation efficiency obtained with current protocols in tobacco: four to five transplastomic events per bombardment (Maliga and Tungsuchat-Huang, 2014).

Figure 4:
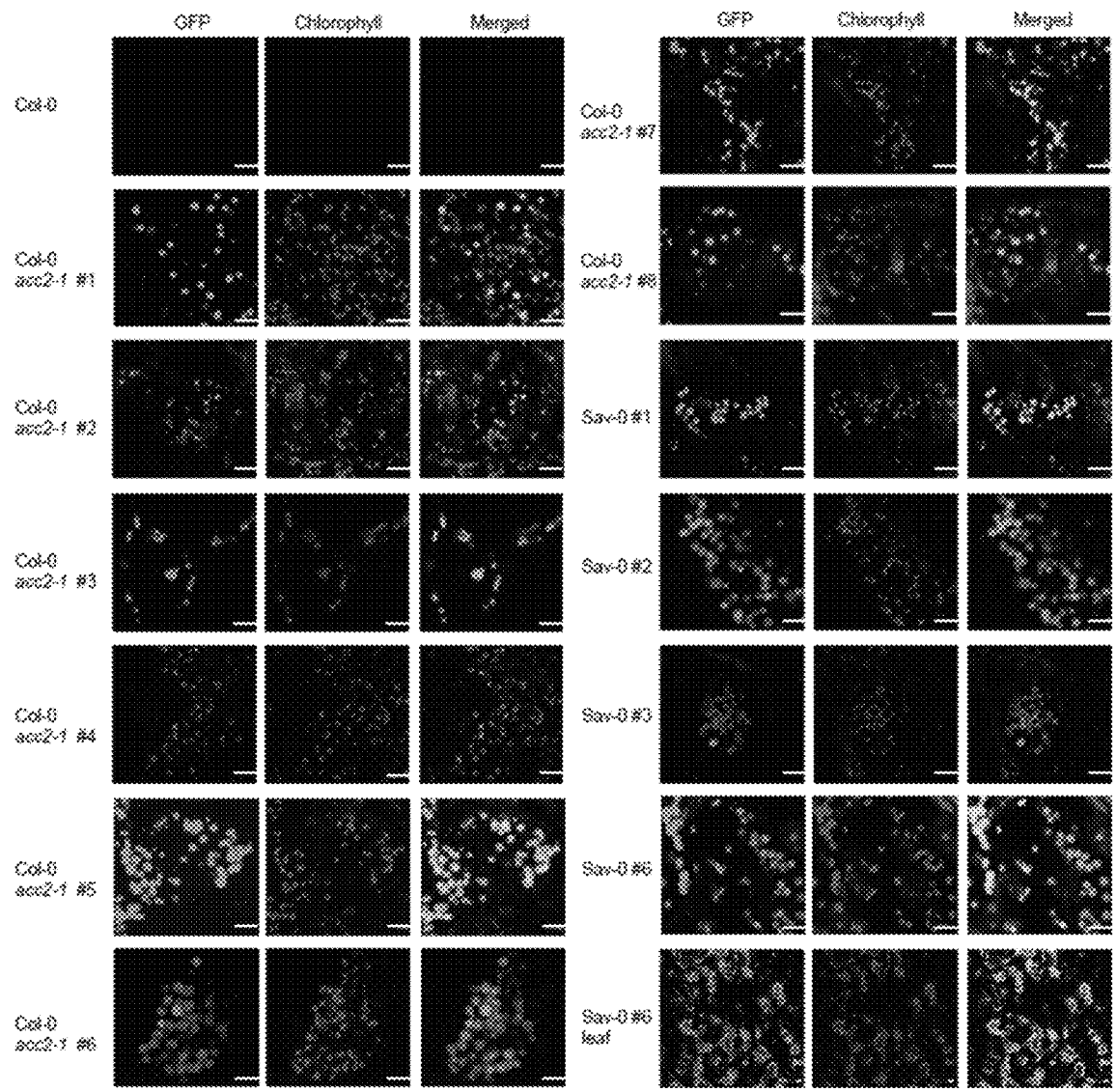
FIG. 4. Green Fluorescent Protein (GFP) accumulates in chloroplasts. Shown are confocal images collected in the GFP, chlorophyll, and merged channels on a Leica TCS SP5II confocal microscope. Excitation wavelengths were at 488 and 568 nm, and detection was at 500 to 530 and 650 to 700 nm, respectively. Note the absence of GFP and chlorophyll in the wild-type Col-0 callus cells and mixed GFP-expressing transgenic and wild-type plastids in the Col-0 acc2-1 #1 and Sav-0 #6 lines. Note the absence of wild-type plastids in the leaves of Sav-0 #6 plants. Yellow color in the merged images indicates the colocalization of GFP and chlorophyll in plastids. Note that cells in the small green cell clusters are heteroplastomic. The only exception are cells in Sav-0 6 leaves, which are homoplastomic due to prolonged selection in tissue culture. Bars=10 μm FIGS. 5A-5B. Molecular Characterization of the Sav-0 Transplastomic Clones.

This is a significant advance, as high-frequency plastid transformation in *Arabidopsis* has been pursued since the publication of the original report (Sikdar et al., 1998) but has been largely unsuccessful. For example, bombardment of 26 plates of RLD and five plates of Landsberg *erecta* (Ler) leaf tissue did not yield a transplastomic event (Table 1). In contrast, nine bombardments of leaves with the acct null background yielded 12 transplastomic clones. Even though the technology improved significantly since 1998, no transplastomic clones were obtained until ACC2-defective leaf tissue was used for bombardments (Table 1), providing overwhelming support for the absence of ACC2 activity being critical for high-frequency plastid transformation in *Arabidopsis*.

cells. Chlorophyll was detected in only a localized region of plastids in line with thylakoid biogenesis initiating from a localized center (Schottkowski et al., 2012). Good examples are overlays of Col-0 acct-1#5 and Sav-0 #1 in FIG. 4.

The heteroplastomic state detected in the cells of the green clusters was not maintained, and eventually, wild-type plastids (ptDNA) disappeared in the callus cells after continued cultivation on selective media. The homoplastomic state is confirmed by the uniform accumulation of GFP in the leaves of a Sav-0 #6 plant shown in FIG. 4 and by DNA gel-blot analyses of calli shown in FIG. 5B.

Regeneration of Transplastomic Sav-0 Plants and Transmission of GFP to Seed Progeny After the bombardment of Col-0 and Sav-0 leaves, the selection of transplastomic events was carried out according to the published RLD protocol (Sikdar et al., 1998). However, when the transplastomic clones were transferred to the RLD shoot induction medium, the calli did not proliferate. Therefore, we transferred the transplastomic calli to media that were used successfully to regenerate plants from other accessions. We found that the two-step regeneration protocol described for shoot induction in the C24 background (Motte et al., 2013) triggered shoot regeneration in two surviving Sav-0 calli. Calli of Sav-0 transplastomic lines #3 and #6 were briefly (3 d) exposed to callus induction medium containing 0.5 mg/L 2,4-dichlorophenoxyactetic acid (2,4-D) and 0.05 mg/L kinetin and then transferred to a shoot regeneration medium containing 0.15 mg/L indole acetic

TABLE 1

Identification of transplastomic events in *Arabidopsis*

| Plasmid | Left/right arm (kb) | Marker gene | Acession | Tissue | Gun | No. Plates | No. TP events | Ref. |
|---------|---------------------|-------------|----------|--------|-----|------------|---------------|------|
| pGS31A  | 1.1/0.9 | Prrn:LrbcL:aadA:TpsbA | RLD | Leaf | Single Tu/1 μm | 201 | 2 | Sikdar et al. 1998 |
| pAAK176 | 1.7/0.8 | Prrn:LrbcL:aadA:TpsbA | RLD | Leaf | Hepta Au/0.6 μm | 10 | 0 | Reported here |
|         |         |             | Ler | Leaf | Hepta Au/0.6 μm | 4 | 0 | Reported here |
| pTT626  | 1.7/0.8 | Prrn:Lcry9:aadA-gfp:TpsbA | RLD | Leaf | Hepta Au/0.6 μm | 14 | 0 | Reported here |
| pATV1   | 1.7/0.8 | PrrnLatpB:aadA:Lcry9:gfp:TpsbA | RLD | Leaf | Hepta Au/1 μm | 2 | 0 | Reported here |
|         |         |             | Ler | Leaf | Hepta Au/1 μm | 1 | 0 | Reported here |
|         |         |             | Col-0 | Leaf | Hepta Au/0.6 μm | 4 | 0 | Reported here |
|         |         |             | Col-0 acc2-1 | Leaf | Hepta Au/0.6 μm | 5 | 8 | Reported here |
|         |         |             | Sav-0 | Leaf | Hepta Au/0.6 μm | 4 | 4 | Reported here |

Au, gold particles; Hepta, using the Biolistic gun Hepta adaptor instead of a single flying disk; Tu, tungsten particles.

Confocal Microscopy to Confirm Transplastomic Events

Figure 3F:
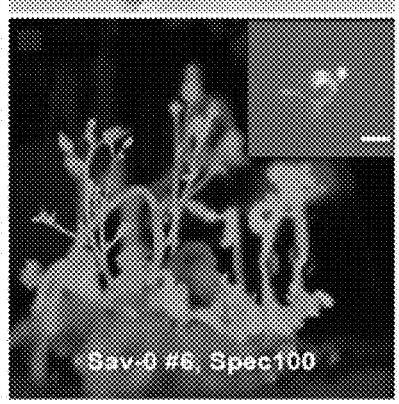
Figure 5A:
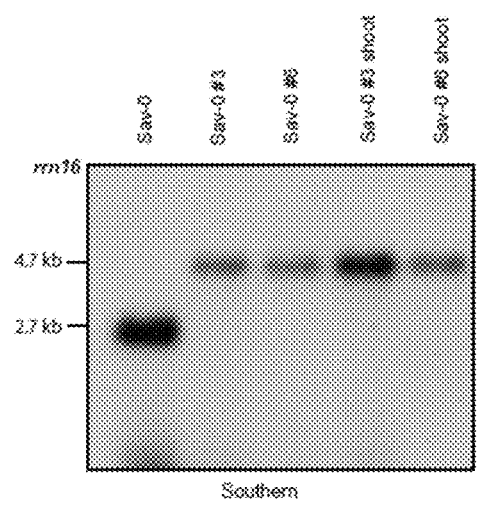
(FIG. 5A) DNA gel blot using the rrn16 probe (FIG. 2) indicates that the transplastomic Sav-0 calli and leaves are homoplastomic, carrying only the 4.7-kb EcoRI fragment and lacking the 2.7-kb wild type fragment.
Figure 5B:
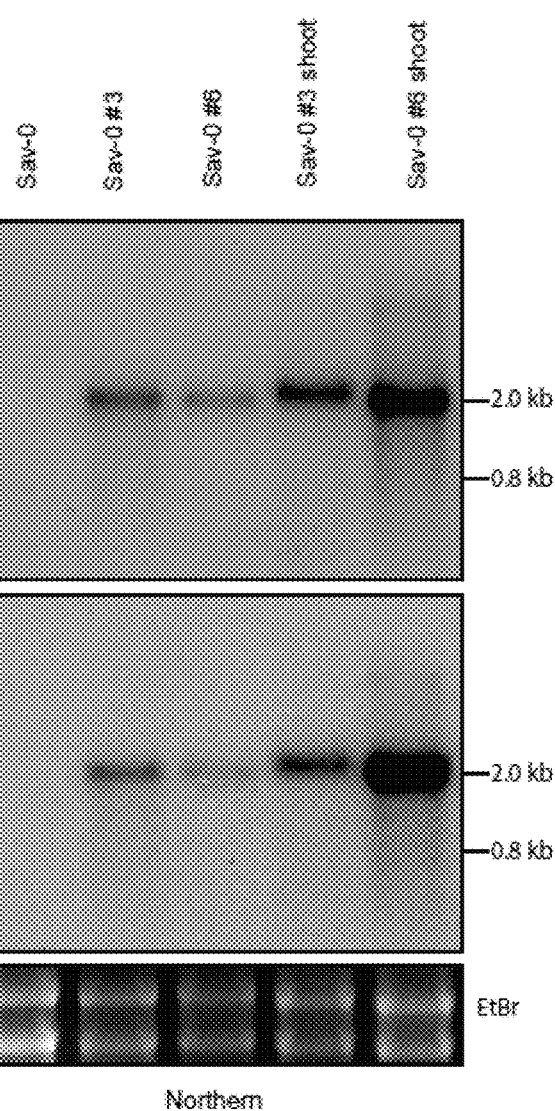
(FIG. 5B) The aadA and gfp probes recognize the same 2 kb dicistronic mRNA.

Because GFP is encoded in the second ORF, GFP accumulation is expected only if the mRNA is translated in plastids on the prokaryotic type 60S ribosomes known to translate transgenic polycistronic mRNAs. Examples are the plastid psbE operon (Carrillo et al., 1986; Willey and Gray, 1989), the psaA/B transcript (Meng et al., 1988) and petA, which is not cleaved off the upstream ycf10 gene (Willey and Gray, 1990). Translation of polycistronic mRNAs created by operon extension has also been demonstrated (Staub and Maliga, 1995). Thus, GFP accumulation was anticipated only if the gfp gene is expressed in chloroplasts. The putative transplastomic lines identified as green cell clusters have subsequently been confirmed as transplastomic events by detecting localization of GFP to plastids by confocal microscopy. Overlay of the GFP and chlorophyll channels indicates that the clones are heteroplastomic, carrying transformed and wild type plastids in the same cells. A good example for mixed plastids is shown in the overlay of GFP and chlorophyll channels in Col-0 acct-1#3 in FIG. 4. The chloroplasts were not well developed in most tissue culture acid (IAA) and 1.6 mg/L phenyladenine. Phenyladenine is a potent compound for shoot regeneration through the inhibition of cytokinin oxidase/dehydrogenase activity (Motte et al., 2013). Shoots from the calli developed in 45 to 60 days and flowered and formed siliques in sterile culture (FIG. 3E). The plants glowed intensely when illuminated with UV light, indicating high-level GFP accumulation (FIG. 3F-3G). Confocal microscopy suggests uniform transformation of plastid genomes in the leaves of Sav-0 #6 plants (FIG. 4) and was confirmed by molecular analyses (FIG. 5B).

The transplastomic shoots were transferred to larger 500-mL Erlenmeyer flasks containing ARM for seed set, where they continued to grow.

Molecular Analysis of Transplastomic *Arabidopsis* Clones

DNA and RNA gel blot analyses was carried out on the callus and shoots of the two Sav-0 transplastomic lines #3 and #6. Wild-type plastids present in the cells of the green clusters were gradually lost by the time DNA gel-blot analyses were carried out, confirming uniform transformation of the plastid genomes in both calli and shoots (FIG.

5A). RNA gel blot analyses indicated the presence of a 2-kb dicistronic transcript detected by both the aadA and gfp probes (FIG. 5B).

DISCUSSION

Development of successful plastid transformation protocols takes multiple years, explaining the relative paucity of crops in which plastid transformation is routine (Maliga and Bock, 2011; Maliga, 2012; Bock, 2015). The expectation is to obtain transplastomic plants, which carry and transmit to the seed progeny a uniformly transformed plastid genome population. The time required to obtain a flowering transplastomic plants from seed takes about 5 to 6 months, as outlined in Table 2. This time frame can be broken up into discrete steps, each of which represents a milestone in developing a complete system. We report here a significant break-through: high frequency transformation of the *Arabidopsis* plastid genome in spectinomycin sensitive accessions and a marker system that enables rapid identification of transplastomic events by selective expression of a GFP gene in plastids. This step is a major advance towards developing a complete system of plastid engineering in *Arabidopsis*.

TABLE 2

An overview of the protocol for the construction of a transplastomic *Arabidopsis* Sav-0 plants.

| | OBJECTIVE | CULTURE MEDIUM | TIME (No. of transfers) |
|---|---|---|---|
| Step 1 | Seed germination | ARM5 Medium | 14 days |
| Step 2 | Grow sterile plants | ARM5 medium | 42 days |
| Step 3 | Leaf callus, non selective | ARMI medium | 4 days |
| Step 4 | Leaf bombardment | ARMI medium | |
| Step 5 | Leaf callus, non selective | ARMI medium | 2 days |
| Step 6 | Leaf callus, selective | ARMI medium + Spectinomycin (100 mg/L) | 14 days |
| Step 7 | Leaf callus, greening | ARMIIr + Spectinomycin (100 mg/L) | 21 days (2x) |
| Step 8 | Shoot induction | ARM medium + 2,4-D (0.5 mg/L), kinetin (0.05 mg/L), Spectinomycin (100 mg/L) | 3 days |
| Step 9 | Shoot regeneration | ARM medium + IAA (0.15 mg/L), Phe-Ade (1.6 mg/L), Spectinomycin (100 mg/L) | 45-60 days |
| | Time to flowering plants: | | 145-160 days (~5 months) |

Development of a Plastid Transformation Protocol in *Arabidopsis*

The steps of a complete system of plastid engineering in *Arabidopsis* consist of: (a) obtaining or generating sterile acc2 defective plants to provide a leaf source for transformation; (b) delivering DNA to plastids; (c) recovering transplastomic events; (d) regenerating shoots from transplastomic callus and (e) obtaining seed from the shoots.

We report here approximately 100-fold enhanced plastid transformation efficiency per bombardment in the acc2 null background: eight events in five bombarded samples in the Col-0 acc2-1 line and four events in four bombarded samples in the Sav-0 background. The increase from one event per approximately 100 bombardments to one event per one bombardment is due in part to technological advances. However, the lack of success with the latest technology in a large number of bombarded samples (Table 1) provides overwhelming evidence that the key to success was the choice of *Arabidopsis* lines lacking ACC2 activity.

Identification of transplastomic events in the RLD ecotype took 5 to 12 weeks in 1998 (Sikdar et al., 1998). The use of spectinomycin-sensitive acc2-knockout lines and the pATV1 dicistronic operon vector shortened the time period for identification of transplatomic events to 3 to 5 weeks. The use of the acc2 knockout lines shortened scoring because the proliferation of non-transformed cells growth was efficiently inhibited by spectinomycin, enabling identification of the spectinomycin-resistant green cell clusters. Spectinomycin resistance may be due to the integration of aadA in the plastid genome, and fortuitous expression from an upstream promoter or spontaneous mutations in the rrn16 gene (Svab and Maliga, 1993). GFP, encoded in the second ORF, is expressed only in chloroplasts, enabling the rapid identification of transplastomic clones in a small number of heteroplastomic cells by confocal microscopy.

Once transplastomic clones are identified, the next major step is plant regeneration. There is diversity for shoot regeneration potential in *Arabidopsis* accessions. Col-0 is well known for its recalcitrance to shoot regeneration from cultured cells. Therefore, no attempt was made to regenerate shoots from the Col-0 transplastomic callus tissue. There is no information about the tissue culture properties of the Sav-0 accession. Our first attempts at Sav-0 shoot regeneration from the transplastomic clones proved successful, yielding flowering shoots in culture (FIG. 3E). However, the seeds, with one exception, failed to germinate. Shoot regeneration protocols have been worked out from root (Marton and Browse, 1991) and leaf explants (Lutz et al., 2015) of the RLD ecotype; and from protoplasts (Chupeau et al., 2013), leaf explants (Zhao et al., 2014) and inflorescence stem explants (Zhao et al., 2013) of the Wassilewskya (Ws) ecotype. Thus, a routine protocol for plastid transformation in *Arabidopsis* can be obtained by the refinement of leaf regeneration protocol in the Sav-0 ecotype, or by developing ACC2 knockout mutations in the RLD (Marton and Browse, 1991) or Wassilewskya (Ws) (Chupeau et al., 2013; Zhao et al., 2014) nuclear backgrounds. Alternatively, the Col-0 acct-1 can be transformed with the steroid-inducible BABY-BOOM gene to facilitate plant regeneration from transplastomic events (Lutz et al., 2015).

Seed from transplastomic tobacco is obtained by rooting shoots in tissue culture, then transferring the rooted cuttings to a greenhouse. *Arabidopsis* shoots obtained in tissue culture are notoriously difficult to root. Rather than making an effort to root the plants in culture and transfer them to the greenhouse, we obtained seed from plants in sterile culture, a two-three month process (Lutz et al., 2015).

Early Identification of Plastid Transformants

The dicistronic marker system is a developer's tool that enables early scoring, but severely burdens the developing plants due to the high level of AAD and GFP expression, ~7% and ~15% of total soluble cellular protein (TSP) in tobacco, respectively (unpublished). High-levels of AAD are not necessary to obtain transplastomic plants. We have found that a mutation in the promoter of the aadA gene reduced accumulation of AAD gene product below 1% without impact on the frequency of transplastomic events by spectinomycin selection (Sinagawa-Garcia et al., 2009). Therefore, the new *Arabidopsis* vectors expressing low levels of AAD described herein can be used to advantage as lowered expression levels of AAD do not compromise plant growth.

Figures 6A, 6B, 6C:
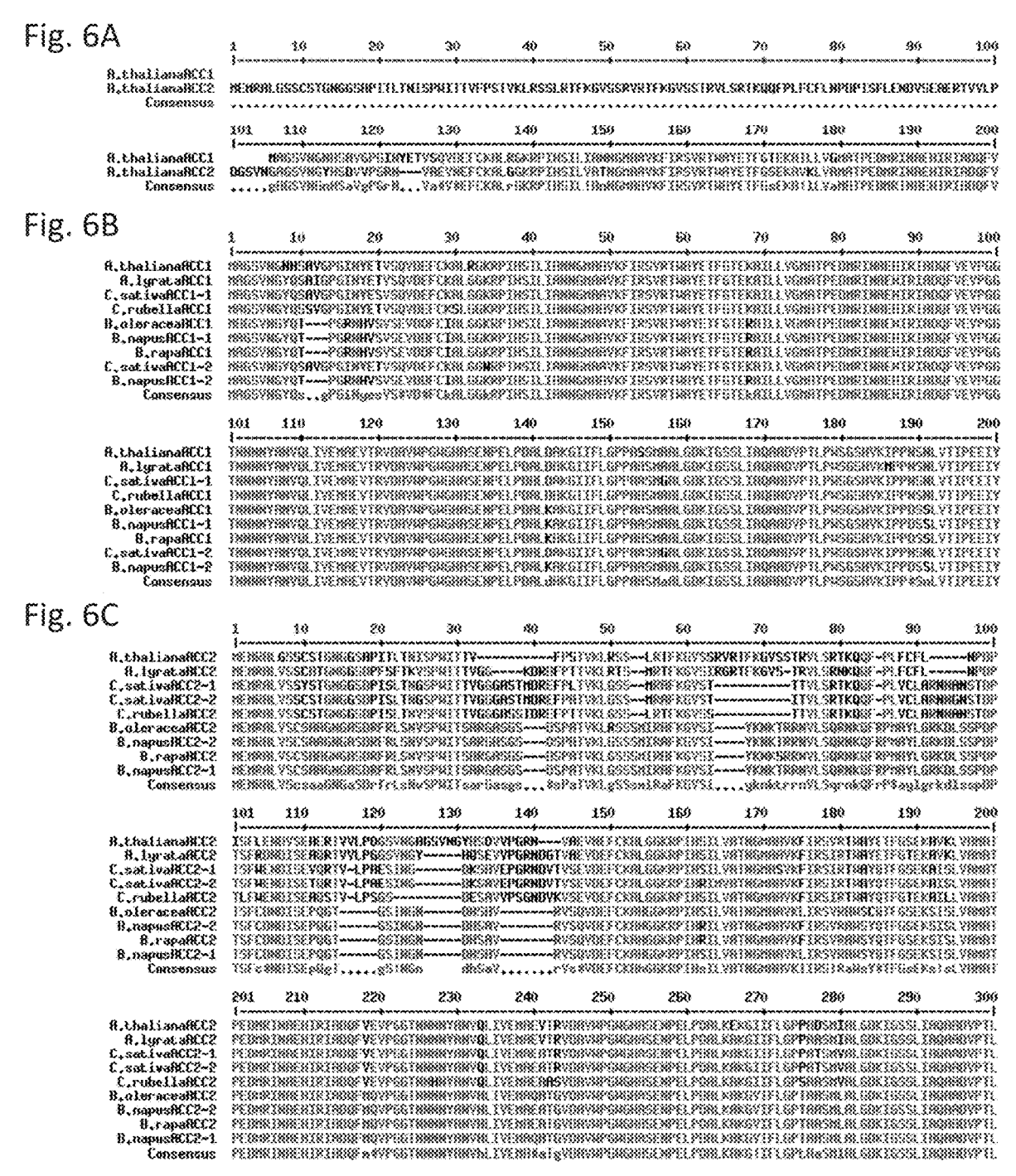

Plastid Transformation in *Arabidopsis* Provides Template for Recalcitrant Crops The recognition that the duplicated ACCase in *Arabidopsis* is an impediment to plastid transformation provides the guidance necessary for implementation of plastid transformation in all *Arabidopsis* accessions and in crops having a plastid-encoded accD gene and a plastid-targeted ACC2 enzyme. The *Arabidopsis thaliana* ACC2 enzyme has an N-terminal extension compared to ACC1 (FIG. 6A). The N-terminal extension is a plastid targeting sequence shown by subcellular localization of a GFP fusion protein (Babiychuk et al., 2011). The ACC1 and ACC2 genes are present in most Brassicaceae species, including *Arabidopsis lyrata, Camelina sativa, Camelina rubella, Brassica oleracea, Brassica napus* and *Brassica rapa*. The homomeric ACC2 enzyme in these species has an N-terminal extension compared to ACC1 (FIGS. 6B and 6C). Thus, a targeted mutation in the N-terminal extension can selectively inactivate the ACC2 variant to create a spectinomycin hypersensitive variant similar to the Col-0 acct-1 deletion derivative (Parker et al., 2014).

Crops recalcitrant to plastid transformation such as cotton (*Gossypium raimondii*), soybean (*Glycine max*) and alfalfa (*Medicago truncatula*) have a plastid accD gene and multiple homomeric nuclear ACC genes. Indeed, this method should prove effective in those plants having comparable ACC2 with an N-terminal extension. Moreover, further experimentation could be performed to determine how deletion of one or more of the homomeric ACCase genes enhances recovery of transplastomic events.

Mutations in genes other than ACC2 also made *Arabidopsis* sensitive to spectinomycin. The TIC20-IV gene, which is required for the import of proteins through the inner chloroplast membrane, appears to limit the import of ACC2 enzyme (Parker et al., 2014). Dicot plastid genomes have several essential genes, including accD, clpP, Ycf1 and Ycf2 (Scharff and Bock, 2014). Apparently, in photoheterotrophic cultures where sucrose in the medium eliminates the need for photosynthesis, only translation of the accD mRNA, hence fatty acid biosynthesis, is required to sustain plant life.

CONCLUSION

Boost of plastid transformation efficiency using ACC2 knockout lines in commercial species of Brassicaceae has obvious economic benefits. Genomic resources make *Arabidopsis* the favored model to study basic biological processes, and to explore new biotechnological applications (Weigel and Mott, 2009; Koornneef and Meinke, 2010; Stitt et al., 2010; Wallis and Browse, 2010). The exception is photosynthesis research and chloroplast biotechnology that utilizes tobacco (*Nicotiana tabacum*) because engineering of the plastid genome encoding key components of the photosynthetic machinery is routine in only this species (Hanson et al., 2016; Sharwood et al., 2016). If plastid transformation would be available in *Arabidopsis*, this research would be carried out in this model organism, in which a large mutant collection is available in virtually any nuclear gene contributing to photosynthesis. Recognizing the importance of plastid translation during selection of transplastomic events has identified a bottleneck of plastid transformation in *Arabidopsis*. High frequency plastid transformation in *Arabidopsis thaliana* will open up the unique resources of this model species to advance our understanding of plastid function and new biotechnological applications.

Example II

Deletion of ACC2 Genes in Brassicaceae Crops to Create Suitable Recipients for Plastid Transformation As discussed above in Example I, crops in the Brassicaceae family encode homologs of the *Arabidopsis* ACC2 gene, characterized by an N-terminal extension as compared to ACC1. Manual inspection of the N-terminal region of ACC2 genes led to the identification of >20 suitable guide RNAs (see Table 3). The potential gRNAs targeting both stands (5' to 3' and 3' to 5') are identified as NNNNNNNNNNNNNNNNNNNN NGG sequence (20N+NGG, N=A/G/C/T) (SEQ ID NO: 4), where the only limitation is the presence of a GG sequence (Mali et al., 2013). More relaxed rules for sgRNA design can be used in plants, such as $G(N)_{19-22}$ for the U6 promoter and $A(N)_{19-22}$ for the U3 promoter and the $1^{st}$ nucleotide does not have to match the genomic sequence (Belhaj et al., 2013).

*Brassica napus* L. (AACC, 2n=4x=38) is an amphidoploid species originating from spontaneous hybridization of *Brassica rapa* (AA, 2n=2x–20) and *Brassica oleracea* (CC, 2n=2x=18) (Song and Osborn, 1992; Howell et al., 2008). The *Brassica napus* genome encodes two ACC1 genes (Locus106413885; Locus106418889) and two ACC2 genes (GenBank accession numbers X77576, Y10302) (Schulte et al., 1997). Simultaneous mutation of two genomic sequences can be executed efficiently using CRISPR/Cas9, as described in the literature. A noteworthy example is simultaneous inactivation of 62 copies of a porcine endogenous retrovirus in pigs (Yang et al., 2015). Additionally, non-segregating seed progeny due to mutations in both genomic copies in the first generation of *Arabidopsis* and tomato plants (Feng et al., 2014) (Brooks et al., 2014). The alignment of 298 N-terminal nucleotides of the *Brassica napus* ACC2 genes reveals 7 mismatches. Still, 9 of the 15 potential forward sgRNAs are useful for simultaneously inducing mutations in both ACC2 gene copies (FIG. 7, Table 3).

To achieve targeted deletion in the ACC2 N-terminal region, the gRNAs are cloned into the CRISPR/Cas vector and introduced into different crops using a nuclear transformation system appropriate for the target species. For example, *Camelina sativa* plants will be transformed by the flower dip protocol (Liu et al., 2012). In the case of *Brassica*, introduction of the CRISPR/Cas vector system can be achieved using *Agrobacterium*-mediated transformation of hypocotyls (Cardoza and Stewart, 2003, 2006) or flower dip transformation (Tan et al., 2011; Verma et al., 2008) as described below.

*Agrobacterium*-Mediated Transformation of Hypocotyl Segments

*Brassica napus* L. cv. Westar is transformed with an *Agrobacterium* binary vector carrying kanamycin resistance as a plant marker. Seeds are surface-sterilized with 10% sodium hypochlorite with 0.1% Tween for 5 minutes, followed by a 1-min rinse with 95% ethanol and washing the seed 5× with sterile distilled water. The seeds are germinated in sterile culture on MS basal medium (Murashige and Skoog, 1962) containing 20 g/l sucrose and solidified with 2 g/l Gelrite. Hypocotyls for transformation are excised from 8 to 10-day-old seedlings and 1-cm pieces preconditioned for 48 h on MS medium supplemented with 1 mg/l 2,4-D (2,4-dichlorophenoxy acetic acid) and 30 g/l sucrose, solidified with 2 g/l Gelrite. The preconditioned hypocotyl segments were then inoculated with *Agrobacterium* grown overnight to an OD600=0.8 in liquid LB medium. The *Agrobacterium* cells are pelleted by centrifugation and re-suspended in liquid callus induction medium with 0.05 mM acetosyringone to induce T-DNA transfer.

Co-cultivation with *Agrobacterium* is performed for 48 h on MS medium with 1 mg/l 2,4-D. Following co-cultivation, the explants are transferred to the same medium with 400 mg/l timentin and 200 mg/l kanamycin to select for transformed cells. After 2 weeks, the explants are transferred to MS medium to promote organogenesis containing 4 mg/l BAP (6-benzylaminopurine), 2 mg/l zeatin, 5 mg/l silver nitrate, 400 mg/l timentin, 200 mg/l kanamycin and 30 g/l sucrose, solidified with 2 g/l Gelrite. After an additional 2 weeks, the tissue is transferred to MS medium containing 3 mg/l BAP, 2 mg/l zeatin, the same antibiotics, 30 g/l sucrose and 2 g/l Gelrite for shoot development. To encourage shoot elongation, the shoots are transferred to MS medium with 0.05 mg/l BAP, 30 g/l sucrose, antibiotics as above, solidified with 3 g/l Gelrite. The elongated shoots are rooted on a medium containing half-strength MS salts, 10 mg/l sucrose, 3 g/l Gelrite, 5 mg/l IBA, and 400 mg/l timentin and 200 mg/l kanamycin. The cultures are incubated at 25±2° C., 16/8-h (light/dark) photoperiod. The rooted shoots are transferred to soil and grown at 20° C. 20, 16/8 h (light/dark) photoperiod. To prevent desiccation, the plants are initially covered with a plastic dome.

Floral Dip Transformation in *Brassica* Ssp. To Generate ACC2 Defective Plants

For *Agrobacterium*-mediated floral dip transformation of *Brassica napus*, for example cv. Westar, more recent protocols that do not require vacuum infiltration are preferred. Verma et al. (2008) and Tan et al. (2011) report such protocols. Verma et al. (2008) recommends growing up the *Agrobacterium* strain in a selective medium, harvesting the cells by centrifugation and then re-suspending them in transformation medium comprising half MS salts, 5% sucrose, 0.05% Silwet L-77 to obtain the desired density (OD600=0.8 to 2.0). Plants are inoculated by submerging inflorescences in the bacterial suspension for one minute and then the inflorescences are wrapped with Saran wrap for 24 h to maintain the humidity. Seeds are collected at maturity and germinated on a selective medium to identify T1 seedlings by the expression plant marker encoded in the T-DNA.

A variant of this protocol is described by (Tan et al., 2011). *Agrobacterium* cultures carrying a target construct are collected by centrifugation and then resuspended in a solution containing 0.53 MS salts, 3% Sucrose, 0.1% Silwet L-77, 2 mg/L 6-benzyladenine, and 8 mg/L acetosyringone. The inflorescence of flowering plants is dipped into a beaker containing the *Agrobacterium* culture for 1 to 2 min with gentle agitation, and the treated inflorescence is wrapped with Saran wrap to keep the flowers most. The plants are treated three times at two day intervals, then the plants are allowed to grow to maturation. Seeds harvested from the transformed plants were surface sterilized and sown on the MS medium containing the plant marker encoded in the T-DNA. If kanamycin resistance is the plant marker, 200 mg/L kanamycin is used to screen for putative transformants. The putative transformants are identified upon the initiation of the first pair of green true leaves. Additional protocols for floral dip transformation are listed in Table 3 below.

TABLE 3

| Species | Reference |
| --- | --- |
| *Brassica rapa* L. ssp *chinensis* | (Qing et al., 2000) |
| *Brassica campestris* L. ssp *chinensis* | (Liu et al., 1998) |
| *B. napus* | (Wang et al., 2003; Wang et al., 2005; Tan et al., 2011) |
| *B. napus*, *B. carinata*, high freq. | (Verma et al., 2008) |
| *Camelina sativa* | (Lu and Kang, 2008) |

There are several *Agrobacterium* vector systems that have been described for CRISPR/Cas mutagenesis in plants (Belhaj et al., 2013; Li et al., 2014). We prefer the system described by Mao et al. for its simplicity (Mao et al., 2013). When a population of homozygous ACC2 knockout or biallelic mutant population is obtained, the seeds will be germinated on spectinomycin medium to identify the ACC2 defective plants by spectinomycin sensitivity (Parker et al., 2014). The type of knockout mutation will be verified by sequencing the target region and the progeny will be used as recipient in chloroplast transformation experiments. *Brassica juncea* is also an oilseed crop. The genomics of this crop is relatively undeveloped. However, guide RNAs to knock-out the ACC2 gene can be designed using the principles outlined for the other Brassicaceae species as described herein above.

TABLE 3

Identification of guide RNAs in the N-terminal extension of the ACC2 gene in Brassicaceae species. Shown are the N-terminal protein sequence, the corresponding cDNA sequence and the potential gRNAs.

>A. thaliana ACC2 (At1g36180)

>MEMRALGSSCSTGNGGSAPITLTNISPWITTVFPSTVKLRSSLRTFKGVSSRVRTFKGVS
STRVLSRTKQQFPLFCFLNPDPISFLENDVSEAERTVVLP (SEQ ID NO: 5)

>ATGGAGATGAGAGCTTTGGGTTCTTCGTGTTCTACTGGTAATGGAGGTTCTGCTCC
GATTACCCTCACGAATATATCTCCATGGATCACAACAGTTTTTCCGTCGACAGTGAA
GCTGAGAAGTAGTTTGAGAACCTTCAAAGGAGTTTCGTCAAGAGTGAGAACCTTTA
AAGGAGTTTCTTCGACAAGAGTTTTGTCTCGGACCAAACAACAGTTTCCTCTGTTTTG
TTTCCTAAACCCTGATCCGATCTCCTTCTTGGAAAATGATGTATCTGAAGCTGAAAG
GACAGTAGTTTTACCG (SEQ ID NO: 6)

For potential gRNAs, see SEQ ID NO. 239-254 below.
> A. lyrata ACC2 (XM_GG2891167.1)

>MEMRALVSSCATGNGGSDPFSFTKVSPWITTVGGKDRDFPTTVKLRTSMRTFKGVSIR
GRTFKGVSTRVLSRNKQQFPLFCFLNPDPTSFRDNDISEAQR (SEQ ID NO: 7)

TABLE 3-continued

Identification of guide RNAs in the N-terminal extension of the ACC2 gene in Brassicaceae species. Shown are the N-terminal protein sequence, the corresponding cDNA sequence and the potential gRNAs.

>5'-3'
ATGGAGATGAGAGCTTTGGTTTCTTCGTGTGCTACCGGTAATGGAGGTTCTGATCCG
TTTAGCTTCACGAAAGTTTCTCCATGGATCACAACAGTTGGTGGTAAGGACAGAGAT
TTTCCAACGACAGTGAAGCTAAGAACTAGTATGAGAACCTTTAAAGGAGTTTCTATA
AGAGGGAGAACCTTTAAAGGAGTTTCGACAAGAGTTTTGTCTCGGAACAAACAACA
GTTTCCTCTGTTTTGTTTCCTAAACCCTGATCCGACCTCCTTCCGGGATAATGATATA
TCTGAAGCTCAAAGG (SEQ ID NO: 8)

TTGGTTTCTTCGTGTGCTAC CGG (SEQ ID NO: 9)

TCTTCGTGTGCTACCGGTAA TGG (SEQ ID NO: 10)

TCGTGTGCTACCGGTAATGG AGG (SEQ ID NO: 11)

GCTTCACGAAAGTTTCTCCA TGG (SEQ ID NO: 12)

TCTCCATGGATCACAACAGT TGG (SEQ ID NO: 13)

CCATGGATCACAACAGTTGG TGG (SEQ ID NO: 14)

GATCACAACAGTTGGTGGTA AGG (SEQ ID NO: 15)

ACTAGTATGAGAACCTTTAA AGG (SEQ ID NO: 16)

TTTAAAGGAGTTTCTATAAG AGG (SEQ ID NO: 17)

ATAAGAGGGAGAACCTTTAA AGG (SEQ ID NO: 18)

TTTCGACAAGAGTTTTGTCT CGG (SEQ ID NO: 19)

ACCCTGATCCGACCTCCTTC CGG (SEQ ID NO: 20)

ATGATATATCTGAAGCTCAA AGG (SEQ ID NO: 21)

>3'-5'
CCTTTGAGCTTCAGATATATCATTATCCCGGAAGGAGGTCGGATCAGGGTTTAGGAA
ACAAAACAGAGGAAACTGTTGTTTGTTCCGAGACAAAACTCTTGTCGAAACTCCTTT
AAAGGTTCTCCCTCTTATAGAAACTCCTTTAAAGGTTCTCATACTAGTTCTTAGCTTC
ACTGTCGTTGGAAAATCTCTGTCCTTACCACCAACTGTTGTGATCCATGGAGAAACT
TTCGTGAAGCTAAACGGATCAGAACCTCCATTACCGGTAGCACACGAAGAAACCAA
AGCTCTCATCTCCAT (SEQ ID NO: 22)

CTTCAGATATATCATTATCC CGG (SEQ ID NO: 23)

AGATATATCATTATCCCGGA AGG (SEQ ID NO: 24)

TATATCATTATCCCGGAAGG AGG (SEQ ID NO: 25)

TCATTATCCCGGAAGGAGGT CGG (SEQ ID NO: 26)

TCCCGGAAGGAGGTCGGATC AGG (SEQ ID NO: 27)

CCCGGAAGGAGGTCGGATCA GGG (SEQ ID NO: 28)

AGGAGGTCGGATCAGGGTTT AGG (SEQ ID NO: 29)

GGGTTTAGGAAACAAAACAG AGG (SEQ ID NO: 30)

TCTTGTCGAAACTCCTTTAA AGG (SEQ ID NO: 31)

TCTTATAGAAACTCCTTTAA AGG (SEQ ID NO: 32)

GTTCTTAGCTTCACTGTCGT TGG (SEQ ID NO: 33)

CCACCAACTGTTGTGATCCA TGG (SEQ ID NO: 34)

GAAACTTTCGTGAAGCTAAA CGG (SEQ ID NO: 35)

CGGATCAGAACCTCCATTAC CGG (SEQ ID NO: 36)

>C. sativa ACC2-1 (LOC104777495)
>MEMRALVSSYSTGNGGSDPISLTNGSPWITTVGGGASTMDREFPLTVKLGSSMRAFKG
VSTTTVLSRTKQQFPLVCLARNNANSTDPTSFWENDISEVQR (SEQ ID NO: 37)

TABLE 3-continued

Identification of guide RNAs in the N-terminal extension of the ACC2 gene in Brassicaceae species. Shown are the N-terminal protein sequence, the corresponding cDNA sequence and the potential gRNAs.

```
>5'-3'
ATGGAGATGAGAGCTTTGGTTTCTTCGTATTCTACCGGTAATGGAGGTTCTGATCCG
ATCAGCCTCACGAATGGTTCTCCATGGATCACAACAGTTGGTGGTGGTGCAAGTACC
ATGGACAGAGAGTTTCCATTGACTGTGAAGCTGGGAAGTAGTATGAGAGCCTTCAA
AGGAGTAAGCACAACAACAGTTTTGTCTCGGACCAAACAACAGTTTCCTCTGGTATG
CTTAGCAAGAAACAATGCGAACAGCACTGATCCGACCTCGTTCTGGGAGAATGATA
TATCTGAAGTTCAAAGG (SEQ ID NO: 38)

TTGGTTTCTTCGTATTCTAC CGG (SEQ ID NO: 39)

TCTTCGTATTCTACCGGTAA TGG (SEQ ID NO: 40)

TCGTATTCTACCGGTAATGG AGG (SEQ ID NO: 41)

GATCCGATCAGCCTCACGAA TGG (SEQ ID NO: 42)

GCCTCACGAATGGTTCTCCA TGG (SEQ ID NO: 43)

TCTCCATGGATCACAACAGT TGG (SEQ ID NO: 44)

CCATGGATCACAACAGTTGG TGG (SEQ ID NO: 45)

TGGATCACAACAGTTGGTGG TGG (SEQ ID NO: 46)

TGGTGGTGGTGCAAGTACCA TGG (SEQ ID NO: 47)

GTTTCCATTGACTGTGAAGC TGG (SEQ ID NO: 48)

AGTAGTATGAGAGCCTTCAA AGG (SEQ ID NO: 49)

GCACAACAACAGTTTTGTCT CGG (SEQ ID NO: 50)

GACCAAACAACAGTTTCCTC TGG (SEQ ID NO: 51)

GCACTGATCCGACCTCGTTC TGG (SEQ ID NO: 52)

ATGATATATCTGAAGTTCAA AGG (SEQ ID NO: 53)

>3'-5'
CCTTTGAACTTCAGATATATCATTCTCCCAGAACGAGGTCGGATCAGTGCTGTTCGC
ATTGTTTCTTGCTAAGCATACCAGAGGAAACTGTTGTTTGGTCCGAGACAAAACTGT
TGTTGTGCTTACTCCTTTGAAGGCTCTCATACTACTTCCCAGCTTCACAGTCAATGGA
AACTCTCTGTCCATGGTACTTGCACCACCACCAACTGTTGTGATCCATGGAGAACCA
TTCGTGAGGCTGATCGGATCAGAACCTCCATTACCGGTAGAATACGAAGAAACCAA
AGCTCTCATCTCCAT (SEQ ID NO: 54)

TATATCATTCTCCCAGAACG AGG (SEQ ID NO: 55)

TCATTCTCCCAGAACGAGGT CGG (SEQ ID NO: 56)

TTTCTTGCTAAGCATACCAG AGG (SEQ ID NO: 57)

TACCAGAGGAAACTGTTGTT TGG (SEQ ID NO: 58)

TGTTGTGCTTACTCCTTTGA AGG (SEQ ID NO: 59)

CTTCCCAGCTTCACAGTCAA TGG (SEQ ID NO: 60)

CAATGGAAACTCTCTGTCCA TGG (SEQ ID NO: 61)

CCACCAACTGTTGTGATCCA TGG (SEQ ID NO: 62)

TCCATGGAGAACCATTCGTG AGG (SEQ ID NO: 63)

GAACCATTCGTGAGGCTGAT CGG (SEQ ID NO: 64)

CGGATCAGAACCTCCATTAC CGG (SEQ ID NO: 65)

>C. sativa ACC2-2 (LOC104742086) variant1
>MEMRALVSSCSTGNGGSDPISLTNGSPWITTVGGGASTMDREFPATVKLGSSMRAFKG
VSTITVLSRTKQQFPLVCLARNNGNSTDPTSFWENDISETQR (SEQ ID NO: 66)

>5'-3'
ATGGAGATGAGAGCTTTGGTTTCTTCGTGTTCTACGGGGAATGGAGGGTCTGATCCG
ATCAGCCTCACGAATGGTTCTCCATGGATCACAACAGTTGGTGGTGGTGCAAGTACC
```

TABLE 3-continued

Identification of guide RNAs in the N-terminal extension of the ACC2 gene in Brassicaceae species. Shown are the N-terminal protein sequence, the corresponding cDNA sequence and the potential gRNAs.

ATGGACAGAGAGTTTCCAGCGACTGTGAAGCTGGGAAGTAGTATGAGAGCCTTCAA
AGGAGTAAGCACAATAACAGTTCTGTCTCGGACCAAACAACAGTTTCCTCTGGTATG
CTTAGCAAGAAACAACGGAAACAGCACTGATCCGACCTCGTTCTGGGAGAACGATA
TATCTGAAACTCAAAGG (SEQ ID NO: 67)

TTTGGTTTCTTCGTGTTCTA CGG (SEQ ID NO: 68)

TTGGTTTCTTCGTGTTCTAC GGG (SEQ ID NO: 69)

TGGTTTCTTCGTGTTCTACG GGG (SEQ ID NO: 70)

TCTTCGTGTTCTACGGGGAA TGG (SEQ ID NO: 71)

TCGTGTTCTACGGGGAATGG AGG (SEQ ID NO: 72)

GATCCGATCAGCCTCACGAA TGG (SEQ ID NO: 73)

GCCTCACGAATGGTTCTCCA TGG (SEQ ID NO: 74)

TCTCCATGGATCACAACAGT TGG (SEQ ID NO: 75)

CCATGGATCACAACAGTTGG TGG (SEQ ID NO: 76)

TGGATCACAACAGTTGGTGG TGG (SEQ ID NO: 77)

TGGTGGTGGTGCAAGTACCA TGG (SEQ ID NO: 78)

GTTTCCAGCGACTGTGAAGC TGG (SEQ ID NO: 79)

AGTAGTATGAGAGCCTTCAA AGG (SEQ ID NO: 80)

GCACAATAACAGTTCTGTCT CGG (SEQ ID NO: 81)

GACCAAACAACAGTTTCCTC TGG (SEQ ID NO: 82)

GTATGCTTAGCAAGAAACAA CGG (SEQ ID NO: 83)

GCACTGATCCGACCTCGTTC TGG (SEQ ID NO: 84)

ACGATATATCTGAAACTCAA AGG (SEQ ID NO: 85)

>3'-5'
CCTTTGAGTTTCAGATATATCGTTCTCCCAGAACGAGGTCGGATCAGTGCTGTTTCCG
TTGTTTCTTGCTAAGCATACCAGAGGAAACTGTTGTTTGGTCCGAGACAGAACTGTT
ATTGTGCTTACTCCTTTGAAGGCTCTCATACTACTTCCCAGCTTCACAGTCGCTGGAA
ACTCTCTGTCCATGGTACTTGCACCACCACCAACTGTTGTGATCCATGGAACCAT
TCGTGAGGCTGATCGGATCAGACCCTCCATTCCCCGTAGAACACGAAGAAACCAAA
GCTCTCATCTCCAT (SEQ ID NO: 86)

TATATCGTTCTCCCAGAACG AGG (SEQ ID NO: 87)

TCGTTCTCCCAGAACGAGGT CGG (SEQ ID NO: 88)

TTTCTTGCTAAGCATACCAG AGG (SEQ ID NO: 89)

TACCAGAGGAAACTGTTGTT TGG (SEQ ID NO: 90)

TATTGTGCTTACTCCTTTGA AGG (SEQ ID NO: 91)

CTTCCCAGCTTCACAGTCGC TGG (SEQ ID NO: 92)

CGCTGGAAACTCTCTGTCCA TGG (SEQ ID NO: 93)

CCACCAACTGTTGTGATCCA TGG (SEQ ID NO: 94)

TCCATGGAGAACCATTCGTG AGG (SEQ ID NO: 95)

GAACCATTCGTGAGGCTGAT CGG (SEQ ID NO: 96)

>C. rubella ACC2 (CARUB_v1GG08063mg)
>MEMRALVSSCSTGNGGSDPISLTNVSPWITTVGGGASSIDREFPTTVKLGSSLRTFKGVS
STTVLSRTKQQFPLVCLARNNANSTDPTLFWENDISEAQS (SEQ ID NO: 97)

>5'-3'
ATGGAGATGAGAGCTTTGGTTTCTTCGTGTTCTACCGGTAATGGAGGTTCTGATCCG
ATTAGCCTCACGAATGTTTCTCCATGGATCACAACAGTTGGTGGTGGTGCAAGTTCC

TABLE 3-continued

Identification of guide RNAs in the N-terminal extension of the ACC2 gene in Brassicaceae species. Shown are the N-terminal protein sequence, the corresponding cDNA sequence and the potential gRNAs.

ATTGACAGAGAGTTTCCAACGACTGTGAAGCTGGGAAGTAGTCTGAGAACTTTCAA
AGGAGTAAGCTCTACGACAGTTTTGTCTCGGACCAAACAACAGTTTCCTCTGGTTTG
TTTAGCAAGAAACAATGCCAACAGCACTGATCCAACCTTGTTCTGGGAAAATGACAT
ATCTGAAGCTCAAAGC (SEQ ID NO: 98)

TTGGTTTCTTCGTGTTCTAC CGG (SEQ ID NO: 99)

TCTTCGTGTTCTACCGGTAA TGG (SEQ ID NO: 100)

TCGTGTTCTACCGGTAATGG AGG (SEQ ID NO: 101)

GCCTCACGAATGTTTCTCCA TGG (SEQ ID NO: 102)

TCTCCATGGATCACAACAGT TGG (SEQ ID NO: 103)

CCATGGATCACAACAGTTGG TGG (SEQ ID NO: 104)

TGGATCACAACAGTTGGTGG TGG (SEQ ID NO: 142)

GTTTCCAACGACTGTGAAGC TGG (SEQ ID NO: 105)

AGTAGTCTGAGAACTTTCAA AGG (SEQ ID NO: 106)

GCTCTACGACAGTTTTGTCT CGG (SEQ ID NO: 107)

GACCAAACAACAGTTTCCTC TGG (SEQ ID NO: 108)

GCACTGATCCAACCTTGTTC TGG (SEQ ID NO: 109)

>3'-5'
GCTTTGAGCTTCAGATATGTCATTTTCCCAGAACAAGGTTGGATCAGTGCTGTTGGC
ATTGTTTCTTGCTAAACAAACCAGAGGAAACTGTTGTTTGGTCCGAGACAAAACTGT
CGTAGAGCTTACTCCTTTGAAAGTTCTCAGACTACTTCCCAGCTTCACAGTCGTTGGA
AACTCTCTGTCAATGGAACTTGCACCACCACCAACTGTTGTGATCCATGGAGAAACA
TTCGTGAGGCTAATCGGATCAGAACCTCCATTACCGGTAGAACACGAAGAAACCAA
AGCTCTCATCTCCAT (SEQ ID NO: 110)

TATGTCATTTTCCCAGAACA AGG (SEQ ID NO: 111)

TCATTTTCCCAGAACAAGGT TGG (SEQ ID NO: 112)

CAAGGTTGGATCAGTGCTGT TGG (SEQ ID NO: 113)

TTTCTTGCTAAACAAACCAG AGG (SEQ ID NO: 114)

AACCAGAGGAAACTGTTGTT TGG (SEQ ID NO: 115)

CTTCCCAGCTTCACAGTCGT TGG (SEQ ID NO: 116)

CGTTGGAAACTCTCTGTCAA TGG (SEQ ID NO: 117)

CCACCAACTGTTGTGATCCA TGG (SEQ ID NO: 118)

TCCATGGAGAAACATTCGTG AGG (SEQ ID NO: 119)

GAAACATTCGTGAGGCTAAT CGG (SEQ ID NO: 120)

CGGATCAGAACCTCCATTAC CGG (SEQ ID NO: 121)

>B. oleracea ACC2 (LOC106301042)

>MEMRALVSCSAAGNGASDRFRLSNVSPWITSARGASGSDSPATVKLRSSSMIRAFKGV
SIYKNKTRRNVLSQRNKQFRPMAYLGRKDLSSPDPTSFCDND (SEQ ID NO: 122)

>5'-3'
ATGGAGATGAGAGCTTTGGTTTCGTGTTCTGCTGCCGGAAATGGAGCTTCTGATCGG
TTTAGACTCTCCAATGTTTCACCATGGATCACATCTGCTCGTGGTGCAAGTGGCAGT
GACTCCCCAGCCACAGTGAAGCTGAGAAGCAGCTCTATGATTAGAGCTTTCAAAGG
AGTTTCGATTTACAAAAACAAGACCAGAAGAAATGTTCTGTCTCAAAGGAACAAAC
AGTTCCGTCCTATGGCCTACTTAGGAAGGAAGGACTTGAGCAGCCCTGATCCGACCT
CCTTCTGCGATAATGAT (SEQ ID NO: 123)

TTGGTTTCGTGTTCTGCTGC CGG (SEQ ID NO: 124)

TCGTGTTCTGCTGCCGGAAA TGG (SEQ ID NO: 125)

TABLE 3-continued

Identification of guide RNAs in the N-terminal extension of the ACC2 gene in Brassicaceae species. Shown are the N-terminal protein sequence, the corresponding cDNA sequence and the potential gRNAs.

CCGGAAATGGAGCTTCTGAT CGG (SEQ ID NO: 126)

GACTCTCCAATGTTTCACCA TGG (SEQ ID NO: 127)

CCATGGATCACATCTGCTCG TGG (SEQ ID NO: 128)

ACATCTGCTCGTGGTGCAAG TGG (SEQ ID NO: 129)

TCTATGATTAGAGCTTTCAA AGG (SEQ ID NO: 130)

GAAGAAATGTTCTGTCTCAA AGG (SEQ ID NO: 131)

GAACAAACAGTTCCGTCCTA TGG (SEQ ID NO: 132)

TTCCGTCCTATGGCCTACTT AGG (SEQ ID NO: 133)

GTCCTATGGCCTACTTAGGA AGG (SEQ ID NO: 134)

TATGGCCTACTTAGGAAGGA AGG (SEQ ID NO: 135)

3'-5'
ATCATTATCGCAGAAGGAGGTCGGATCAGGGCTGCTCAAGTCCTTCCTTCCTAAGTA
GGCCATAGGACGGAACTGTTTGTTCCTTTGAGACAGAACATTTCTTCTGGTCTTGTTT
TTGTAAATCGAAACTCCTTTGAAAGCTCTAATCATAGAGCTGCTTCTCAGCTTCACTG
TGGCTGGGGAGTCACTGCCACTTGCACCACGAGCAGATGTGATCCATGGTGAAACA
TTGGAGAGTCTAAACCGATCAGAAGCTCCATTTCCGGCAGCAGAACACGAAACCAA
AGCTCTCATCTCCAT (SEQ ID NO: 136)

TCATTATCGCAGAAGGAGGT CGG (SEQ ID NO: 137)

TCGCAGAAGGAGGTCGGATC AGG (SEQ ID NO: 138)

CAAGTCCTTCCTTCCTAAGT AGG (SEQ ID NO: 139)

TTCCTTCCTAAGTAGGCCAT AGG (SEQ ID NO: 140)

TTCCTAAGTAGGCCATAGGA CGG (SEQ ID NO: 141)

TTGAGACAGAACATTTCTTC TGG (SEQ ID NO: 143)

GCTGCTTCTCAGCTTCACTG TGG (SEQ ID NO: 144)

CTTCTCAGCTTCACTGTGGC TGG (SEQ ID NO: 145)

TTCTCAGCTTCACTGTGGCT GGG (SEQ ID NO: 146)

TCTCAGCTTCACTGTGGCTG GGG (SEQ ID NO: 147)

CCACGAGCAGATGTGATCCA TGG (SEQ ID NO: 148)

TGTGATCCATGGTGAAACAT TGG (SEQ ID NO: 149)

CCGATCAGAAGCTCCATTTC CGG (SEQ ID NO: 150)

>B. napus ACC2-1: Y10302
MEMRALVSCSAAGNGASDRFRLSNVSPWITSARGASGSDSPATVKLGSSSMIRAFKGVS
IYKNKTRRNVLSQRNKQFRPMAYLGRKDLSSPDPTSFCDNDISEPQGTGSINGNDHSAV
RVSQVDEFCKAHGGKRPIHSILVATNGMAAVKLIRSVRAWSYQTFGSEKSISLVAMATP
EDMRINAEHIRIADQFMQVPGGTNNNNYANVHLIVEMAQATGVDAVWPGWGHASENP
ELPDALKAKGVIFLGPTAASMLALGDKIGSSLIAQAADVPTLPWSGSHVKIPPGSSMVTIP
EEMYRQACVYTTEEAVASCQVVGYPAMIKASWGGGGKGIREVHDDDEVRTLFKQVQG
EVPGSPIFIMKVASQSRHL (SEQ ID NO: 151)

>5'-3' 1$^{ST}$ EXON
ATGGAGATGAGAGCTTTAGTTTCGTGTTCTGCTGCCGGAAATGGAGCTTCTGATCGG
TTTAGACTCTCCAATGTTTCACCATGGATCACATCAGCTCGTGGTGCAAGTGGCAGT
GACTCCCCAGCCACAGTGAAGCTGGGAAGCAGCTCTATGATTAGAGCTTTCAAAGG
CGTTTCGATTTACAAAAACAAGACCAGAAGGAATGTTCTGTCTCAAAGGAACAAAC
AGTTCCGTCCTATGGCCTACTTAGGAAGGAAGGACTTGAGCAGCCCTGATCCGACCT
CCTTCTGCGATAATG (SEQ ID NO: 152)

TTAGTTTCGTGTTCTGCTGC CGG (SEQ ID NO: 153)

TCGTGTTCTGCTGCCGGAAA TGG (SEQ ID NO: 154)

CCGGAAATGGAGCTTCTGAT CGG (SEQ ID NO: 155)

TABLE 3-continued

Identification of guide RNAs in the N-terminal extension of the ACC2 gene in Brassicaceae species. Shown are the N-terminal protein sequence, the corresponding cDNA sequence and the potential gRNAs.

GACTCTCCAATGTTTCACCA TGG (SEQ ID NO: 156)

CCATGGATCACATCAGCTCG TGG (SEQ ID NO: 157)

ACATCAGCTCGTGGTGCAAG TGG (SEQ ID NO: 158)

CTCCCCAGCCACAGTGAAGC TGG (SEQ ID NO: 159)

TCCCCAGCCACAGTGAAGCT GGG (SEQ ID NO: 160)

TCTATGATTAGAGCTTTCAA AGG (SEQ ID NO: 161)

TTTACAAAAACAAGACCAGA AGG (SEQ ID NO: 162)

GAAGGAATGTTCTGTCTCAA AGG (SEQ ID NO: 163)

GAACAAACAGTTCCGTCCTA TGG (SEQ ID NO: 164)

TTCCGTCCTATGGCCTACTT AGG (SEQ ID NO: 165)

GTCCTATGGCCTACTTAGGA AGG (SEQ ID NO: 166)

TATGGCCTACTTAGGAAGGA AGG (SEQ ID NO: 167)

>3'-5'
CATTATCGCAGAAGGAGGTCGGATCAGGGCTGCTCAAGTCCTTCCTTCCTAAGTAGG
CCATAGGACGGAACTGTTTGTTCCTTTGAGACAGAACATTCCTTCTGGTCTTGTTTTT
GTAAATCGAAACGCCTTTGAAAGCTCTAATCATAGAGCTGCTTCCCAGCTTCACTGT
GGCTGGGGAGTCACTGCCACTTGCACCACGAGCTGATGTGATCCATGGTGAAACATT
GGAGAGTCTAAACCGATCAGAAGCTCCATTTCCGGCAGCAGAACACGAAACTAAAG
CTCTCATCTCCAT (SEQ ID NO: 168)

TCGCAGAAGGAGGTCGGATC AGG (SEQ ID NO: 169)

CGCAGAAGGAGGTCGGATCA GGG (SEQ ID NO: 170)

CAAGTCCTTCCTTCCTAAGT AGG (SEQ ID NO: 171)

TTCCTTCCTAAGTAGGCCAT AGG (SEQ ID NO: 172)

TTCCTAAGTAGGCCATAGGA CGG (SEQ ID NO: 173)

TTGAGACAGAACATTCCTTC TGG (SEQ ID NO: 174)

CTTCCCAGCTTCACTGTGGC TGG (SEQ ID NO: 175)

TTCCCAGCTTCACTGTGGCT GGG (SEQ ID NO: 176)

TCCCAGCTTCACTGTGGCTG GGG (SEQ ID NO: 177)

CCACGAGCTGATGTGATCCA TGG (SEQ ID NO: 178)

TGTGATCCATGGTGAAACAT TGG (SEQ ID NO: 179)

CCGATCAGAAGCTCCATTTC CGG (SEQ ID NO: 180)

>B. napus ACC2-2: X77576
MEMRALVSCSAAGNGASDRFRLSNVSPWITSARGASGSDSPATVKLGSSSMIRAFKGVS
IYKNKTRRNVLSQRNKQFRPMAYLGRKDLSSPDPTSFCDNDISEPQGTGSINGNDHSAV
RVSQVDEFCKAHGGKRPIHRILVATNGMAAVKFIRSVRAWSYQTFGSEKSISLVAMATP
EDMRJNAEHIRIADQFMQVPGGTNNNNYANVHLIVEMAEATGVDAVWPGWGHASENP
ELPDALKAKGVIFLGPTAASMLALGDKIGSSLIAQAADVPTLPWSGSHVKIPPGSSLVTIP
EEMYRQACVYTTEEAVASCQVVGYPAMIKASWGGGGKGIRKVHDDDEVRALFKQVQ
GEVPGSPIFIMKVASQSRHLEVQLLCDQYGNVSALHSRDCSVQRRHQKIIEEGPITVAPR
DTVKKLEQAARRLAKSVNYVGAATVEFLYSMDTGDYFFLELNPR (SEQ ID NO: 181)

>5'-3' 1$^{ST}$ EXON
ATGGAGATGAGAGCTTTGGTTTCGTGTTCTGCTGCCGGAAATGGAGCTTCTGATCGG
TTTAGACTCTCCAATGTTTCACCATGGATCACATCAGCTCGTGGTGCAAGTGGCAGT
GACTCCCCAGCCACAGTGAAGCTGGGAAGCAGCTCTATGATCAGAGCCTTCAAGG
AGTTTCGATTTACAAAAACAAGACCAGAAGAAATGTTTTGTCTCAAAGGAACAAAC
AGTTTCGTCCTATGGCCTACTTAGGAAGGAAGGACTTGAGCAGCCCTGATCCGACCT
CCTTCTGCGATAATG (SEQ ID NO: 182)

TABLE 3-continued

Identification of guide RNAs in the N-terminal extension of the ACC2 gene in Brassicaceae species. Shown are the N-terminal protein sequence, the corresponding cDNA sequence and the potential gRNAs.

TTGGTTTCGTGTTCTGCTGC CGG (SEQ ID NO: 183)

TCGTGTTCTGCTGCCGGAAA TGG (SEQ ID NO: 184)

CCGGAAATGGAGCTTCTGAT CGG (SEQ ID NO: 185)

GACTCTCCAATGTTTCACCA TGG (SEQ ID NO: 186)

CCATGGATCACATCAGCTCG TGG (SEQ ID NO: 187)

ACATCAGCTCGTGGTGCAAG TGG (SEQ ID NO: 188)

CTCCCCAGCCACAGTGAAGC TGG (SEQ ID NO: 189)

TCCCCAGCCACAGTGAAGCT GGG (SEQ ID NO: 190)

TCTATGATCAGAGCCTTCAA AGG (SEQ ID NO: 191)

GAAGAAATGTTTTGTCTCAA AGG (SEQ ID NO: 192)

GAACAAACAGTTTCGTCCTA TGG (SEQ ID NO: 193)

TTTCGTCCTATGGCCTACTT AGG (SEQ ID NO: 194)

GTCCTATGGCCTACTTAGGA AGG (SEQ ID NO: 195)

TATGGCCTACTTAGGAAGGA AGG (SEQ ID NO: 196)

>3'-5'
CATTATCGCAGAAGGAGGTCGGATCAGGGCTGCTCAAGTCCTTCCTTCCTAAGTAGG
CCATAGGACGAAACTGTTTGTTCCTTTGAGACAAAACATTTCTTCTGGTCTTGTTTTT
GTAAATCGAAACTCCTTTGAAGGCTCTGATCATAGAGCTGCTTCCCAGCTTCACTGT
GGCTGGGGAGTCACTGCCACTTGCACCACGAGCTGATGTGATCCATGGTGAAACATT
GGAGAGTCTAAACCGATCAGAAGCTCCATTTCCGGCAGCAGAACACGAAACCAAAG
CTCTCATCTCCAT (SEQ ID NO: 197)

TCGCAGAAGGAGGTCGGATC AGG (SEQ ID NO: 198)

CGCAGAAGGAGGTCGGATCA GGG (SEQ ID NO: 199)

CAAGTCCTTCCTTCCTAAGT AGG (SEQ ID NO: 200)

TTCCTTCCTAAGTAGGCCAT AGG (SEQ ID NO: 201)

TTGAGACAAAACATTTCTTC TGG (SEQ ID NO: 202)

GTAAATCGAAACTCCTTTGA AGG (SEQ ID NO: 203)

GCTGCTTCCCAGCTTCACTG TGG (SEQ ID NO: 204)

CTTCCCAGCTTCACTGTGGC TGG (SEQ ID NO: 205)

TTCCCAGCTTCACTGTGGCT GGG (SEQ ID NO: 206)

TCCCAGCTTCACTGTGGCTG GGG (SEQ ID NO: 207)

CCACGAGCTGATGTGATCCA TGG (SEQ ID NO: 208)

TGTGATCCATGGTGAAACAT TGG (SEQ ID NO: 209)

CCGATCAGAAGCTCCATTTC CGG (SEQ ID NO: 210)

>B. rapa ACC2 (LOC1038715GG)
>MEMRALVSCSAAGNGASDRFRLSNVSPWITSARGASGSDSPATVKLGSSSMIRAFKGV
SIYKNKSRRNVLSQRNKQFRPMAYLGRKDLSSPDPTSFCDND (SEQ ID NO: 211)

>5'-3'
ATGGAGATGAGAGCTTTGGTTTCGTGTTCTGCTGCCGGAAATGGAGCTTCTGATCGG
TTTAGACTCTCCAATGTTTCACCATGGATCACATCAGCTCGTGGTGCAAGTGGCAGT
GACTCCCCAGCCACAGTGAAGCTGGGAAGCAGCTCTATGATCAGAGCCTTCAAGG
AGTTTCGATTTACAAAAACAAGAGCAGAAGAAATGTTCTGTCTCAAAGGAACAAAC
AGTTTCGTCCTATGGCCTACTTAGGAAGGAAGGACTTGAGCAGCCCTGATCCGACCT
CCTTCTGCGATAATGAT (SEQ ID NO: 212)

TTGGTTTCGTGTTCTGCTGC CGG (SEQ ID NO: 213)

TABLE 3-continued

Identification of guide RNAs in the N-terminal extension of the ACC2 gene in Brassicaceae species. Shown are the N-terminal protein sequence, the corresponding cDNA sequence and the potential gRNAs.

TCGTGTTCTGCTGCCGGAAA TGG (SEQ ID NO: 214)

CCGGAAATGGAGCTTCTGAT CGG (SEQ ID NO: 215)

GACTCTCCAATGTTTCACCA TGG (SEQ ID NO: 216)

CCATGGATCACATCAGCTCG TGG (SEQ ID NO: 217)

ACATCAGCTCGTGGTGCAAG TGG (SEQ ID NO: 218)

CTCCCCAGCCACAGTGAAGC TGG (SEQ ID NO: 219)

TCTATGATCAGAGCCTTCAA AGG (SEQ ID NO: 220)

GAAGAAATGTTCTGTCTCAA AGG (SEQ ID NO: 221)

TTTCGTCCTATGGCCTACTT AGG (SEQ ID NO: 223)

GTCCTATGGCCTACTTAGGA AGG (SEQ ID NO: 224)

TATGGCCTACTTAGGAAGGA AGG (SEQ ID NO: 225)

3'-5'
ATCATTATCGCAGAAGGAGGTCGGATCAGGGCTGCTCAAGTCCTTCCTTCCTAAGTA
GGCCATAGGACGAAACTGTTTGTTCCTTTGAGACAGAACATTTCTTCTGCTCTTGTTT
TTGTAAATCGAAACTCCTTTGAAGGCTCTGATCATAGAGCTGCTTCCCAGCTTCACT
GTGGCTGGGGAGTCACTGCCACTTGCACCACGAGCTGATGTGATCCATGGTGAAAC
ATTGGAGAGTCTAAACCGATCAGAAGCTCCATTTCCGGCAGCAGAACACGAAACCA
AAGCTCTCATCTCCAT (SEQ ID NO: 226)

TCATTATCGCAGAAGGAGGT CGG (SEQ ID NO: 227)

TCGCAGAAGGAGGTCGGATC AGG (SEQ ID NO: 228)

CAAGTCCTTCCTTCCTAAGT AGG (SEQ ID NO: 229)

TTCCTTCCTAAGTAGGCCAT AGG (SEQ ID NO: 230)

GTAAATCGAAACTCCTTTGA AGG (SEQ ID NO: 231)

GCTGCTTCCCAGCTTCACTG TGG (SEQ ID NO: 232)

CTTCCCAGCTTCACTGTGGC TGG (SEQ ID NO: 233)

TTCCCAGCTTCACTGTGGCT GGG (SEQ ID NO: 234)

TCCCAGCTTCACTGTGGCTG GGG (SEQ ID NO: 235)

CCACGAGCTGATGTGATCCA TGG (SEQ ID NO: 236)

TGTGATCCATGGTGAAACAT TGG (SEQ ID NO: 237)

CCGATCAGAAGCTCCATTTC CGG (SEQ ID NO: 238)

Deletion of ACC2 Gene in Regenerable RLD and Ws *Arabidopsis* Ecotypes

The bacterial clustered regularly interspaced short palindromic repeats (CRISPR) and CRISPR-associated (Cas) defense system has been rapidly developed as a genome-engineering tool (Belhaj et al., 2013; Mali et al., 2013; Li et al., 2014). In this approach a small RNA guides the Cas9 nuclease to the target site. The nick is then repaired by non-homologous end joining, the process most often resulting in a one-nucleotide insertion or deletion in *Arabidopsis thaliana* (Feng et al., 2014). Because our objective is knocking out the ACC2 gene, we used the same system, an *Agrobacterium* binary transformation vector in which the sgRNA is transcribed under the control of *Arabidopsis* U6 snoRNA promoter (pAtU6) and Cas9 is expressed from the *Arabidopsis* ubiquitin promoter (pAtUBQ1) (Mao et al., 2013).

The 16 guide strands provided below are suitable for this approach.

sequence

TCCATGGAGATATATTCGTG AGG (SEQ ID NO: 239)

CCCTCACGAATATATCTCCA TGG (SEQ ID NO: 240)

CATATATTCGTGAGGGTAT TGG (SEQ ID NO: 241)

CTTCTCAGCTTCACTGTCGA CGG (SEQ ID NO: 242)

```
                                          (SEQ ID NO: 243)
CCATGGGAGATATATTCGTG GGG (SEQ ID NO: 244)
CTTCGACAAGAGTTTTGTCT CGG (SEQ ID NO: 245)
TCAAGAGTGAGAACCTTTAA AGG (SEQ ID NO: 246)
TCTTCGTGTTCTACTGGTAA TGG (SEQ ID NO: 247)
TTGGGTTCTTCGTGTTCTAC TGG (SEQ ID NO: 248)
TGTCGAAGAAACTCCTTTAA AGG (SEQ ID NO: 249)
TCTTGACGAAACTCCTTTGA AGG (SEQ ID NO: 250)
AGTAGTTTGAGAACCTTCAA AGG (SEQ ID NO: 251)
TCGTGTTCTACTGGTAATGG AGG (SEQ ID NO: 252)
GGAAAAACTGTTGTGATCCA TGG (SEQ ID NO: 253)
AAACAGAGGAAACTGTTGTT TGG (SEQ ID NO: 254)
GGGTTTAGGAAACAAAACAG AGG
```

The target for mutagenesis wase exon-1 of the ACC2 coding region encoding the chloroplast transit peptide. This N-terminal extension is absent in the ACC1 gene, which targets its product to the cytoplasm. To design the targeting region of the guide RNA, 240 nucleotides of ACC2 exon-1 were pasted into the guide RNA design at the MIT Optimized CRISPR Design website. The RLD and Ws sequence has a one-nucleotide (A instead of G) mismatch compared to Columbia, a sequence variation that was be considered when designing the sgRNA. The closest off target site in the *Arabidopsis* genome has three mismatches with this target site.

To target the ACC2 sequence CCCT-CACGAATATATCTCCATGG ($2^{nd}$ target site in the list; SEQ ID NO: 240), we cloned two annealed oligonucleotides that form the target site in BbsI-digested CRISPR/Cas9 cassette psgR-Cas9-At (Mao et al., 2013). The oligonucleotides were gattgCCTCACGAATATATCTCCA (SEQ ID NO: 255), and aaacTGGAGATATATTCGTGAGGc (SEQ ID NO: 256). The CRISPR/Cas9 cassette was then cloned in a pCAMBIA2300 *Agrobacterium* binary vector and introduced into *Arabidopsis* by the flower dip protocol (Clough and Bent, 1998). Plants transformed with the CRISPR/Cas9 construct were selected by germinating seeds on kanamycin medium (100 mg/L).

Kanamycin resistant seedlings (T1 generation) were screened for a mutant ACC2 target site by the T7 exonuclease I (T7E1) assay (Xie and Yang, 2013). The T7 endonuclease recognizes and cleaves non-perfectly matched DNA. The ACC2 target region was PCR amplified using forward primer 5'-TCTCTTCCTCCTTAAAAAGCCACA-3' (SEQ ID NO: 257) and reverse primer 5'-CTAGGAT-TCGAAACCAGCGT-3' (SEQ ID NO: 258) using total cellular DNA as template, the amplicons were denatured, reannealed and treated with T7E1. Mismatch caused by CRISPR/Cas9 mutagenesis resulted in T7E1 cleaving the mismatched DNA, that was visualized by gel electrophoresis.

Figure 8:
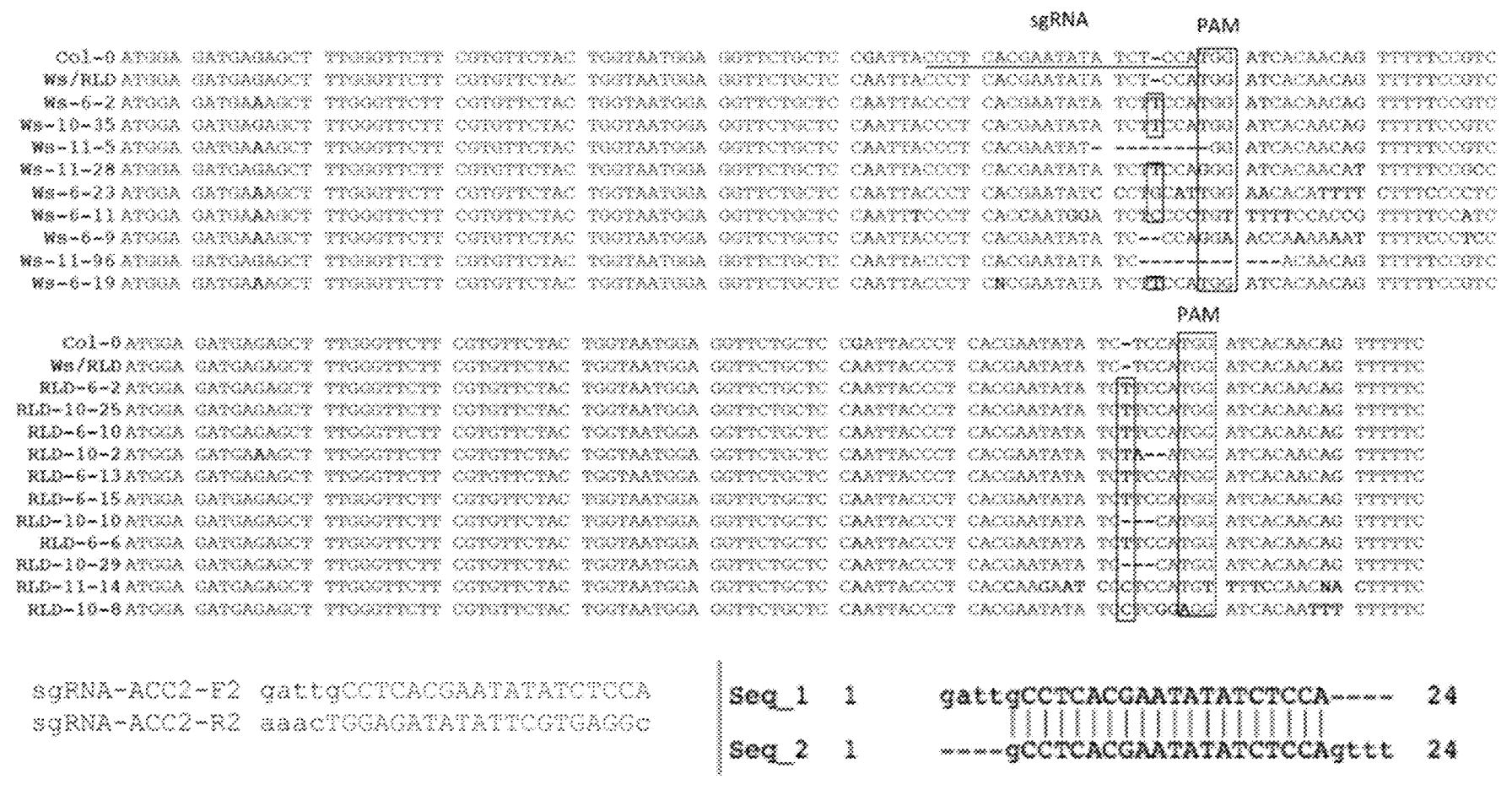
Figure 9:
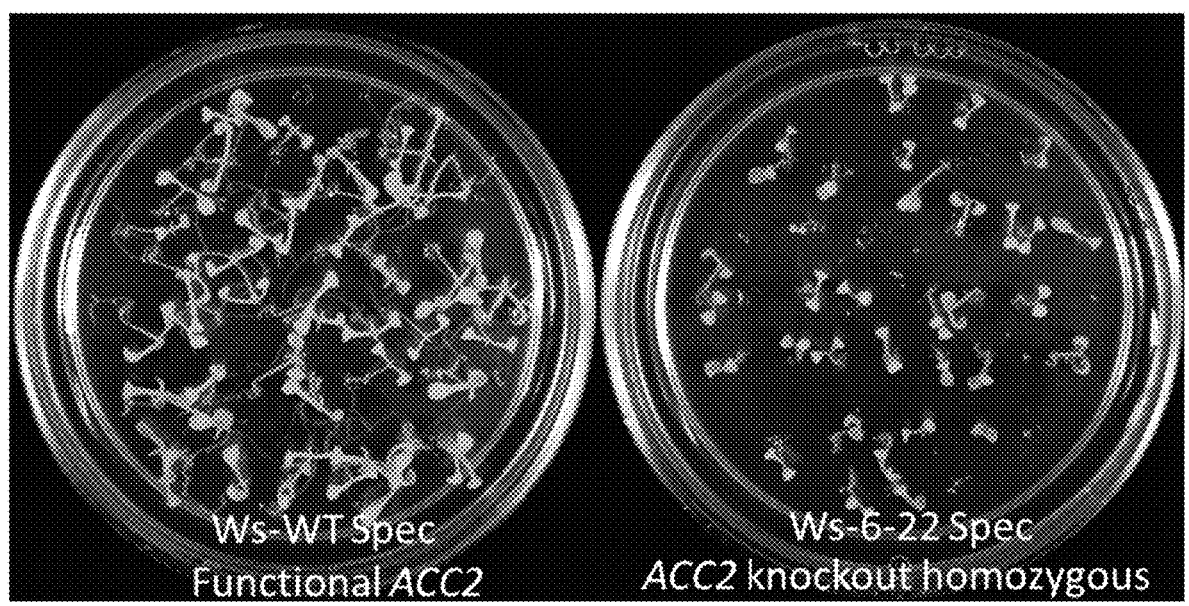
FIG. 9. Ws T3 seed germinated on 100 mg/L spectinomycin medium testing for hypersensitive response. After 2 weeks, the wild-type Ws seedlings bleach but develop primary leaves, in contrast to Ws-2-22 homozygous ACC2 knock-out seedlings which germinate, but do not develop shoot meristem outgrowths on spectinomycin.

Plants carrying mutations in ACC2 gene copies were identified by T7E1 screening the heterozygous T1 seed progeny. Mutations in ACC2 genes were identified in the T2 generation by sequencing PCR amplicons (FIG. 8). The acc2 knockout mutants, in contrast to wild type, do not develop shoot meristem outgrowths when germinated on spectinomycin (Parker et al., 2014). Therefore, we collected seed from the T1 plants, and germinated a small sample on spectinomycin medium to identify non-segregating acc2 knockout populations by spectinomycin sensitivity. An example for seedling spectinomycin hypersensitive reaction is shown in FIG. 9. Note development of primary leaves on the seedlings of the parental Ws line, and the absence of any shoot meristem outgrowth on the hypersensitive Ws-2-22 mutant (Parker et al., 2014). Following this protocol uniform, non-segregating RLD and Ws seed was obtained. Such spectinomycin hypersensitive plants are the suitable recipients for plastid transformation.

Example III

Expression of Heterologous Genes in ACC2-Defective *Brassica* Spp.

Reproducible, high-frequency plastid transformation in the *Brassicae* oilseed and vegetable crops enables plastid genome engineering in spectinomycin hypersensitive *Brassica* spp. for a variety of biotechnological applications.

One application is replacement of part or the entire plastid genome with synthetic DNA. For example, the efficiency of sunlight to biomass conversion can be improved by introducing genes or groups of genes from other crop species, algae, and photosynthetic bacteria (Gimpel et al., 2016; Hanson et al., 2016; Sharwood et al., 2016).

Expression of plastid transgenes throughout the plant is desirable for some applications, for example tolerance to herbicides such as phosphinothricin (PPT) (Lutz et al., 2001; Ye et al., 2003), glyphosate (Ye et al., 2003), sulfonylurea, pyrimidinylcarboxylate (Shimizu et al., 2008) and diketonitrile (Dufourmantel et al., 2007). Equally useful are plastid expression of insecticidal protein genes (U.S. Pat. No. 5,545,818) and double-stranded RNAs that are toxic to insects (Zhang et al., 2015). The herbicide resistance and insecticidal genes are introduced by linkage to the selective spectinomycin resistance (aadA gene) marker. When uniform transformation of plastid genomes is obtained, the marker gene can be excised by a site-specific recombinase that targets sites flanking the marker gene. Various marker excision systems are suitable including the Cre/loxP or PhiC31/Int systems (as described in U.S. Pat. Nos. 7,217,860 and 8,841,511) or the BxB1 (Shao et al., 2014), ParA-MRS, and CinH-Rs2 (Shao et al., 2017) site-specific recombination systems.

Figure 10:
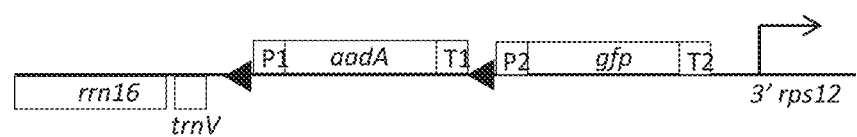
FIG. 10. Schematic design of a *Brassica napus* plastid transformation vector is shown. The plastid targeting sequence comprises the rrn16 targeting region (nucleotides 135473-137978 in GenBank accession KP161617). The vector carries a target site flanked selectable aadA marker gene. The recombinase target sites are marked with triangles. The marker gene and gene of interest have different promoters (P1, P2) and terminators (T1, T2) to avoid deletions by recombination via duplicates sequences.

Particularly effective for the recovery of transplastomic events are the PrrnLatpB/TrbcL, PrrnLatpB/TpsbA, PrrnLrbcL/TpsbA, PrrnLT7g10/TrbcL promoter/terminator cassettes (Kuroda and Maliga, 2001, 2001). Genes of interest may also be expressed using cassettes previously described in U.S. Pat. Nos. 5,977,402, 6,297,054, 6, 376, 744, 6,472,568, 6,624,296, 6,987,215, 7,176,355, 8,143,474. FIG. 10 shows a schematic design of a plastid transformation vector having a *Brassica napus* plastid targeting sequence containing the rrn16 targeting region (nucleotides 135473-137978 in GenBank accession KP161617) and carrying a recombinase target site-flanked selectable aadA marker and a gene of interest.

Tissue-specific expression of plastid genes is desirable but thus far no practical system has been available to achieve this objective. We describe here seed-specific expression of proteins in plastids based on a transgene incorporated in the plastid genome that is regulated by a nuclear gene with a seed-specific promoter. The elements of the system are depicted in FIG. 11A. In a *Brassica* spp. the transgene encoding green fluorescent protein (or particular gene of interest) is present in the leaf cell, but is not translated in the absence of a modified PPR10 RNA binding protein. The engineered *Zea mays* PPR10GG protein gene that is required for expression is present in the nucleus, but is not active because it is under the control of a seed-specific *Brassica napus* napin gene promoter that is not transcribed in the nucleus of leaf cells (Ellerstrom et al., 1996). The native *Brassica* PPR10 protein (Bn-PPR10) stabilizes and facilitates translation of the atpH mRNA. However, Bn-PPR10 RNA binding protein does not recognize $PBS^{ZmGG}$, the mutant maize PPR10 binding site because the 23-nucleotide *Brassica* binding site differs by 2 nucleotides from the wild-type maize PPR10 binding site and by 4 nucleotides from the mutant maize binding site.

```
Zm-PPR10 wt Binding site:
                               (SEQ ID NO: 259)
ATTGTATCcTTAACcATTTCTTT Bn-PPR10 wt Binding site:
                               (SEQ ID NO: 260)
ATTGTATCATTAACTATTTCTTT Zm-PPR10^GG mut Binding site:
                               (SEQ ID NO: 261)
ATTGTAggcTTAACcATTTCTTT
```

In the *Brassica* ssp. seed (embryo) cell, the napin seed storage protein gene promoter is turned on, the mRNA is translated in the cytoplasm and the $PPR10^{GG}$ protein is imported into chloroplasts where it binds to its cognate binding site upstream of the gfp AUG translation initiation codon. Binding of the $Zm-PPR10^{GG}$ stabilizes the gfp mRNA and facilitates its translation. The result is high-level GFP protein accumulation in the plastids of embryo cells in oilseed crops.

Figure 12A:
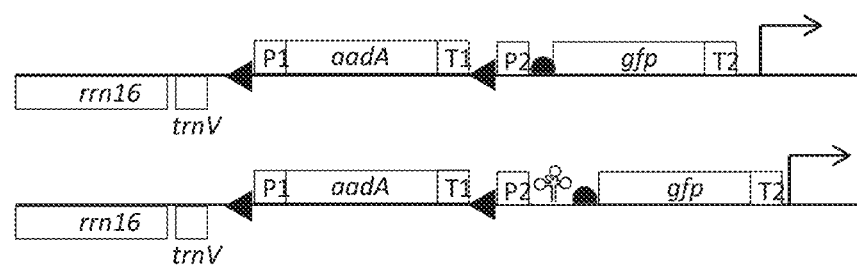
FIGS. 12A-12B. Transgenes for seed-specific expression in *Brassica* spp.

To construct the regulated plastid transgenes, the tobacco Prrn promoter is linked up with the 100 nt sequence directly upstream of the maize atpH gene. The two sequences together constitute the 5' regulatory region driving GFP expression. The gfp coding region is followed by the rbcL gene terminator (TrbcL). Prrn-PPR10GG-GFP-TrbcL corresponds to SEQ ID NO. 262. The transgene is cloned adjacent to an aadA gene in the *B. napus*-specific plastid transformation vector shown in FIG. 12A. Also shown in FIG. 12A is a variant, where a T-RNA (symbolized with a cloverleaf; SEQ ID NO. 263) is cloned between the promoter and the 100 nt maize sequence. The tRNA is efficiently processed to create a processed end that is more sensitive to degradation in the absence of the protecting Zm-PPR10GG protein, reducing background in the absence of the $PPR10^{GG}$ protein. This construct can be engineered to express a protein of interest in the place of GFP, or a protein of interest can be operably linked to GFP via cleavable protein linker.

Figure 12B:
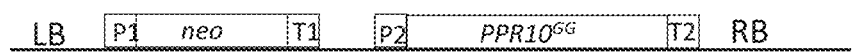

Likewise, a *Brassica napus* seed-specific PnpaA:$PPR10^{GG}$:Tocs nuclear transgene can be cloned into a pCAMBIA2300 *Agrobacterium* binary vector with a plant-selectable kanamycin resistance gene for transformation of the *B. napus* nucleus (FIG. 12B). The modified *Zea mays* PPR10 gene sequence that results in selective recognition of the modified GG RNA binding site is described (Barkan et al., 2012) (SEQ ID NO: 265). For reference, the wild-type maize PPR10 sequence is also listed (SEQ ID NO: 264). The PPR10 protein is naturally targeted to chloroplasts, thus it requires only a tissue-specific promoter and a eukaryotic transcription terminator, such as octopine synthase 3' UTR (Tocs) (GenBank accession no. AJ311872.1). The napin gene is encoded in a small gene family. A suitable promoter for the PnpaA:$PPR10^{GG}$:Tocs gene was characterized experimentally (Ellerstrom et al., 1996) (GenBank accession J02798), and additional *B. napus* promoters are available (Sohrabi et al., 2015). The promoter of a legume storage protein gene, phaseolin, (SEQ ID NO: 266) is known to be very efficient for the expression of recombinant proteins in *Arabidopsis thaliana* (De Jaegert et al., 2002). The promoter sequence is available in US patent application 2003/0159183.

```
>Prrn-PPR10GG-GFP-TrbcL
                                                              SEQ ID NO: 262
>GagctcGCTCCCCCGCCGTCGTTCAATGAGAATGGATAAGAGGCTCGTGGGATTGAC

GTGAGGGGGCAGGGATGGCTATATTTCTGGGAGTTACTTCTACCCGATAGAGCTTAG

AAGTTGGAAGTAATAATTTCTTGGTTGATTGTAGGCTTAACCATTTCTTTTTTTTGA

CACGAGGAACTCATCATGgctagcAGTAAAGGAGAAGAACTTTTCACTGGAGTTGTCCC

AATTCTTGTTGAATTAGATGGTGATGTTAATGGGCACAAATTTTCTGTCAGTGGAGA

GGGTGAAGGTGATGCAACATACGGAAAACTTACCCTTAAATTTATTTGCACTACTGG

AAAACTACCTGTTCCtTGGCCAACACTTGTCACTACTTTCTCTTATGGTGTTCAATGCT

TTTCAAGATACCCAGATCATATGAAGCGGCACGACTTCTTCAAGAGCGCCATGCCTG

AGGGATACGTGCAGGAGAGGACCATCTCTTTCAAGGACGACGGGAACTACAAGACA

CGTGCTGAAGTCAAGTTTGAGGGAGACACCCTCGTCAACAGGATCGAGCTTAAGGG

AATCGATTTCAAGGAGGACGGAAACATCCTCGGCCACAAGTTGGAATACAACTACA

ACTCCCACAACGTATACATCACGGCAGACAAACAAAAGAATGGAATCAAAGCTAAC

TTCAAAATTAGACACAACATTGAAGATGGAAGCGTTCAACTAGCAGACCATTATCA
```

-continued

ACAAAATACTCCAATTGGCGATGGCCCTGTCCTTTTACCAGACAACCATTACCTGTC

CACACAATCTGCCCTTTCGAAAGATCCCAACGAAAAGAGAGACCACATGGTCCTTCT

TGAGTTTGTAACAGCTGCTGGGATTACACATGGCATGGATGAACTgTACAAATAAAtc tagaAAACAGTAGACATTAGCAGATAAATTAGCAGGAAATAAAGAAGGATAAGGAGA

AAGAACTCAAGTAATTATCCTTCGTTCTCTTAATTGAATTGCAATTAAACTCGGCCC

AATCTTTTACTAAAAGGATTGAGCCGAATACAACAAAGATTCTATTGCATATATTTT

GACTAAGTATATACTTACCTAGATATACAAGATTTGAAATACAAAATCTAaagat

>tRNA (trnP, 147 bp) SEQ ID NO: 263

(SEQ ID NO: 263)

AAGTCTTTACAATGACAATGGAAACCGATGTAAAGGGATGTAGCGCAGCTTGGTAG

CGCGTTTGTTTTGGGTACAAAATGTCACAGGTTCAAATCCTGTCATCCCTATCCCTAA

CTtGTAGTTATCGTATCAGCAGTAACAATAGAT

>Zm_PPR10 WT

SEQ ID NO: 264

ATGGAGGCCACCGGCAGGGGCTGTTCCCGAACAAGCCCACCCTCCCGGCGGGGCC

GAGGAAACGGGGCCCGCTCCTCCCGGCCGCGCCCCCGCCACCGTCCCCCTCCTCGCT

CCCGCTCGACTCGCTCCTGCTCCACCTCACCGCGCCCGCCCCCGCGCCGGCCCCCGC

GCCGCGGCGGTCGCACCAGACGCCGACGCCGCCGCACTCCTTCCTCTCCCCCGACGC

GCAGGTGCTGGTGCTCGCCATCTCCTCGCACCCGCTCCCCACGCTGGCGGCCTTCCT

GGCCTCCCGCCGCGACGAGCTCCTCCGCGCGGACATCACGTCCCTGCTCAAGGCGCT

GGAGCTCTCGGGGCACTGGGAGTGGGCGCTCGCGCTCCTCCGGTGGGCAGGCAAGG

AGGGTGCCGCCGACGCGTCGGCGCTCGAGATGGTCGTCCGCGCGCTGGGCCGCGAG

GGCCAGCACGACGCCGTCTGCGCGCTGCTCGACGAAACGCCGCTCCCGCCGGGCTC

CCGCCTCGACGTCCGCGCCTACACCACCGTGCTGCACGCGCTCTCCCGCGCGGGCCG

GTACGAGCGCGCGCTCGAGCTCTTCGCCGAGCTCCGGCGCCAGGGGTGGCGCCCA

CGCTCGTCACCTACAACGTCGTGCTGGACGTGTACGGGCGGATGGGCCGGTCGTGG

CCGCGGATCGTCGCCCTCCTCGATGAGATGCGCGCCGCCGGGGTCGAGCCCGACGG

CTTCACCGCCAGCACGGTGATCGCCGCGTGCTGCCGCGACGGGCTGGTTGACGAGG

CGGTGGCGTTCTTCGAGGACCTCAAGGCCCGCGGCCACGCCCCGTGCGTCGTCACGT

ACaacGCGTTGCTCCAGGTGTTCGGCAAGGCCGGGAACTACACGGAGGCGCTGCGCG

TGCTCGGGGAGATGGAGCAGAACGGCTGCCAGCCAGATGCTGTGACGTACaacGAGC

TCGCCGGAACGTACGCCCGGGCTGGGTTCTTCGAGGAGGCTGCCAGGTGCCTGGAC

ACAATGGCATCCAAGGGTCTGTTGCCAAACGCATTCACGTACAACACCGTGATGAC

AGCCTATGGGAATGTTGGGAAGGTGGATGAGGCGCTCGCTCTGTTTGACCAGATGA

AGAAGACCGGGTTCGTGCCGAACGTGAACACGTACAATCTTGTCCTTGGCATGCTTG

GCAAGAAGTCAAGGTTCACGGTGATGCTAGAGATGCTTGGAGAGATGTCGAGGAGC

GGATGCACACCGAACCGGGTAACATGAACACAATGCTTGCAGTCTGTGGGAAGCG

TGGCATGGAGGACTACGTCACCCGGGTTCTGGAGGGGATGAGGTCTTGCGGGGTTG

AACTGAGCCGAGACACCTACAACACCCTGATAGCTGCGTACGGCCGGTGTGGCTCG

AGGACTAATGCCTTCAAGATGTACAACGAGATGACCAGCGCTGGATTCACCCCCTG

CATCACCACGTACAACGCGTTGCTGAACGTGCTGTCGCGGCAGGGCGACTGGTCCA

CCGCCCAGTCGATCGTAAGCAAAATGAGGACCAAGGGGTTCAAGCCGAACGAGCAG

TCGTATTCGCTGCTGCTCCAGTGCTACGCGAAGGGGGGCAACGTGGCAGGGATAGC

```
CGCGATCGAGAACGAGGTGTACGGATCAGGTGCCGTTTTCCCAAGCTGGGTGATCCT

GAGGACCCTTGTCATCGCCAATTTCAAGTGCCGGCGACTGGATGGCATGGAGACGG

CGTTTCAAGAGGTGAAGGCCAGAGGCTACAACCCGGACCTCGTGATATTCAACTCC

ATGCTGTCCATCTACGCGAAGAACGGGATGTACAGCAAGGCCACCGAGGTCTTCGA

CTCCATCAAGCGGAGCGGGCTGAGCCCCGACCTCATCACCTACAACAGCCTGATGG

ACATGTACGCCAAGTGCAGCGAGTCGTGGGAGGCCGAGAAGATACTGAACCAGCTC

AAGTGCTCCCAGACGATGAAGCCCGACGTGGTGTCCTACAACACGGTCATAAACGG

GTTCTGCAAGCAGGGGCTGGTGAAAGAGGCCCAGAGGGTCCTCTCGGAGATGGTCG

CCGACGGCATGGCCCCCTGCGCCGTGACCTACCACACGCTCGTCGGGGGTTACTCCA

GCCTGGAGATGTTCAGCGAGGCCAGGGAGGTCATCGGCTACATGGTCCAGCACGGC

CTCAAGCCTATGGAGCTGACCTACAGGAGAGTCGTCGAGAGCTACTGCAGAGCGAA

GCGGTTCGAGGAGGCTCGCGGCTTCCTGTCCGAGGTCTCGGAGACCGACCTGGATTT

TGACAAGAAGGCGCTCGAAGCCTATATAGAGGATGCGCAGTTTGGAAGGTAG

>Zm_PPR10 GG                                                         SEQ ID NO: 265

ATGGAGGCCACCGGCAGGGGGCTGTTCCCGAACAAGCCCACCCTCCCGGCGGGGCC

GAGGAAACGGGGCCCGCTCCTCCCGGCCGCGCCCCCGCCACCGTCCCCCTCCTCGCT

CCCGCTCGACTCGCTCCTGCTCCACCTCACCGCGCCCGCCCCCGCGCCGGCCCCCGC

GCCGCGGCGGTCGCACCAGACGCCGACGCCGCCGCACTCCTTCCTCTCCCCCGACGC

GCAGGTGCTGGTGCTCGCCATCTCCTCGCACCCGCTCCCCACGCTGGCGGCCTTCCT

GGCCTCCCGCCGCGACGAGCTCCTCCGCGCGGACATCACGTCCCTGCTCAAGGCGCT

GGAGCTCTCGGGGCACTGGGAGTGGGCGCTCGCGCTCCTCCGGTGGGCAGGCAAGG

AGGGTGCCGCCGACGCGTCGGCGCTCGAGATGGTCGTCCGCGCGCTGGGCCGCGAG

GGCCAGCACGACGCCGTCTGCGCGCTGCTCGACGAAACGCCGCTCCCGCCGGGCTC

CCGCCTCGACGTCCGCGCCTACACCACCGTGCTGCACGCGCTCTCCCGCGCGGGCCG

GTACGAGCGCGCGCTCGAGCTCTTCGCCGAGCTCCGGCGCCAGGGGTGGCGCCCA

CGCTCGTCACCTACAACGTCGTGCTGGACGTGTACGGGCGGATGGGCCGGTCGTGG

CCGCGGATCGTCGCCCTCCTCGATGAGATGCGCGCCGCCGGGGTCGAGCCCGACGG

CTTCACCGCCAGCACGGTGATCGCCGCGTGCTGCCGCGACGGGCTGGTTGACGAGG

CGGTGGCGTTCTTCGAGGACCTCAAGGCCCGCGGCCACGCCCCGTGCGTCGTCACGT

ACacaGCGTTGCTCCAGGTGTTCGGCAAGGCCGGGAACTACACGGAGGCGCTGCGCG

TGCTCGGGGAGATGGAGCAGAACGGCTGCCAGCCAGATGCTGTGACGTACaccGAGC

TCGCCGGAACGTACGCCCGGGCTGGGTTCTTCGAGGAGGCTGCCAGGTGCCTGGAC

ACAATGGCATCCAAGGGTCTGTTGCCAAACGCATTCACGTACAACACCGTGATGAC

AGCCTATGGGAATGTTGGGAAGGTGGATGAGGCGCTCGCTCTGTTTGACCAGATGA

AGAAGACCGGGTTCGTGCCGAACGTGAACACGTACAATCTTGTCCTTGGCATGCTTG

GCAAGAAGTCAAGGTTCACGGTGATGCTAGAGATGCTTGGAGAGATGTCGAGGAGC

GGATGCACACCGAACCGGGTAACATGGAACACAATGCTTGCAGTCTGTGGGAAGCG

TGGCATGGAGGACTACGTCACCCGGGTTCTGGAGGGGATGAGGTCTTGCGGGGTTG

AACTGAGCCGAGACACCTACAACACCCTGATAGCTGCGTACGGCCGGTGTGGCTCG

AGGACTAATGCCTTCAAGATGTACAACGAGATGACCAGCGCTGGATTCACCCCCTG
```

-continued
```
CATCACCACGTACAACGCGTTGCTGAACGTGCTGTCGCGGCAGGGCGACTGGTCCA

CCGCCCAGTCGATCGTAAGCAAAATGAGGACCAAGGGGTTCAAGCCGAACGAGCAG

TCGTATTCGCTGCTGCTCCAGTGCTACGCGAAGGGGGGCAACGTGGCAGGGATAGC

CGCGATCGAGAACGAGGTGTACGGATCAGGTGCCGTTTTCCCAAGCTGGGTGATCCT

GAGGACCCTTGTCATCGCCAATTTCAAGTGCCGGCGACTGGATGGCATGGAGACGG

CGTTTCAAGAGGTGAAGGCCAGAGGCTACAACCCGGACCTCGTGATATTCAACTCC

ATGCTGTCCATCTACGCGAAGAACGGGATGTACAGCAAGGCCACCGAGGTCTTCGA

CTCCATCAAGCGGAGCGGGCTGAGCCCCGACCTCATCACCTACAACAGCCTGATGG

ACATGTACGCCAAGTGCAGCGAGTCGTGGGAGGCCGAGAAGATACTGAACCAGCTC

AAGTGCTCCCAGACGATGAAGCCCGACGTGGTGTCCTACAACACGGTCATAAACGG

GTTCTGCAAGCAGGGGCTGGTGAAAGAGGCCCAGAGGGTCCTCTCGGAGATGGTCG

CCGACGGCATGGCCCCCTGCGCCGTGACCTACCACACGCTCGTCGGGGGTTACTCCA

GCCTGGAGATGTTCAGCGAGGCCAGGGAGGTCATCGGCTACATGGTCCAGCACGGC

CTCAAGCCTATGGAGCTGACCTACAGGAGAGTCGTCGAGAGCTACTGCAGAGCGAA

GCGGTTCGAGGAGGCTCGCGGCTTCCTGTCCGAGGTCTCGGAGACCGACCTGGATTT

TGACAAGAAGGCGCTCGAAGCCTATATAGAGGATGCGCAGTTTGGAAGGTAG
```

Phaseolin promoter

SEQ ID NO: 266

```
ggtcgacggtatcgataagcttgatatcgaattcctgcagcccaattcattgtactcccagtatcattatagtgaaagttttggctctctcgccgg tggtttttaccctctatttaaagggggttttccacctaaaaattctggtatcattctcactttacttgttactttaatttctcataatctttggttgaaattatc acgcttccgcacacgatatccctacaaatttattatttgttaaacattttcaaaccgcataaaattttatgaagtcccgtctatctttaatgtagtctaa cattttcatattgaaatatataatttacttaattttagcgttggtagaaagcataatgatttattcttattcttcttcatataaatgtttaatatacaat ataaacaaattctttaccttaagaaggatttcccattttatattttaaaaatatatttatcaaatattttttcaaccacgtaaatctcataataataagttgt ttcaaaagtaataaaatttaactccataattttttattcgactgatcttaaagcaacacccagtgacacaactagccatttttttctttggataaaaa aatccaattatcattgtatttttttatacaatgaaaatttcaccaaacaatcatttgtggtatttctgaagcaagtcatgttatgcaaaattctataatt cccatttgacactacggaagtaactgaagatctgcttttacatgcgagacacatcttctaaagtaattttaataatagttactatattcaagatttca tatatcaaatactcaatattacttctaaaaaattaattagatataattaaaatattacttttttaattttaagtttaattgttgaatttgtgactattgattt attattctactatgtttaaattgttttatagatagtttaaagtaaatataagtaatgtagtagagtgttagagtgttaccctaaaccataaactataacattt atggtggactaattttcatatatttcttattgcttttaccttttcttggtatgtaagtccgtaactagaattactgtgggttgccatggcactctgtggtc ttttggttcatgcatggatgcttgcgcaagaaaaagacaaagaacaaagaaaaaagacaaaacagagagacaaaacgcaatcacacaacc aactcaaattagtcactggctgatcaagatcgccgcgtccatgtatgtctaaatgccatgcaaagcaacacgtgcttaacatgcactttaaatg gctcacccatctcaacccacacacaaacacattgccttttcttcatcatcaccacaaccacctgtatatattcattctcttccgccacctcaatttc ttcacttcaacacacgtcaacctgca
```

The *Arabidopsis* nuclear genome encodes >400 Pentatricopeptide Repeat Proteins (PPRs), of which PPR10 is a member (Barkan and Small, 2014). Other P-type proteins that function similar to PPR10 are the *Arabidopsis* HCF152 and PGR3 proteins which is required for the accumulation of transcripts cleaved in the psbH-petB intergenic region and petL operon, respectively (Meierhoff et al., 2003; Yamazaki et al., 2004). *Zea* maize CRP1 is involved in the processing and translation of the chloroplast petD and petA RNAs (Fisk et al., 1999). HCF107, a member in the half-a-tetratricopeptide (HAT) family, also defines the processed end of psbH and enhance its translation by remodeling its 5' UTR (Hammani et al., 2012). These proteins with their cognate binding site can be engineered to test and establish similar chloroplast transgene regulation system as PPR10.

Targeted Mutagenesis of *Brassica napus* ACC2 Genes to Obtain Spectinomycin Hypersensitive Plants Chloroplast genome engineering in crops enables many applications, including improvement of photosynthetic efficiency, incorporation of novel metabolic pathways and delivery of vaccines in veterinary applications. This platform technology is absent in oilseed rape (*Brassica napus* or canola) due to its tolerance to spectinomycin, the selective agent used to obtain plants with transformed chloroplast genomes. We delete the ACC2 gene copies in the nuclear genome of oilseed rape to obtain spectinomycin hypersensitive, chloroplast transformation competent lines.

Figure 13:
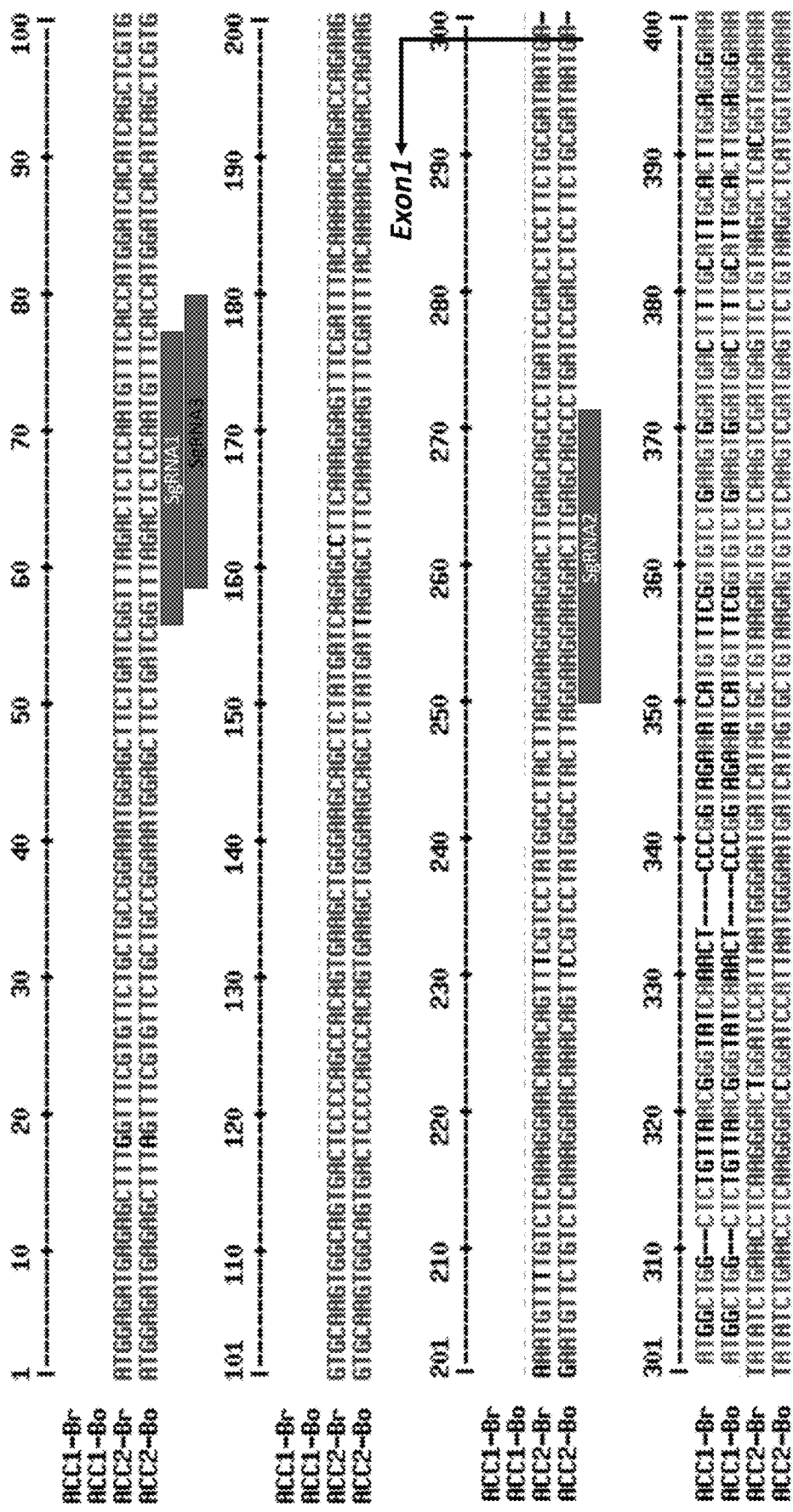
FIG. 13. Alignment of the N-terminal nucleotides of *Brassica napus* cv Darmor-bzh ACC2-Br: BnaA06g04070D (SEQ ID NO: 345); ACC2-Bo: BnaC06g01580D (SEQ ID NO: 346); ACC1-Br: BnaA08g06180D (SEQ ID NO: 347); ACC1-Bo: BnaC08g06560D (SEQ ID NO: 348). SgRNA1-3 as shown are provided as SEQ ID NOs: 349-351, respectively.

*Brassica napus* is a recent amphiploid hybrid of *Brassica rapa* and *Brassica oleracea*, and therefore carries at least one copy of each gene from the parental species. Because the common ancestor of the parental species underwent a genome triplication, this number may be as high as six. The *B. napus* cv Darmor-bzh darft genome available at the Genoscope website has only a single annotated ACC2 gene copy for each of the parental genomes: the *Brassica rapa*-like ACC2-Br BnaA06g04070D gene encoded in chromosome A6 and the *Brassica oleracea*-like ACC2-Bo BnaC06g01580D on chromosome C6. If multiple ACC2 gene copies are present, we hypothesized that over evolutionary time single nucleotide polymorphic mutations must have accumulated unique to each gene. To obtain information about the actual number of ACC2 gene copies and facilitate the design of gRNAs that simultaneously target each nuclear ACC2 gene copies, we cloned and sequenced PCR products of the N-terminal regions. Analyses of the data indicates that there are at least three *B. rapa*-like copies and two *B. oleracea*-like copies present in the *B. napus* cv. Westar nuclear genome. Inspection of the N-terminal extension lead to the identification of 28 potential sgRNAs with a GGN PAM sequence (Table 4). SgRNA3 was selected to target a single site and sgRNA1 and sgRNA2 to target two sites in the ACC2 N-terminal extension (FIG. 13). The benefit of targeting two sites is a deletion of DNA segment between the two sites, that may be used for tracking the mutant alleles by PCR.

TABLE 4

| Target | Genomic Sequence (5'-3') | Strand | Forward Oligo | Reverse Oligo |
|---|---|---|---|---|
| sgRNA1 | ggtttagactctccaatgtttc (SEQ ID NO: 267) | ± | GATTGctttgtaacctctcagatt (SEQ ID NO: 268) | AAACaatctgagaggttacaaagC (SEQ ID NO: 269) |
| sgRNA2 | ggaaggaaggacttgagcagcc (SEQ ID NO: 270) | ± | GATTGccgacgagttcaggaagga (SEQ ID NO: 271) | AAACtccttcctgaactcgtcggC (SEQ ID NO: 272) |
| sgRNA3 | ggtgaaacattggagagtctaa (SEQ ID NO: 273) | − | GATTGaatctgagaggttacaaag (SEQ ID NO: 274) | AAACctttgtaacctctcagattC (SEQ ID NO: 275) |
| 4 | ggagcttctgatcggtttagac (SEQ ID NO: 276) | ± | | |
| 5 | ggtgcaagtggcagtgactccc (SEQ ID NO: 277) | ± | | |
| 6 | gacaccgacccctcagtgacgg (SEQ ID NO: 278) | ± | | |
| 7 | ggagtttcgatttacaaaaaca (SEQ ID NO: 279) | ± | | |
| 8 | ggcctacttaggaaggaaggac (SEQ ID NO: 280) | ± | | |
| 9 | ggaaggacttgagcagccctga (SEQ ID NO: 281) | ± | | |
| 10 | gtcctatggcctacttaggaagg (SEQ ID NO: 282) | ± | | |
| 11 | ggacttgagcagccctgatccg (SEQ ID NO: 283) | ± | | |
| 12 | atggcctacttaggaaggaagg (SEQ ID NO: 284) | ± | | |
| 13 | cgacctccttctgcgataatgg (SEQ ID NO: 285) | ± | | |
| 14 | ggagagtctaaaccgatcagaa (SEQ ID NO: 286) | − | | |
| 15 | ggagtcactgccacttgcacca (SEQ ID NO: 287) | − | | |
| 16 | ggggagtcactgccacttgcacc (SEQ ID NO: 288) | − | | |
| 17 | ggctggggagtcactgccacttg (SEQ ID NO: 289) | − | | |
| 18 | ggtcttgtttttgtaaatcgaa (SEQ ID NO: 290) | − | | |
| 19 | tccttcctaagtaggccatagg (SEQ ID NO: 291) | − | | |
| 20 | aagtccttccttcctaagtagg (SEQ ID NO: 292) | − | | |

TABLE 4-continued

| Target | Genomic Sequence (5'-3') | Strand | Forward Oligo | Reverse Oligo |
|---|---|---|---|---|
| 21 | ggctgctcaagtccttccttcc (SEQ ID NO: 293) | − | | |
| 22 | gcagaaggaggtcggatcaggg (SEQ ID NO: 294) | − | | |
| 23 | gggctgctcaagtccttccttc (SEQ ID NO: 295) | − | | |
| 24 | cgcagaaggaggtcggatcagg (SEQ ID NO: 296) | − | | |
| 25 | cattatcgcagaaggaggtcgg (SEQ ID NO: 297) | − | | |
| 26 | ggtcggatcagggctgctcaag (SEQ ID NO: 298) | − | | |
| 27 | ggaggtcggatcagggctgctc (SEQ ID NO: 299) | − | | |
| 28 | agcaaaccattatcgcagaagg (SEQ ID NO: 300) | − | | |

Figure 14B:
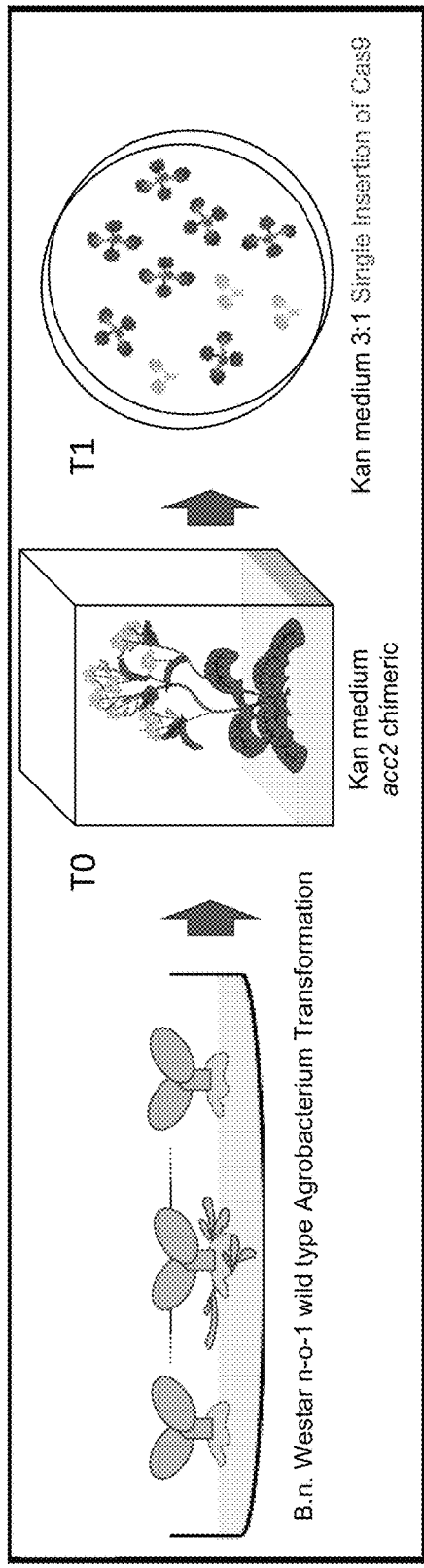
Figure 14C:
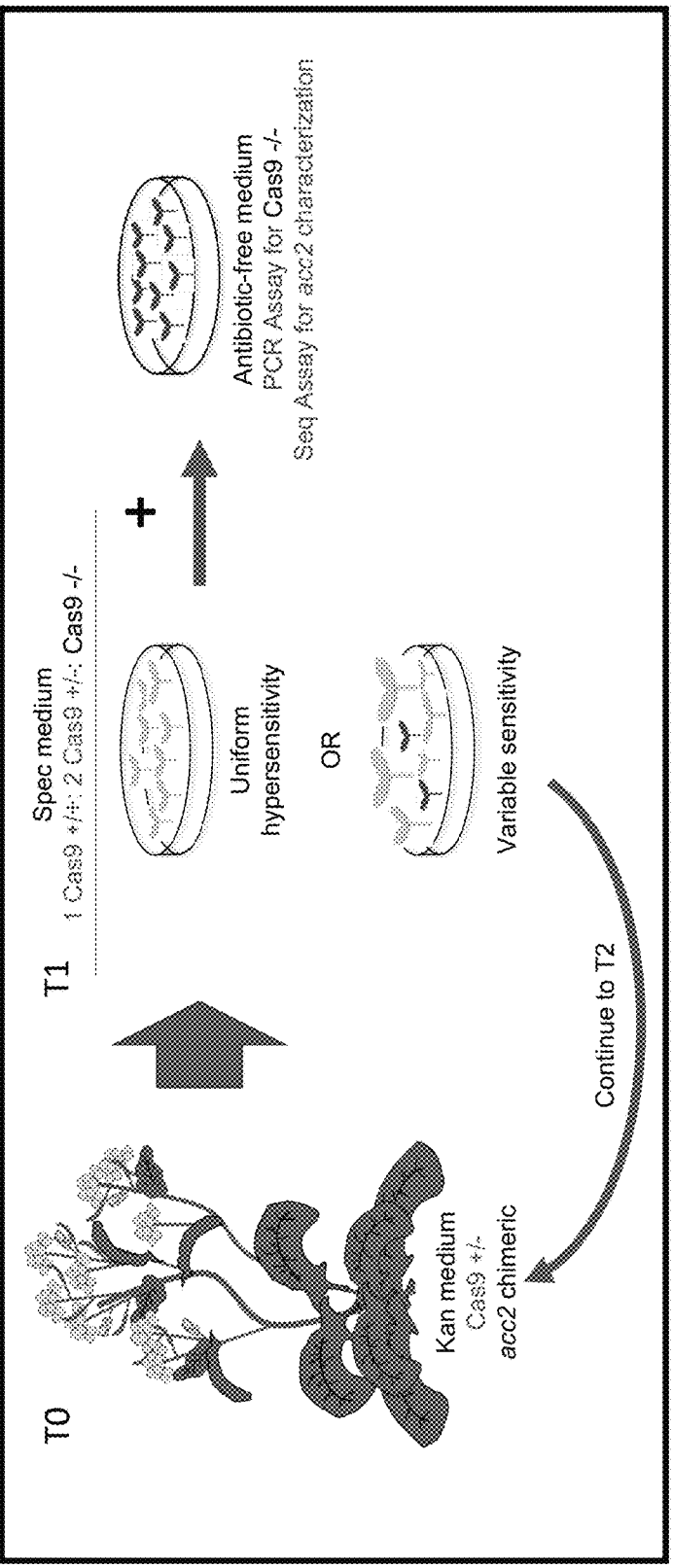

CRSPR/Cas9-mediated gene ACC2 gene editing in *Brassica napus* is carried out using the vector system developed in the Jiang-Kang Zhu laboratory (Mao et al., 2013; Liu et al., 2015). Single-stranded oligonucleotides were designed to fit the BbsI-digested p998/psgR-cas9-At vector, a pCAMBIA2300 vector derivative (Table 4). To accommodate the *Arabidopsis* U6 promoter, a G nucleotide was added at the end opposite to the PAM sequence. *Agrobacterium* vectors carrying two sgRNAs were obtained following the detailed protocol of Liu et al. (2015). *Agrobacterium* vectors carrying the sgRNAs were then introduced into *Agrobacterium* strain EHA105 or GV3101, and transformed into *B. napus* cotyledons following the protocol of Bates at all. (Bates et al., 2017). Progress in losing ACC2 activity is tracked by the absence of leaf formation on germinating seedlings. A tolerant *B. napus* seedling with well-developed leaves is shown in FIG. 14A. FIGS. 14B and 14C show a flowchart to obtain Cas9-free spectinomycin hypersensitive acc2 *Brassica napus*. (14B) Selection of CRISPR/Cas9 transgenic plants by kanamycin resistance. (14C) Hypersensitivity bioassay identifies T1 families with putative knockouts in all ACC2 copies, leading to the isolation of Cas9-free acc2 individuals. In certain instances, hypersensitivity will be uniform in the plant. Non-uniform hypersensitivity to spectinomycin will prompt an additional cycle of screening in the next seed generation.

REFERENCES

Babiychuk E, Vandepoele K, Wissing J, Garcia-Diaz M, De Rycke R, Akbari H, Joubes J, Beeckman T, Jansch L, Frentzen M, Van Montagu M C, Kushnir S (2011) Plastid gene expression and plant development require a plastidic protein of the mitochondrial transcription termination factor family. Proc Natl Acad Sci USA 108: 6674-6679

Barkan A, Rojas M, Fujii S, Yap A, Chong Y S, Bond C S, Small I (2012) A Combinatorial Amino Acid Code for RNA Recognition by Pentatricopeptide Repeat Proteins. PLOS Genetics 8

Barkan A, Small I (2014) Pentatricopeptide repeat proteins in plants. Annu Rev Plant Biol 65: 415-442

Belhaj K, Chaparro-Garcia A, Kamoun S, Nekrasov V (2013) Plant genome editing made easy: targeted mutagenesis in model and crop plants using the CRISPR/Cas system. Plant Methods 9: 39

Bock R (2015) Engineering Plastid Genomes: Methods, Tools, and Applications in Basic Research and Biotechnology. Annu Rev Plant Biol 66: 211-241

Brooks C, Nekrasov V, Lippman Z B, Van Eck J (2014) Efficient gene editing in tomato in the first generation using the clustered regularly interspaced short palindromic repeats/CRISPR-associated9 system. Plant Physiol 166: 1292-1297

Carrer H, Staub J M, Maliga P (1991) Gentamycin resistance in *Nicotiana* conferred by AAC(3)-I, a narrow substrate specificity acetyl transferase. Plant Mol Biol 17: 301-303

Carrillo N, Seyer P, Tyagi A, Herrmann R G (1986) Cytochrome b-559 genes from *Oenothera hookeri* and *Nicotiana tabacum* show a remarkably high degree of conservation as compared to spinach. The enigma of cytochrome b-559: highly conserved genes and proteins but no known function. Curr Genet 10: 619-624

Chakrabarti S K, Lutz K A, Lertwirijawong B, Svab Z, Maliga P (2006) Expression of the cry9Aa2 B. t. gene in the tobacco chlroplasts confers resistance to potato tuber moth. Transgenic Res 15: 481-488

Cheng L, Li H P, Qu B, Huang T, Tu J X, Fu T D, Liao Y C (2010) Chloroplast transformation of rapeseed (*Brassica napus*) by particle bombardment of cotyledons. Plant Cell Rep 29: 371-381

Chupeau M C, Granier F, Pichon O, Renou J P, Gaudin V, Chupeau Y (2013) Characterization of the early events leading to totipotency in an *Arabidopsis* protoplast liquid culture by temporal transcript profiling. Plant Cell 25: 2444-2463

Clough S J, Bent A F (1998) Floral dip: a simplified method for *Agrobacterium*-mediated transformation of *Arabidopsis thaliana*. Plant J 16: 735-743

Corpet F (1988) Multiple sequence alignment with hierarchical clustering. Nucleic Acids Res 16: 10881-10890

De Jaegert G, Scheffer S, Jacobs A, Zambre M, Zobell O, Goossens A, Depicker A, Angenon G (2002) Boosting heterologous protein production in transgenic dicotyledonous seeds using *Phaseolis vulgaris* regulatory asequences. Nat Biotechnol 20: 1265-1268

Dufourmantel N, Dubald M, Matringe M, Canard H, Garcon F, Job C, Kay E, Wisniewski J P, Ferullo J M, Pelissier B, Sailland A, Tissot G (2007) Generation and characterization of soybean and marker-free tobacco plastid transformants over-expressing a bacterial 4-hydroxyphenylpyruvate dioxygenase which provides strong herbicide tolerance. Plant Biotechnol J 5: 118-133

Dufourmantel N, Pelissier B, Garcon F, Peltier G, Ferullo J M, Tissot G (2004) Generation of fertile transplastomic soybean. Plant Mol Biol 55: 479-489

Ellerstrom M, Stalberg K, Ezcurra I, Rask L (1996) Functional dissection of a napin gene promoter: Identification of promoter elements required for embryo and endosperm-specific transcription. Plant Mol Biol 32: 1019-1027

Feng Z, Mao Y, Xu N, Zhang B, Wei P, Yang D L, Wang Z, Zhang Z, Zheng R, Yang L, Zeng L, Liu X, Zhu J K (2014) Multigeneration analysis reveals the inheritance, specificity, and patterns of CRISPR/Cas-induced gene modifications in *Arabidopsis*. Proc Natl Acad Sci USA 111: 4632-4637

Fisk D G, Walker M B, Barkan A (1999) Molecular cloning of the maize gene crp1 reveals similarity between regulators of mitochondrial and chloroplast gene expression. EMBO J 18: 2621-2630

Gimpel J A, Nour-Eldin H H, Scranton M A, Li D, Mayfield S P (2016) Refactoring the Six-Gene Photosystem II Core in the Chloroplast of the Green Algae *Chlamydomonas reinhardtii*. ACS Synth Biol 5: 589-596

Hammani K, Cook W B, Barkan A (2012) RNA binding and RNA remodeling activities of the half-a-tetratricopeptide (HAT) protein HCF107 underlie its effects on gene expression. Proc Natl Acad Sci USA 109: 5651-5656

Hanson M R, Lin M T, Carmo-Silva A E, Parry M A (2016) Towards engineering carboxysomes into C3 plants. Plant J 87: 38-50

Hou B K, Zhou Y H, Wan L H, Zhang Z L, Shen G F, Chen Z H, Hu Z M (2003) Chloroplast transformation in oilseed rape. Transgenic Res 12: 111-114

Howell E C, Kearsey M J, Jones G H, King G J, Armstrong S J (2008) A and C genome distinction and chromosome identification in *Brassica napus* by sequential fluorescence in situ hybridization and genomic in situ hybridization. Genetics 180: 1849-1857

Kanamoto H, Yamashita A, Asao H, Okumura S, Takase H, Hattori M, Yokota A, Tomizawa K (2006) Efficient and stable transformation of *Lactuca sativa* L. cv. Cisco (lettuce) plastids. Transgenic Res 15: 205-217

Koornneef M, Meinke D (2010) The development of *Arabidopsis* as a model plant. Plant J 61: 909-921

Kuroda H, Maliga P (2001) Complementarity of the 16S rRNA penultimate stem with sequences downstream of the AUG destabilizes the plastid mRNAs. Nucleic Acids Res 29: 970-975

Kuroda H, Maliga P (2001) Sequences downstream of the translation initiation codon are important determinants of translation efficiency in chloroplasts. Plant Physiol 125: 430-436

Li J F, Zhang D, Sheen J (2014) Cas9-based genome editing in *Arabidopsis* and tobacco. Methods Enzymol 546: 459-472

Liu C W, Lin C C, Chen J J, Tseng M J (2007) Stable chloroplast transformation in cabbage (*Brassica oleracea* L. var. *capitata* L.) by particle bombardment. Plant Cell Rep 26: 1733-1744

Liu C W, Lin C C, Yiu J C, Chen J J, Tseng M J (2008) Expression of a *Bacillus thuringiensis* toxin (crylAb) gene in cabbage (*Brassica oleracea* L. var. *capitata* L.) chloroplasts confers high insecticidal efficacy against *Plutella xylostella*. Theor Appl Genet 117: 75-88

Liu F, Cao M, Yao L, Li Y, Robaglia C, Tourneur C (1998) In planta transformation of pakchoi (*Brassica campestris* 1. ssp. *chinensis*) by infiltration of adult plants with *Agrobacterium*. Acta Horticult 467: 187

Liu X, Brost J, Hutcheon C, Guilfoil R, Wilson A K, Leung S, Shewmaker C K, Rooke S, Nguyen T, Kiser J, De Rocher J (2012) Transformation of the oilseed crop *Camelina sativa* by *Agrobacterium*-mediated floral dip and simple large-scale screening of transformants. In Vitro Cellular & Developmental Biology—Plant 48: 462-468

Lu C F, Kang J L (2008) Generation of transgenic plants of a potential oilseed crop *Camelina sativa* by *Agrobacterium*-mediated transformation. Plant Cell Rep 27: 273-278

Lutz K A, Azhagiri A, Maliga P (2011) Transplastomics in *Arabidopsis*: Progress towards developing an efficient method. In R P Jarvis, ed, Chloroplast research in *Arabidopsis*, Vol 774. Springer Science+Business Media, LLC, New York, pp 133-147.

Lutz K A, Knapp J E, Maliga P (2001) Expression of bar in the plastid genome confers herbicide resistance. Plant Physiol 125: 1585-1590

Lutz K A, Martin C, Khairzada S, Maliga P (2015) Steroid-inducible BABY BOOM system for development of fertile *Arabidopsis thaliana* plants after prolonged tissue culture. Plant Cell Rep 34: 1849-1856

Mali P, Esvelt K M, Church G M (2013) Cas9 as a versatile tool for engineering biology. Nat Methods 10: 957-963

Maliga P (2012) Plastid transformation in flowering plants. In R Bock, V Knoop, eds, Genomics of Chloroplasts and Mitochondria, Vol 35. Springer, pp 393-414

Maliga P, Bock R (2011) Plastid biotechnology: food, fuel and medicine for the 21st century. Plant Physiol 155: 1501-1510

Maliga P, Tungsuchat-Huang T (2014) Plastid transformation in *Nicotiana tabacum* and *Nicotiana sylvestris* by biolistic DNA delivery to leaves. In P Maliga, ed, Chloroplast Biotechnology: Methods and Protocols, Vol 1132. Springer Science+Business Media, New York, pp 147-163

Mao Y, Zhang H, Xu N, Zhang B, Gou F, Zhu J K (2013) Application of the CRISPR-Cas system for efficient genome engineering in plants. Mol Plant 6: 2008-2011

Marton L, Browse J (1991) Facile transformation of *Arabidopsis*. Plant Cell Rep 10: 235-239

Meierhoff K, Felder S, Nakamura T, Bechtold N, Schuster G (2003) HCF152, an *Arabidopsis* RNA binding pentatricopeptide repeat protein involved in the processing of chloroplast psbB-psbT-psbH-petB-petD RNAs. Plant Cell 15: 1480-1495

Meng B Y, Tanaka M, Wakasugi T, Ohme M, Shinozaki K, Sugiura M (1988) Cotranscription of the genes encoding two P700 chlorophyll a apoproteins with the gene for ribosomal protein CS14: determination of the transcriptional initiation site by in vitro capping. Curr Genet 14: 395-400

Motte H, Galuszka P, Spichal L, Tarkowski P, Plihal O, Smehilova M, Jaworek P, Vereecke D, Werbrouck S, Geelen D (2013) Phenyl-adenine, identified in a LIGHT-DEPENDENT SHORT HYPOCOTYLS4-assisted chemical screen, is a potent compound for shoot regeneration through the inhibition of CYTOKININ OXIDASE/DEHYDROGENASE activity. Plant Physiol 161: 1229-1241

Nugent G D, Coyne S, Nguyen T T, Kavanagh T A, Dix P J (2006) Nuclear and plastid transformation of *Brassica oleracea* var. *botrytis* (cauliflower) using PEG-mediated uptake into protoplasts. Plant Sci 170: 135-142

Parker N, Wang Y, Meinke D (2014) Natural variation in sensitivity to a loss of chloroplast translation in *Arabidopsis*. Plant Physiol 166: 2013-2027

Parker N, Wang Y, Meinke D (2016) Analysis of *Arabidopsis* Accessions Hypersensitive to a Loss of Chloroplast Translation. Plant Physiol 172: 1862-1875

Qing C M, Fan L, Lei Y, Bouchez D, Tourneur C, Yan L, Robaglia C (2000) Transformation of Pakchoi (*Brassica rapa* L. ssp *chinensis*) by *Agrobacterium* infiltration. Molecular Breeding 6: 67-72

Ruf S, Hermann M, Berger I J, Carrer H, Bock R (2001) Stable genetic transformation of tomato plastids: foreign protein expression in fruit. Nat Biotechnol 19: 870-875

Ruhlman T, Verma D, Samson N, Daniell H (2010) The role of heterologous chloroplast sequence elements in transgene integration and expression. Plant Physiol 152: 2088-2104

Scharff L B, Bock R (2014) Synthetic biology in plastids. Plant J 78: 783-798

Schneider A, Stelljes C, Adams C, Kirchner S, Burkhard G, Jarzombski S, Broer I, Horn P, Elsayed A, Hagl P, Leister D, Koop H U (2015) Low frequency paternal transmission of plastid genes in Brassicaceae. Transgenic Res 24: 267-277

Schottkowski M, Peters M, Zhan Y, Rifai O, Zhang Y, Zerges W (2012) Biogenic membranes of the chloroplast in *Chlamydomonas reinhardtii*. Proc Natl Acad Sci USA 109: 19286-19291

Schulte W, Topfer R, Stracke R, Schell J, Martini N (1997) Multi-functional acetyl-CoA carboxylase from *Brassica napus* is encoded by a multi-gene family: indication for plastidic localization of at least one isoform. Proc Natl Acad Sci USA 94: 3465-3470

Shao M, Blechl A, Thomson J G (2017) Small serine recombination systems ParA-MRS and CinH-RS2 perform precise excision of plastid DNA. Plant Biotechnol J 15: 1577-1589

Shao M, Kumar S, Thomson J G (2014) Precise excision of plastid DNA by the large serine recombinase Bxb1. Plant Biotechnol J 12: 322-329

Sharwood R E, Ghannoum O, Whitney S M (2016) Prospects for improving CO2 fixation in C3-crops through understanding C4-Rubisco biogenesis and catalytic diversity. Curr Opin Plant Biol 31: 135-142

Shimizu M, Goto M, Hanai M, Shimizu T, Izawa N, Kanamoto H, Tomizawa K, Yokota A, Kobayashi H (2008) Selectable tolerance to herbicides by mutated acetolactate synthase genes integrated into the chloroplast genome of tobacco. Plant Physiol 147: 1976-1983

Sikdar S R, Serino G, Chaudhuri S, Maliga P (1998) Plastid transformation in *Arabidopsis thaliana*. Plant Cell Rep 18: 20-24

Sinagawa-Garcia S R, Tungsuchat-Huang T, Paredes-Lopez O, Maliga P (2009) Next generation synthetic vectors for transformation of the plastid genome of higher plants. Plant Mol Biol 70: 487-498

Skarjinskaia M, Svab Z, Maliga P (2003) Plastid transformation in *Lesquerella fendleri*, an oilseed Brassicacea. Transgenic Res 12: 115-122

Sohrabi M, Zebarjadi A, Najaphy A, Kahrizi D (2015) Isolation and sequence analysis of napin seed specific promoter from Iranian Rapeseed (*Brassica napus* L.). Gene 563: 160-164

Song K, Osborn T C (1992) Polyphyletic Origins of *Brassica-Napus*—New Evidence Based on Organelle and Nuclear Rflp Analyses. Genome 35: 992-1001

Staub J M, Maliga P (1995) Expression of a chimeric uidA gene indicates that polycistronic mRNAs are efficiently translated in tobacco plastids. Plant J 7: 845-848

Stitt M, Lunn J, Usadel B (2010) *Arabidopsis* and primary photosynthetic metabolism—more than the icing on the cake. Plant J 61: 1067-1091

Svab Z, Hajdukiewicz P, Maliga P (1990) Stable transformation of plastids in higher plants. Proc Natl Acad Sci USA 87: 8526-8530

Svab Z, Maliga P (1993) High-frequency plastid transformation in tobacco by selection for a chimeric aadA gene. Proc Natl Acad Sci USA 90: 913-917

Tan H L, Yang X H, Zhang F X, Zheng X, Qu C M, Mu J Y, Fu F Y, Li J A, Guan R Z, Zhang H S, Wang G D, Zuo J R (2011) Enhanced Seed Oil Production in Canola by Conditional Expression of *Brassica napus* LEAFY COTYLEDON1 and LEC1-LIKE in Developing Seeds. Plant Physiol 156: 1577-1588

Tungsuchat-Huang T, Maliga P (2012) Visual marker and *Agrobacterium*-delivered recombinase enable the manipulation of the plastid genome in greenhouse-grown tobacco plants. Plant J 70: 717-725

Valkov V T, Gargano D, Manna C, Formisano G, Dix P J, Gray J C, Scotti N, Cardi T (2011) High efficiency plastid transformation in potato and regulation of transgene expression in leaves and tubers by alternative 5' and 3' regulatory sequences. Transgenic Res 20: 137-151

Verma S, Chinnusamy V, Bansal K (2008) A Simplified Floral Dip Method for Transformation of *Brassica napus* and *B. carinata*. J Plant Biochemistry and Biotechnology 17: 197-200

Wallis J G, Browse J (2010) Lipid biochemists salute the genome. Plant J 61: 1092-1106

Wang T W, Wu W, Zhang C G, Nowack L M, Liu Z D, Thompson J E (2005) Antisense suppression of deoxyhypusine synthase by vacuum-infiltration of *Agrobacterium* enhances growth and seed yield of canola. Physiol Plant 124: 493-503

Wang W C, Menon G, Hansen G (2003) Development of a novel *Agrobacterium*-mediated transformation method to recover transgenic *Brassica napus* plants. Plant Cell Rep 22: 274-281

Weigel D, Mott R (2009) The 1001 genomes project for *Arabidopsis thaliana*. Genome biology 10: 107

Willey D L, Gray J C (1989) Two small open reading frames are co-transcribed with the pea chloroplast genes for the polypeptides of cytochrome b-559. Curr Genet 15: 213-220

Willey D L, Gray J C (1990) An open reading frame encoding a putative haem-binding polypeptide is cotranscribed with the pea chloroplast gene for apocytochrome f. Plant Mol Biol 15: 347-356

Wilson D N (2014) Ribosome-targeting antibiotics and mechanisms of bacterial resistance. Nat Rev Microbiol 12: 35-48

Wirmer J, Westhof E (2006) Molecular contacts between antibiotics and the 30S ribosomal particle. Methods Enzymol 415: 180-202

Xie K, Yang Y (2013) RNA-guided genome editing in plants using a CRISPR-Cas system. Mol Plant 6: 1975-1983

Yamazaki H, Tasaka M, Shikanai T (2004) PPR motifs of the nucleus-encoded factor, PGR3, function in the selective and distinct steps of chloroplast gene expression in *Arabidopsis*. Plant J 38: 152-163

Yang L, Guell M, Niu D, George H, Lesha E, Grishin D, Aach J, Shrock E, Xu W, Poci J, Cortazio R, Wilkinson R A, Fishman J A, Church G (2015) Genome-wide inactivation of porcine endogenous retroviruses (PERVs). Science 350: 1101-1104

Ye G N, Colburn S, Xu C W, Hajdukiewicz P T J, Staub J M (2003) Persistance of unselected transgenic DNA during a plastid transformation and segregation approach to herbicide resistance. Plant Physiol 133: 402-410

Zhang J, Khan S A, Hasse C, Ruf S, Heckel D G, Bock R (2015) Pest control. Full crop protection from an insect pest by expression of long double-stranded RNAs in plastids. Science 347: 991-994

Zhao X, Liang G, Li X, Zhang X (2014) Hormones regulate in vitro organ regeneration from leaf-derived explants in *Arabidopsis*. Am J Plant Sci 5: 3535-3550

Zhao X Y, Su Y H, Zhang C L, Wang L, Li X, Zhang X S (2013) Differences in capacities of in vitro organ regeneration between two *Arabidopsis* ecotypes Wassilewskija and Columbia. Plant Cell Tissue Organ Cult. 112: 65-74

Zubko M K, Day A (1998) Stable albinism induced without mutagenesis: a model for ribosome-free plastid inheritance. Plant J 15: 265-271

While certain of the preferred embodiments of the present invention have been described and specifically exemplified above, it is not intended that the invention be limited to such embodiments. Various modifications may be made thereto without departing from the scope and spirit of the present invention, as set forth in the following claims.

---

What is claimed is:

1. A method for increasing plastid transformation efficiency in plastids of higher plants recalcitrant to plastid transformation, comprising;
    a) providing a plant comprising a nonfunctional or defective ACC2 nuclear gene;
    b) introducing one or more plastid transformation vectors into the plastids in cells from said plant, said one or more vectors comprising an aadA spectinomycin resistance marker sequence and a nucleic acid sequence encoding a sequence of interest;
    c) contacting said cells with spectinomycin and selecting plant cells which are resistant to spectinomycin and accumulate said sequence of interest in said plastids; and
    d) culturing said plant cells under conditions suitable to regenerate a transplastomic plant therefrom, wherein the number of transformants exceeds those obtained from plants of step a) which lack said non functional or defective ACC2 gene,
    wherein said ACC2 gene is inactivated in said plant using CRISPR/Cas prior to plastid transformation and said plant is a *Camelina* ssp. plant.

2. The method of claim 1, wherein said sequence of interest is green fluorescent protein.

3. The method of claim 1, further comprising excising said aadA spectinomycin resistance marker sequence from said plant.

4. The method of claim 1, wherein said sequence of interest is a nucleic acid encoding a molecule selected from the group consisting of a protein conferring herbicide resistance, a protein conferring insect resistance, an insecticidal protein, a vaccine, an antibody, regulatory RNA, dsRNA, siRNA, and a shRNA.

5. A method for increasing plastid transformation efficiency in plastids of higher plants recalcitrant to plastid transformation, comprising;
    a) providing a plant comprising a nonfunctional or defective ACC2 nuclear gene;
    b) introducing one or more plastid transformation vectors into the plastids in cells from said plant, said one or more vectors comprising a nucleic acid sequence conferring resistance to a plastid translation inhibitor and a nucleic acid sequence encoding a sequence of interest;

c) contacting said cells with said inhibitor and selecting plant cells which are resistant to said inhibitor and accumulate said sequence of interest in said plastids; and d) culturing said plant cells under conditions suitable to regenerate a transplastomic plant therefrom, wherein the number of transformants exceeds those obtained from plants of step a) which lack said non functional or defective ACC2 gene, wherein said plastid translation inhibitor is selected from the group consisting of kanamycin, chloramphenicol, tobramycin and gentamycin.

6. The method of claim 5, wherein said plant is selected from the group consisting of *Arabidopsis* ssp., *Brassica* ssp., and *Camelina* ssp.

7. The method of claim 5, wherein the plant of step a) is a naturally occurring mutant which encodes non-functional or defective ACC2.

8. The method of claim 5, wherein said inhibitor is kanamycin.

9. The method of claim 5, wherein said inhibitor is chloramphenicol and said nucleic acid sequence encodes chloramphenicol acetyl transferase.

10. The method of claim 5, wherein said recalcitrant plant is selected from *Arabidopsis thaliana, Arabidopsis lyrate, Camelina sativa, Camelina rubella, Brassica oleracea, Brassica napus, Brassica rapa*, and *Lesquerella fendleri*.

* * * * *